(12) United States Patent
Klaerner et al.

(10) Patent No.: US 10,391,118 B2
(45) Date of Patent: *Aug. 27, 2019

(54) PROTON-BINDING POLYMERS FOR ORAL ADMINISTRATION

(71) Applicant: Tricida, Inc., South San Francisco, CA (US)

(72) Inventors: Gerrit Klaerner, Hillsborough, CA (US); Eric F. Connor, Los Gatos, CA (US); Randi K. Gbur, Brisbane, CA (US); Matthew J. Kade, Berkeley, CA (US); Paul H. Kierstead, Oakland, CA (US); Jerry M. Buysse, Los Altos, CA (US); Michael J. Cope, Berkeley, CA (US); Kalpesh N. Biyani, Dublin, CA (US); Son H. Nguyen, Milpitas, CA (US); Scott M. Tabakman, Palo Alto, CA (US)

(73) Assignee: TRICIDA, INC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/002,306

(22) Filed: Jun. 7, 2018

(65) Prior Publication Data

US 2019/0134075 A1    May 9, 2019

Related U.S. Application Data

(63) Continuation of application No. 15/715,934, filed on Sep. 26, 2017, now Pat. No. 9,993,500, which is a
(Continued)

(51) Int. Cl.
*A61K 31/785* (2006.01)
*C08F 226/02* (2006.01)
*C08G 73/02* (2006.01)

(52) U.S. Cl.
CPC .......... *A61K 31/785* (2013.01); *C08F 226/02* (2013.01); *C08G 73/02* (2013.01); *C08G 73/024* (2013.01); *Y10T 428/2982* (2015.01)

(58) Field of Classification Search
None
See application file for complete search history.

(56) References Cited

U.S. PATENT DOCUMENTS

| 5,496,545 A | 3/1996 | Holmes-Farley et al. |
| 5,643,951 A | 7/1997 | Stacpoole et al. |

(Continued)

FOREIGN PATENT DOCUMENTS

| CN | 1503676 A | 6/2004 |
| CN | 1878822 A | 12/2006 |

(Continued)

OTHER PUBLICATIONS

Steed et al., Supramolectular Chemistry, 2nd Edition, John Wiley & Sons, Ltd. West Sussex, United Kingdom, 216-279.
(Continued)

*Primary Examiner* — Brian Gulledge
(74) *Attorney, Agent, or Firm* — Bryan Cave Leighton Paisner LLP

(57) ABSTRACT

Pharmaceutical compositions for and methods of treating an animal, including a human, and methods of preparing such compositions. The pharmaceutical compositions contain crosslinked amine polymers and may be used, for example, to treat diseases or other metabolic conditions in which removal of protons and/or chloride ions from the gastrointestinal tract would provide physiological benefits such as normalizing serum bicarbonate concentrations and the blood pH in an animal, including a human.

46 Claims, 2 Drawing Sheets

Related U.S. Application Data continuation of application No. 14/944,844, filed on Nov. 18, 2015, now Pat. No. 9,925,214, which is a continuation of application No. 14/311,852, filed on Jun. 23, 2014, now Pat. No. 9,205,107, which is a continuation of application No. PCT/US2014/041152, filed on Jun. 5, 2014.

(60) Provisional application No. 61/831,445, filed on Jun. 5, 2013.

(56) References Cited

U.S. PATENT DOCUMENTS

| | | |
|---|---|---|
| 5,648,355 A | 7/1997 | Theoharides |
| 5,679,717 A | 10/1997 | Mandeville, III et al. |
| 6,271,264 B1 | 8/2001 | Dhal et al. |
| 6,444,221 B1 | 9/2002 | Shapiro |
| 6,468,964 B1 | 10/2002 | Rowe |
| 6,485,703 B1 | 11/2002 | Cote et al. |
| 6,733,780 B1 | 5/2004 | Tyler et al. |
| 6,877,408 B2 | 4/2005 | Kubota et al. |
| 7,335,795 B2 | 2/2008 | Chang et al. |
| 7,342,083 B2 | 3/2008 | Chang et al. |
| 7,449,605 B2 | 11/2008 | Chang et al. |
| 7,459,502 B2 | 12/2008 | Connor et al. |
| 7,608,674 B2 | 10/2009 | Connor et al. |
| 7,754,199 B2 | 7/2010 | Chang et al. |
| 7,767,768 B2 | 8/2010 | Chang et al. |
| 7,767,851 B2 | 8/2010 | Kwok et al. |
| 7,846,425 B2 | 12/2010 | Hegde et al. |
| 7,964,182 B2 | 6/2011 | Omray et al. |
| 7,985,418 B2 | 7/2011 | Bhagat et al. |
| 8,003,600 B2 | 8/2011 | Hageman |
| 8,084,397 B2 | 12/2011 | Li et al. |
| 8,163,799 B2 | 4/2012 | Dhal et al. |
| 8,187,634 B2 | 5/2012 | Hedge et al. |
| 8,273,384 B2 | 9/2012 | Wurzberger |
| 8,394,416 B2 | 3/2013 | Bianchi et al. |
| 8,399,025 B2 | 3/2013 | Roy et al. |
| 8,445,014 B2 | 5/2013 | Charmot et al. |
| 8,530,519 B2 | 9/2013 | Ueno |
| 8,586,097 B2 | 11/2013 | Liu et al. |
| 8,842,086 B2 | 9/2014 | Ogg |
| 9,205,107 B2 | 12/2015 | Klaerner et al. |
| 9,993,500 B2 * | 6/2018 | Klaerner ............... A61K 31/785 |
| 2002/0110560 A1 | 8/2002 | Demuth et al. |
| 2002/0159968 A1 | 10/2002 | Petersen et al. |
| 2003/0039627 A1 | 2/2003 | Holmes-Farley et al. |
| 2003/0091530 A1 | 5/2003 | Goto et al. |
| 2003/0092782 A1 | 5/2003 | Goto et al. |
| 2004/0059065 A1 | 3/2004 | Goto et al. |
| 2005/0090553 A1 | 4/2005 | Shapiro |
| 2005/0220750 A1 | 10/2005 | Robert et al. |
| 2005/0220751 A1 | 10/2005 | Charmot et al. |
| 2005/0220752 A1 | 10/2005 | Charmot et al. |
| 2005/0220889 A1 | 10/2005 | Charmot et al. |
| 2005/0220890 A1 | 10/2005 | Charmot et al. |
| 2005/0234129 A1 | 10/2005 | Sutton et al. |
| 2006/0024336 A1 | 2/2006 | Charmot et al. |
| 2006/0034847 A1 | 2/2006 | Yun et al. |
| 2007/0098678 A1 | 5/2007 | Bhagat et al. |
| 2007/0135335 A1 | 6/2007 | Collier et al. |
| 2007/0293429 A1 | 12/2007 | Nestor |
| 2008/0200533 A1 | 8/2008 | Krishnan |
| 2008/0207766 A1 | 8/2008 | Devane |
| 2008/0214440 A1 | 9/2008 | Nestor |
| 2008/0248012 A1 | 10/2008 | Suematsu |
| 2008/0317729 A1 | 12/2008 | Kasch et al. |
| 2009/0053317 A1 | 2/2009 | Vigo et al. |
| 2009/0131338 A1 | 5/2009 | Saou et al. |
| 2009/0155368 A1 | 6/2009 | Holmes-Farley et al. |
| 2009/0155370 A1 | 6/2009 | Cope et al. |
| 2009/0156647 A1 | 6/2009 | Molino et al. |
| 2009/0162314 A1 | 6/2009 | Huval et al. |
| 2009/0325860 A1 | 12/2009 | Costantino et al. |
| 2010/0008988 A1 | 1/2010 | Mehta et al. |
| 2010/0035992 A1 | 2/2010 | Bhushan et al. |
| 2010/0080858 A1 | 4/2010 | Satou et al. |
| 2010/0104527 A1 | 4/2010 | Mansky et al. |
| 2010/0111891 A1 | 5/2010 | Albrecht et al. |
| 2010/0113479 A1 | 5/2010 | Choudhury et al. |
| 2010/0124542 A1 | 5/2010 | Dhal et al. |
| 2010/0129309 A1 | 5/2010 | Dhal et al. |
| 2010/0135950 A1 | 6/2010 | Huval et al. |
| 2010/0166696 A1 | 7/2010 | Dhal et al. |
| 2010/0166861 A1 | 7/2010 | Lynch |
| 2010/0189679 A1 | 7/2010 | Inoue et al. |
| 2010/0234309 A1 | 9/2010 | Cooper et al. |
| 2010/0316589 A1 | 12/2010 | Charmot et al. |
| 2011/0064820 A1 | 3/2011 | Omray et al. |
| 2011/0081413 A1 | 4/2011 | Omray |
| 2011/0142952 A1 | 6/2011 | Harris et al. |
| 2011/0189121 A1 | 8/2011 | Genth et al. |
| 2011/0263493 A1 | 10/2011 | Dugi et al. |
| 2011/0268666 A1 | 11/2011 | Friedman et al. |
| 2012/0219626 A1 | 8/2012 | Osinga |
| 2012/0259098 A1 | 10/2012 | Baker, Jr. et al. |
| 2012/0288471 A1 | 11/2012 | Huval et al. |
| 2013/0022570 A1 | 1/2013 | Kopping et al. |
| 2013/0130995 A1 | 5/2013 | Currie et al. |
| 2013/0131202 A1 | 5/2013 | Albrecht et al. |
| 2013/0137772 A1 | 5/2013 | Bergeron |
| 2013/0156720 A1 | 6/2013 | Currie |
| 2013/0189215 A1 | 7/2013 | Lees et al. |
| 2013/0189216 A1 | 7/2013 | Albrecht et al. |
| 2013/0251667 A1 | 9/2013 | Dhal et al. |
| 2013/0266533 A1 | 10/2013 | Dhal et al. |
| 2013/0345303 A1 | 12/2013 | Poradosu et al. |
| 2014/0105848 A1 | 4/2014 | Klaerner et al. |
| 2016/0074430 A1 | 3/2016 | Klaerner et al. |
| 2018/0280428 A1 | 10/2018 | Klaerner et al. |

FOREIGN PATENT DOCUMENTS

| | | |
|---|---|---|
| EP | 2168992 | 3/2010 |
| WO | 9940990 | 8/1999 |
| WO | 2005041900 A2 | 5/2005 |
| WO | 2005041902 | 5/2005 |
| WO | 2005092039 | 10/2005 |
| WO | 2007038801 | 4/2007 |
| WO | 2008011047 | 1/2008 |
| WO | 2008027551 | 3/2008 |
| WO | 2008103368 | 8/2008 |
| WO | 2009023544 | 2/2009 |
| WO | 2009097127 | 8/2009 |
| WO | 2009125443 | 10/2009 |
| WO | 2012011063 A1 | 1/2012 |
| WO | 2014197725 | 12/2014 |
| WO | 2015066593 | 2/2015 |
| WO | 2016094685 A1 | 6/2016 |
| WO | 2017193024 | 11/2017 |
| WO | 2017193050 | 11/2017 |
| WO | 2017193064 | 11/2017 |

OTHER PUBLICATIONS

Adrogue et al., Respiratory Acidosis, Respiratory Alkalosis, and Mixed Disorders in Comprehensive Clinical Nephrology, 4th Edition, 2010, Elsevier Saunders, St. Louis, Missouri, Ch. 14, 176-189.

Ballmer et al., Chronic metabolic acidosis decreases albumin synthesis and induces negative nitrogen balance in humans, The Journal of Clinical Investigation, 1995, 95: 39-45.

Brezina et al., Acid loading during treatment with sevelamer hydrocholoride: Mechanisms and clinical implications, Kidney International, 2004, 66(90): S39-S45.

Chmelarova, Short chain fatty acids and colonic health, Bratisl Lek Listy, 2007, 108(8): 354-358.

D'Agostino et al., Alterations in the ionic composition of icotonic saline solutins instilled into the colon, The Journal of Clinical Investigation, 1953, 32(5): 444-448.

(56) References Cited

OTHER PUBLICATIONS

Davis et al., Evaluation of Chlorida/Biocarbonate exchange in the human colon in vivo, The Journal of Clinical Investigation, 1983, 71:201-207.
De Brito-Ashurst et al, Bicarbonate Supplementation Slows Progression of CKD and Improves Nutritional Status, J Am Soc Nephrol, 2009, 20(9): 2075-2084.
Dobre et al., Association of Serum Bicarbonate With Risk of Renal and Cardiovascular Outcomes in CKD: A Report From the Chronic Renal Insufficiency Cohort (CRIC) Study, American Journal of Kidney Diseases, 2013, 62(4): 670-678.
Dubose, Jr., et al., Renal Tubular Acidosis in Acid Base and Electrolyte Disorders: A Companion to Brenner & Rector's The Kidney, Elsevier Health Sciences, 2002, Ch. 11, 189-206.
Farwell et al., Serum anion gap, bicarbonate and biomarkers of inflammation in healthy individuals in a national survey, Canadian Medical Association Journal, 2010, 182(2): 137-141.
Fortran et al., Ionic constituents and osmolality of gastric and small-intestinal fluids after eating, New Series, 1966, 11(7):503-521.
Goldberg, Approach to Acid-Base Disorders, Ch 11, 2005, 104-109.
Heart Failure Society of America, HFSA 2010 Guideline Executive Summary Executive Summary: HFSA 2010 Comprehensive Heart Failure Practice Guideline, Journal of Cardiac Failure, 2010, 16(6), 259 pages.
Hospria Sodium Bicarb IV ANDA labels and packaging, 5 pages.
Kielland, J., Individual Activity Coefficients of Ions in Aqueous Solutions, 1937, 59, 1675-1678, retrieved from www.ufscar.br.
Lemann, Jr., et al., Bone buffering of acid and base in humans, Am J Physiol Renal Physiol, 2003, 285:F811-F832.
Lemann Jr. et al., The Effects of Chronic Acid Loads in Normal Man: Further Evidence for the Participation of Bone Mineral in the Defense against Chronic Metabolic Acidosis, Journal of Clinical Investigation, 1966, 45(10):1608-1614.
Mitch, W. E., Influence of Metabolic Acidosis on Nutrition, American Journal of Kidney Diseases, 29(5):xlvi-xlviii.
National Kidney Foundation, K/DOQI Clinical Practice Guidelines for Bone Metabolism and Disease in Chronic Kidney Disease, 2003, 42(4), Supp. 3.
National Kidney Foundation, K/DOQI Nutrition Guidelines, American Journal of Kidney Diseases, 2000, 35(6), Supp. 2.
Phisitkul et al., Dietary protein causes a decline in the glomerular filtration rate of the remnant kidney mediated by metabolic acidosis and endothelin receptors, Kidney International, 2008, 73: 192-199.
Raphael et al., Serum bicarbonate and mortality in adults in NHANES III, Nephrol Dial Transplant, 2013, 28: 1207-1213.
Shannon, R.D., Revised Effective Ionic Radii and Systematic Studies of Interatomie Distances in Halides and Chaleogenides, Acta Cryst, 1976, A32: 751-767.
Stevens et al., Electrolyte composition of endoscopically collected duodenal drainage fluid after synthetic porcine secretin stimulation in healthy subjects, Gastrointestinal Endoscopy, 2004, 60(3): 351-355.
Sullivan et al., Halogenated Solvents, Trichloroethylene, and Methylene Chloride in Clinical Environmental Health and Toxic Exposures, 2nd Ed., Ch. 58, 1999, Lippincott Williams & Wilkins, Philadelphia, PA.
Szerlip, Metabolic Acidosis, Ch. 8, p. 74-89.
Widmer et al., Serum Electrolyte and Acid Base Composition, Arch Intern Med, 1979, 139, 1099-1102.
Wrong et al., In Vivo dialysis of faeces as a method of stool analysis, Clinical Science, 1967, 33(1): 89-100.
Yaqoob, M. M., Acidosis and progression of chronic kidney disease, Current Opinion in Nephrology and Hypertension, 2010, 19:489-492.
Remington, The Science and Practice of Pharmacy, 21st Ed., Edited by D. B. Troy, p. 317-318 and 745-775, Lippincott Williams & Wilkins, Baltimore, Maryland.
Patent Cooperation Treaty, International Search Report and Written Opinion for PCT/US2014/041152, dated Nov. 27, 2014, 10 pages.
Nakaki et al., Effect of fatty acids on the phosphate binding of TRK-390, a novel, highly selective phosphate-binding polymer, European Journal of Pharmacology, 2013, 714(1-3): 312-317.
Akizawa, et al., Long-Term Treatment of Hyperphosphatemia With Bixalomer in Japanese Hemodialysis Patients, Therapeutic Apheresis and Dialysis, 2013, 17(6): 612-619.
Ito et al., Treatment of Hyperphosphatemia With Bixalomer in Japanese Patients on Long-Term Hemodialysis With Gastrointestinal Symptoms, Therapeutic Apheresis and Dialysis, 2014; 18(Supplement 2):19-23.
Shima et al., Clinical Experiences of Bixalomer Usage at Our Hospital, Therapeutic Apheresis and Dialysis 2014; 18(Supplement 2):13-18.
Kioussis et al., Reactive nitrogen and phosphorus removal from aquaculture wastewater effluents using polymer hydrogels, Aquacultural Engineering, 2000, 23: 315-332.
Kioussis et al., Phosphate binding polymeric hydrogels for aquaculture wastewater remediation, Aquacultural Engineering, 1999, 19: 163-178.
Kioussis et al., Selective anion sorption and recovery from wastewater by polyelectrolyte hydrogels, Polymer Preprints, 2000, 41(2): 1679-1680.
Inoue et al., Highly selective and low-swelling phosphate-binding polymer for hyperphosphatema theraphy, Chem. Letters, 41, 932-933 2012.
Franch et al., Catabolism in Uremia: The Impact of Metabolic Acidosis, J. Am. Soc. Nephrol., 9: S78-S81 1998.
Stevens et al., Electrolyte composition of endoscopically collected duodenal drainage fluid after synthetic porcine secretin stimulation in healthy subjects, Gastroentestinal Endoscopy, 60(3); 351-355 2004.
European Patent Office, Extended European Search Report issued for App. No. 17177221.3, 8 pages dated Jan. 23, 2018.
Akizawa et al., Randomized Controlled Trial of Bixalomer Versus Sevelamer Hydrochloride in Hemodialysis Patients With Hyperphosphatemia, Therapeutic Aphreresis and Dialysis, 18(2):122-131 2014.
Akizawa et al., Bixalomer in Hyperphosphatemic Patients With Chronic Kidney Disease Not on Dialysis: Phase 3 Randomized Trial, Therapeutic Apheresis and Dialysis, 10 pages 2016.
Akizawa et al., Long-Term Safety and Efficacy of Bixalomer in Hyperphosphatemic Patients With Chronic Kidney Disease Not on Dialysis, Therapeutic Apheresis and Dialysis, 7pgs 2017.
Beaubien-Souligny et al., The effect of lanthanum carbonate on metabolic acidosis in patients with chronic kidney disease stage IV, V and V-D, Int Urol Nephrol, 7pg. 2015.
Bezzaoucha et al., The role of sevelamer carbonate in increasing serum bicarbonate in hyperphosphatemic pre-dialysis patients who have metabolic acidosis, Intern. Journal of Clinical Pharmacology and Therapeutics, 51(Dec. 2013): 989-990 2013.
Bushinsky et al., Randomized, Controlled Trial of TRC101 to Increase Serum Bicarbonate in Patients with CKD, Clin J Am Soc Nephrol, 10pg. 2018.
Chen et al., Epidemiology of Acid-Base Derangements in CKD, Adv Chronic Kidney Dis., 24(5):280-288 2017.
Garneata et al., Ketoanalogue-Supplemented Vegetarian Very Low-Protein Diet and CKD Progression, J Am Soc Nephrol 27:2164-2176 2016.
Pai et al., Comparison of Sevelamer Hydrochloride and Sevelamer Carbonate: Risk of Metabolic Acidosis and Clinical Implications, Pharmacotherapy, 29(5):554-561 2009.
Mahajan et al., Daily oral sodium bicarbonate preserves glomerular filtration rate by slowing its decline in early hypertensive nephropathy, Kidney International, 78, 303-309 2010.
Raphael, K.L., Metabolic Acidosis and Subclinical Metabolic Acidosis in CKD, J Am Soc Nephrol 29, 7pg 2017.
Rombola et al, Lanthanum carbonate: a postmarketing observational study of efficacy and safety, Jour Nephrol, 25(4): 490-496 2012.
Susantitaphong et al., Short- and Long-Term Effects of Alkali Therapy in Chronic Kidney Disease: A Systematic Review. Am J Nephrol, 35:540-547 2012.

(56) References Cited

OTHER PUBLICATIONS

Thet et al., Differential effects of phosphate binders on pre-dialysis serum bicarbonate in end-stage kidney disease patients on maintenance haemodialysis, BMC Nephrology, 14:205-215 2013.
Goraya et al., A Comparison of Treating Metabolic Acidosis in CKD Stage 4 Hypertensive Kidney Disease with Fruits and Vegetables or Sodium Bicarbonate, Clin J Am Soc Nephrol 8: 371-381 2013.
Goraya et al., Treatment of metabolic acidosis in patients with stage 3 chronic kidney disease with fruits and vegetables or oral bicarbonate reduces urine angiotensinogen and preserves glomerular filtration rate, Kidney International, 86:1031-1038 2014.
Goraya et al., Management of the Metabolic Acidosis of Chronic Kidney Disease, Adv Chronic Kidney Dis., 24(5):298-304 2017.
Hatakeyama et al., Switching hemodialysis patients from sevelamer hydrochloride to bixalomer: a single-center, non-randomized analysis of efficacy and effects on gastrointestinal symptoms and metabolic acidosis, BMC Nephrology, 14:222-229 2013.
Husted et al., NaHC03 and NaCl tolerance in chronic renal failure II, Clinical Nephrology, 7(1):21-25 1977.
Lindley et al., Correction of metabolic acidosis after conversion from sevelamer hydrochloride to lanthanum carbonate, NDT Plus, 3:196 2008.
Navaneethan et al., Serum Bicarbonate and Mortality in Stage 3 and Stage 4 Chronic Kidney Disease, Clinical Journal of the American Society of Nephrology, 6(10): 2395-2402 2011.
Patent Cooperation Treaty, International Search Report for PCT/US2015/065041, dated Mar. 22, 2016, 5 pgs.
Patent Cooperation Treaty, International Search Report for PCT/US2017/031395, 6 pages dated Aug. 8, 2017.
Patent Cooperation Treaty, International Search Report for PCT/US2017/031344, 5 pages dated Aug. 8, 2017.
Patent Cooperation Treaty, International Search Report for PCT/US2017/031378, 5 pages dated Sep. 20, 2017.
Russian Federal Institute of Industrial Property, Search Report for 2015155596, 2 pages dated May 8, 2018.
Patent Cooperation Treaty, International Search Report for PCT/US2018/059092, 3pgs. dated Jan. 8, 2019.
Kraut, Disturbances in Acid-Base, Potassium, and Sodium Balance in Patients With CKD: New Insights and Novel Therapies, Adv Chronic Kidney Dis., 2017, 24(5): 272-273 2017.
Patent Cooperation Treaty, International Search Report for PCT/US2018/059093, 3pgs. dated Jan. 8, 2019.
Wesson et al., Veverimer versus placebo in patients with metabolic acidosis associated with chronic kidney disease: a multicentre, randomised, double-blind, controlled, phase 3 trial, The Lancet, 11 pgs. Mar. 8, 2019.

\* cited by examiner

PROTON-BINDING POLYMERS FOR ORAL ADMINISTRATION

This application is a continuation of U.S. application Ser. No. 15/715,934 filed on Sep. 26, 2017; which is a continuation of Ser. No. 14/944,844 filed on Nov. 18, 2015 and issued as U.S. Pat. No. 9,925,214 on Mar. 27, 2018; which is a continuation of U.S. application Ser. No. 14/311,852 filed on Jun. 23, 2014 and issued as U.S. Pat. No. 9,205,107 on Dec. 8, 2015; which is a continuation of International Application No. PCT/US2014/041152, filed on Jun. 5, 2014; which claims priority to the U.S. provisional application 61/831,445, filed on Jun. 5, 2013, the entire contents of which are hereby incorporated by reference herein in their entireties.

The present invention generally relates to proton-binding polymers for oral administration that may be used in the treatment of metabolic acidosis.

Metabolic acidosis is the result of metabolic and dietary processes that in various disease states create a condition in which non-volatile acids accumulate in the body, causing a net addition of protons (H+) or the loss of bicarbonate ($HCO_3^-$). Metabolic acidosis occurs when the body accumulates acid from metabolic and dietary processes and the excess acid is not completely removed from the body by the kidneys. Chronic kidney disease is often accompanied by metabolic acidosis due to the reduced capacity of the kidney to excrete hydrogen ions secondary to an inability to reclaim filtered bicarbonate ($HCO_3^-$), synthesize ammonia (ammoniagenesis), and excrete titratable acids. Clinical practice guidelines recommend initiation of alkali therapy in patients with non-dialysis-dependent chronic kidney disease (CKD) when the serum bicarbonate level is <22 mEq/L to prevent or treat complications of metabolic acidosis. (Clinical practice guidelines for nutrition in chronic renal failure, K/DOQI, National Kidney Foundation, Am. J. Kidney Dis. 2000; 35:S1-140; Raphael, K L, Zhang, Y, Wei, G, et al. 2013, Serum bicarbonate and mortality in adults in NHANES III, Nephrol. Dial. Transplant 28: 1207-1213). These complications include malnutrition and growth retardation in children, exacerbation of bone disease, increased muscle degradation, reduced albumin synthesis, and increased inflammation. (Leman, J, Litzow, J R, Lennon, E J. 1966. The effects of chronic acid loads in normal man: further evidence for the participation of bone mineral in the defense against chronic metabolic acidosis, J. Clin. Invest. 45: 1608-1614; Franch H A, Mitch W E, 1998, Catabolism in uremia: the impact of metabolic acidosis, J. Am. Soc. Nephrol. 9: S78-81; Ballmer, P E, McNurlan, M A, Hulter, H N, et al., 1995, Chronic metabolic acidosis decreases albumin synthesis and induces negative nitrogen balance in humans, J. Clin. Invest. 95: 39-45; Farwell, W R, Taylor, E N, 2010, Serum anion gap, bicarbonate and biomarkers of inflammation in healthy individuals in a national survey, CMAJ 182:137-141). Overt metabolic acidosis is present in a large proportion of patients when the estimated glomerular filtration rate is below 30 ml/min/1.73 m². (KDOQI bone guidelines: American Journal of Kidney Diseases (2003) 42:S1-S201. (suppl); Widmer B, Gerhardt R E, Harrington J T, Cohen J J, Serum electrolyte and acid base composition: The influence of graded degrees of chronic renal failure, Arch Intern Med 139:1099-1102, 1979; Dobre M, Yang, W, Chen J, et. al., Association of serum bicarbonate with risk of renal and cardiovascular outcomes in CKD: a report from the chronic renal insufficiency cohort (CRIC) study. Am. J. Kidney Dis. 62: 670-678, 2013; Yaqoob, M M. Acidosis and progression of chronic kidney disease. Curr. Opin. Nephrol. Hypertens. 19: 489-492, 2010).

Metabolic acidosis, regardless of etiology, lowers extracellular fluid bicarbonate and, thus, decreases extracellular pH. The relationship between serum pH and serum bicarbonate is described by the Henderson-Hasselbalch equation $$pH=pK'+\log [HCO3-]/[(0.03\times Paco2)]$$

where 0.03 is the physical solubility coefficient for $CO_2$, [$HCO_3^-$] and $PaCO_2$ are the concentrations of bicarbonate and the partial pressure of carbon dioxide, respectively.

There are several laboratory tests that can be used to define metabolic acidosis. The tests fundamentally measure either bicarbonate ($HCO_3^-$) or proton (H+) concentration in various biological samples, including venous or arterial blood.

The most useful measurements for the determination of acidosis rely on a measurement of the venous plasma bicarbonate (or total carbon dioxide [$tCO_2$]), serum electrolytes Cl⁻, K+, and Na+, and a determination of the anion gap. In the clinical laboratory, measurement of venous plasma or serum electrolytes includes an estimation of the tCO2. This measurement reflects the sum of circulating $CO_2$ [i.e., the total $CO_2$ represented by bicarbonate ($HCO_3^-$), carbonic acid, ($H_2CO_3$) and dissolved $CO_2$ (0.03× $Pco_2$)]. tCO2 can also be related to $HCO_3^-$ by using a simplified and standardized form of the Henderson-Hasselbalch equation: $tCO2=HCO_3^-+0.03\ PCO_2$, where $PCO_2$ is the measured partial pressure of $CO_2$. Since $HCO_3^-$ concentration is greater than 90% of the tCO2, and there are small amounts of $H_2CO_3$, then venous tCO2 is often used as a reasonable approximation of the venous $HCO_3^-$ concentration in the blood. Especially during chronic kidney disease, an abnormal plasma $HCO_3^-$ value <24-26 mEq/L generally indicates metabolic acidosis.

Changes in serum Cl⁻ concentration can provide additional insights into possible acid-base disorders, particularly when they are disproportionate to changes in serum Na+ concentration. When this occurs, the changes in serum Cl⁻ concentration are typically associated with reciprocal changes in serum bicarbonate. Thus, in metabolic acidosis with normal anion gap, serum Cl⁻ increases >105 mEq/L as serum bicarbonate decreases <24-26 mEq/L.

Calculation of the anion gap [defined as the serum Na+—(Cl⁻+$HCO_3^-$)] is an important aspect of the diagnosis of metabolic acidosis. Metabolic acidosis may be present with a normal or an elevated anion gap. However, an elevated anion gap commonly signifies the presence of metabolic acidosis, regardless of the change in serum $HCO_3^-$. An anion gap greater than 20 mEq/L (normal anion gap is 8 to 12 mEq/L) is a typical feature of metabolic acidosis.

Arterial blood gases are used to identify the type of an acid-base disorder and to determine if there are mixed disturbances. In general, the result of arterial blood gas measures should be coordinated with history, physical exam and the routine laboratory data listed above. An arterial blood gas measures the arterial carbon dioxide tension ($P_aCO_2$), acidity (pH), and the oxygen tension ($P_aO_2$). The $HCO_3^-$ concentration is calculated from the pH and the $Paco_2$. Hallmarks of metabolic acidosis are a pH <7.35, $P_aCO_2$<35 mm Hg and $HCO_3^-$<22 mEq/L. The value of $P_aO_2$ (normal 80-95 mmHg) is not used in making the diagnosis of metabolic acidosis but may be helpful in determining the cause. Acid-base disturbance are first classified as respiratory or metabolic. Respiratory disturbances are those caused by abnormal pulmonary elimination of $CO_2$, producing an excess (acidosis) or deficit (alkalosis) of $CO_2$ (carbon dioxide) in the extracellular fluid. In respiratory acid-base disorders, changes in serum bicarbonate ($HCO_3^-$) are initially a direct consequence of the change in $P_{CO_2}$ with a greater increase in $P_{CO_2}$ resulting in an increase in $HCO_3^-$. (Adrogue H J, Madias N E, 2003, Respiratory acidosis, respiratory alkalosis, and mixed disorders, in Johnson R J, Feehally J (eds): Comprehensive Clinical Nephrology. London, C V Mosby, pp. 167-182). Metabolic disturbances are those caused by excessive intake of, or metabolic production or losses of, nonvolatile acids or bases in the extracellular fluid. These changes are reflected by changes in the concentration of bicarbonate anion ($HCO_3^-$) in the blood; adaptation in this case involves both buffering (immediate), respiratory (hours to days) and renal (days) mechanisms. (DuBose T D, MacDonald G A: renal tubular acidosis, 2002, in DuBose T D, Hamm L L (eds): Acid-base and electrolyte disorders: A companion to Brenners and Rector's the Kidney, Philadelphia, W B Saunders, pp. 189-206).

The overall hydrogen ion concentration in the blood is defined by the ratio of two quantities, the serum $HCO_3^-$ content (regulated by the kidneys) and the $P_{CO_2}$ content (regulated by the lungs) and is expressed as follows:

$$[H^+] \propto (P_{CO_2}/[HCO_3^-])$$

The consequence of an increase in the overall hydrogen ion concentration is a decline in the major extracellular buffer, bicarbonate. Normal blood pH is between 7.38 and 7.42, corresponding to a hydrogen ion ($H^+$) concentration of 42 to 38 nmol/L (Goldberg M: Approach to Acid-Base Disorders. 2005. In Greenberg A, Cheung A K (eds) Primer on Kidney Diseases, National Kidney Foundation, Philadelphia, Elsevier-Saunders, pp. 104-109.). Bicarbonate ($HCO_3^-$) is an anion that acts to buffer against pH disturbances in the body, and normal levels of plasma bicarbonate range from 22-26 mEq/L (Szerlip H M: Metabolic Acidosis, 2005, in Greenberg A, Cheung A K (eds) Primer on Kidney Diseases, National Kidney Foundation, Philadelphia, Elsevier-Saunders, pp. 74-89.). Acidosis is the process which causes a reduction in blood pH (acidemia) and reflects the accumulation of hydrogen ion ($H^+$) and its consequent buffering by bicarbonate ion ($HCO_3^-$) resulting in a decrease in serum bicarbonate. Metabolic acidosis can be represented as follows:

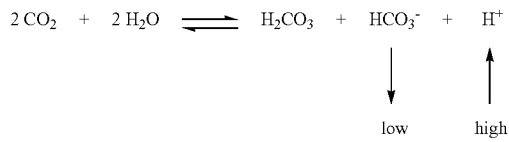

(Clinical practice guidelines for nutrition in chronic renal failure. K/DOQI, National Kidney Foundation. Am. J. Kidney Dis. 2000; 35:S1-140). Using this balance equation, the loss of one $HCO_3^-$ is equivalent to the addition of one $H^+$ and conversely, the gain of one $HCO_3^-$ is equivalent to the loss of one $H^+$. Thus, changes in blood pH, particularly increases in $H^+$ (lower pH, acidosis) can be corrected by increasing serum $HCO_3^-$ or, equivalently, by decreasing serum $H^+$.

In order to maintain extracellular pH within the normal range, the daily production of acid must be excreted from the body. Acid production in the body results from the metabolism of dietary carbohydrates, fats and amino acids. Complete oxidation of these metabolic substrates produces water and $CO_2$. The carbon dioxide generated by this oxidation (20,000 mmol/day) is efficiently exhaled by the lungs, and represents the volatile acid component of acid-base balance.

In contrast, nonvolatile acids (~50-100 mEq/day) are produced by the metabolism of sulfate- and phosphate-containing amino acids and nucleic acids. Additional nonvolatile acids (lactic acid, butyric acid, acetic acid, other organic acids) arise from the incomplete oxidation of fats and carbohydrates, and from carbohydrate metabolism in the colon, where bacteria residing in the colon lumen convert the substrates into small organic acids that are then absorbed into the bloodstream. The impact of short chain fatty acids on acidosis is somewhat minimized by anabolism, for example into long-chain fatty acids, or catabolism to water and $CO_2$.

The kidneys maintain pH balance in the blood through two mechanisms: reclaiming filtered $HCO_3^-$ to prevent overall bicarbonate depletion and the elimination of nonvolatile acids in the urine. Both mechanisms are necessary to prevent bicarbonate depletion and acidosis.

In the first mechanism, the kidneys reclaim $HCO_3^-$ that is filtered by the glomerulus. This reclamation occurs in the proximal tubule and accounts for ~4500 mEq/day of reclaimed $HCO_3^-$. This mechanism prevents $HCO_3^-$ from being lost in the urine, thus preventing metabolic acidosis. In the second mechanism, the kidneys eliminate enough $H^+$ to equal the daily nonvolatile acid production through metabolism and oxidation of protein, fats and carbohydrates. Elimination of this acid load is accomplished by two distinct routes in the kidney, comprising active secretion of $H^+$ ion and ammoniagenesis. The net result of these two interconnected processes is the elimination of the 50-100 mEq/day of nonvolatile acid generated by normal metabolism.

Thus, normal renal function is needed to maintain acid-base balance. During chronic kidney disease, filtration and reclamation of $HCO_3^-$ is impaired as is generation and secretion of ammonia. These deficits rapidly lead to chronic metabolic acidosis which is, itself, a potent antecedent to end-stage renal disease. With continued acid production from metabolism, a reduction in acid elimination will disturb the $H^+/HCO_3^-$ balance such that blood pH falls below the normal value of pH=7.38-7.42.

Treatment of metabolic acidosis by alkali therapy is usually indicated to raise and maintain the plasma pH to greater than 7.20. Sodium bicarbonate ($NaHCO_3$) is the agent most commonly used to correct metabolic acidosis. $NaHCO_3$ can be administered intravenously to raise the serum $HCO_3^-$ level adequately to increase the pH to greater than 7.20. Further correction depends on the individual situation and may not be indicated if the underlying process is treatable or the patient is asymptomatic. This is especially true in certain forms of metabolic acidosis. For example, in high-anion gap (AG) acidosis secondary to accumulation of organic acids, lactic acid, and ketones, the cognate anions are eventually metabolized to $HCO_3^-$. When the underlying disorder is treated, the serum pH corrects; thus, caution should be exercised in these patients when providing alkali to raise the pH much higher than 7.20, to prevent an increase in bicarbonate above the normal range (>26 mEq/L).

Citrate is an appropriate alkali therapy to be given orally or IV, either as the potassium or sodium salt, as it is metabolized by the liver and results in the formation of three moles of bicarbonate for each mole of citrate. Potassium citrate administered IV should be used cautiously in the presence of renal impairment and closely monitored to avoid hyperkalemia.

Intravenous sodium bicarbonate ($NaHCO_3$) solution can be administered if the metabolic acidosis is severe or if correction is unlikely to occur without exogenous alkali administration. Oral alkali administration is the preferred route of therapy in persons with chronic metabolic acidosis. The most common alkali forms for oral therapy include $NaHCO_3$ tablets where 1 g of $NaHCO_3$ is equal to 11.9 mEq of $HCO_3^-$. However, the oral form of $NaHCO_3$ is not approved for medical use and the package insert of the intravenous sodium bicarbonate solution includes the following contraindications, warnings and precautions (Hospira label for NDC 0409-3486-16):

Contraindications: Sodium Bicarbonate Injection, USP is contraindicated in patients who are losing chloride by vomiting or from continuous gastrointestinal suction, and in patients receiving diuretics known to produce a hypochloremic alkalosis.

Warnings: Solutions containing sodium ions should be used with great care, if at all, in patients with congestive heart failure, severe renal insufficiency and in clinical states in which there exists edema with sodium retention. In patients with diminished renal function, administration of solutions containing sodium ions may result in sodium retention. The intravenous administration of these solutions can cause fluid and/or solute overloading resulting in dilution of serum electrolyte concentrations, overhydration, congested states or pulmonary edema.

Precautions: [ . . . ] The potentially large loads of sodium given with bicarbonate require that caution be exercise in the use of sodium bicarbonate in patients with congestive heart failure or other edematous or sodium-retaining states, as well as in patients with oliguria or anuria.

Acid-base disorders are common in chronic kidney disease and heart failure patients. Chronic kidney disease (CKD) progressively impairs renal excretion of the approximately 1 mmol/kg body weight of hydrogen ions generated in healthy adults (Yaqoob, M M. 2010, Acidosis and progression of chronic kidney disease, Curr. Opin. Nephrol. Hyperten. 19:489-492.). Metabolic acidosis, resulting from the accumulation of acid ($H^+$) or depletion of base ($HCO_3^-$) in the body, is a common complication of patients with CKD, particularly when the glomerular filtration rate (GFR, a measure of renal function) falls below 30 ml/min/1.73 $m^2$. Metabolic acidosis has profound long term effects on protein and muscle metabolism, bone turnover and the development of renal osteodystrophy. In addition, metabolic acidosis influences a variety of paracrine and endocrine functions, again with long term consequences such as increased inflammatory mediators, reduced leptin, insulin resistance, and increased corticosteroid and parathyroid hormone production (Mitch W E, 1997, Influence of metabolic acidosis on nutrition, Am. J. Kidney Dis. 29:46-48.). The net effect of sustained metabolic acidosis in the CKD patient is loss of bone and muscle mass, a negative nitrogen balance, and the acceleration of chronic renal failure due to hormonal and cellular abnormalities (De Brito-Ashurst I, Varagunam M, Raftery M J, et al, 2009, Bicarbonate supplementation slows progression of CKD and improves nutritional status, J. Am. Soc. Nephrol. 20: 2075-2084). Conversely, the potential concerns with alkali therapy in CKD patients include expansion of extracellular fluid volume associated with sodium ingestion, resulting in the development or aggravation of hypertension, facilitation of vascular calcification, and the decompensation of existing heart failure. CKD patients of moderate degree (GFR at 20-25% of normal) first develop hyperchloremic acidosis with a normal anion gap due to the inability to reclaim filtered bicarbonate and excrete proton and ammonium cations. As they progress toward the advanced stages of CKD the anion gap increases, reflective of the continuing degradation of the kidney's ability to excrete the anions that were associated with the unexcreted protons. Serum bicarbonate in these patients rarely goes below 15 mmol/L with a maximum elevated anion gap of approximately 20 mmol/L. The non-metabolizable anions that accumulate in CKD are buffered by alkaline salts from bone (Lemann J Jr, Bushinsky D A, Hamm L L Bone buffering of acid and base in humans. Am. J. Physiol Renal Physiol. 2003 November, 285(5):F811-32).

The majority of patients with chronic kidney disease have underlying diabetes (diabetic nephropathy) and hypertension, leading to deterioration of renal function. In almost all patients with hypertension a high sodium intake will worsen the hypertension. Accordingly, kidney, heart failure, diabetes and hypertensive guidelines strictly limit sodium intake in these patients to less than 1.5 g or 65 mEq per day (HFSA 2010 guidelines, Lindenfeld 2010, J Cardiac Failure V16 No 6 P 475). Chronic anti-hypertensive therapies often induce sodium excretion (diuretics) or modify the kidney's ability to excrete sodium and water (such as, for example, Renin Angiotensin Aldosterone System inhibiting "RAASi" drugs). However, as kidney function deteriorates, diuretics become less effective due to an inability of the tubule to respond. The RAASi drugs induce life-threatening hyperkalemia as they inhibit renal potassium excretion. Given the additional sodium load, chronically treating metabolic acidosis patients with amounts of sodium-containing base that often exceed the total daily recommended sodium intake is not a reasonable practice. As a consequence, oral sodium bicarbonate is not commonly prescribed chronically in these diabetic nephropathy patients. Potassium bicarbonate is also not acceptable as patients with CKD are unable to readily excrete potassium, leading to severe hyperkalemia.

Despite these shortcomings, the role of oral sodium bicarbonate has been studied in the small subpopulation of non-hypertensive CKD patients. As part of the Kidney Research National Dialogue, alkali therapy was identified as having the potential to slow the progression of CKD, as well as to correct metabolic acidosis. The annual age-related decline in glomerular filtration rate (GFR) after the age of 40 is 0.75-1.0 ml/min/1.73 $m^2$ in normal individuals. In CKD patients with fast progression, a steeper decline of >4 ml/min/1.73 $m^2$ annually can be seen.

In one outcome study, De Brito-Ashurst et al showed that bicarbonate supplementation preserves renal function in CKD (De Brito-Ashurst I, Varagunam M, Raftery M J, et al, 2009, Bicarbonate supplementation slows progression of CKD and improves nutritional status, J. Am. Soc. Nephrol. 20: 2075-2084). The study randomly assigned 134 adult patients with CKD (creatinine clearance [CrCl] 15 to 30 ml/min per 1.73 $m^2$) and serum bicarbonate 16 to 20 mmol/L to either supplementation with oral sodium bicarbonate or standard of care for 2 years. The average dose of bicarbonate in this study was 1.82 g/day, which provides 22 mEq of bicarbonate per day. The primary end points were rate of CrCl decline, the proportion of patients with rapid decline of CrCl (>3 ml/min per 1.73 $m^2$/yr), and end-stage renal disease ("ESRD") (CrCl <10 ml/min). Compared with the control group, decline in CrCl was slower with bicarbonate supplementation (decrease of 1.88 ml/min per 1.73 $m^2$ for patients receiving bicarbonate versus a decrease of 5.93 ml/min per 1.73 $m^2$ for control group; P <0.0001). Patients supplemented with bicarbonate were significantly less likely to experience rapid progression (9% versus 45%; relative risk 0.15; 95% confidence interval 0.06 to 0.40; P <0.0001).

Similarly, fewer patients supplemented with bicarbonate developed ESRD (6.5% versus 33%; relative risk 0.13; 95% confidence interval 0.04 to 0.40; P <0.001).

Hyperphosphatemia is a common co-morbidity in patients with CKD, particularly in those with advanced or end-stage renal disease. Sevelamer hydrochloride is a commonly used ion-exchange resin that reduces serum phosphate concentration. However, reported drawbacks of this agent include metabolic acidosis apparently due to the net absorption of HCl in the process of binding phosphate in the small intestine. Several studies in patients with CKD and hyperphosphatemia who received hemodialysis or peritoneal dialysis found decreases in serum bicarbonate concentrations with the use of sevelamer hydrochloride (Brezina, 2004 Kidney Int. V66 S90 (2004) S39-S45; Fan, 2009 Nephrol Dial Transplant (2009) 24:3794).

Among the various aspects of the present invention, therefore, may be noted compositions for and methods of treating an animal, including a human, and methods of preparing such compositions. The compositions comprise crosslinked amine polymers and may be used, for example, to treat diseases or other metabolic conditions in which removal of protons and/or chloride ions from the gastrointestinal tract would provide physiological benefits. For example, the polymers described herein may be used to regulate acid-base related diseases in an animal, including a human. In one such embodiment, the polymers described herein may be used to normalize serum bicarbonate concentrations and the blood pH in an animal, including a human. By way of further example, the polymers described herein may be used in the treatment of acidosis. There are several distinct physiologic conditions that describe this imbalance, each of which can be treated by a polymer that binds and removes HCl.

Metabolic acidosis resulting from a net gain of acid includes processes that increase endogenous hydrogen ion production, such as ketoacidosis, L-lactic acidosis, D-lactic acidosis and salicylate intoxication. Metabolism of ingested toxins such as methanol, ethylene glycol and paraldehyde can also increase hydrogen ion concentration. Decreased renal excretion of hydrogen ions as in uremic acidosis and distal (type I) renal tubular acidosis is another cause of net gain of acid in the body resulting in metabolic acidosis. Metabolic acidosis resulting from a loss of bicarbonate is a hallmark of proximal (type II) renal tubular acidosis. In addition, gastrointestinal loss of bicarbonate in acute or chronic diarrhea also results in metabolic acidosis. Primary or secondary hypoaldosteronism are common disorders causing hyperkalemia and metabolic acidosis and underlie the classification of type IV renal tubular acidosis. Hyporeninemic hypoaldosteronism is the most frequently encountered variety of this disorder.

Another way of describing metabolic acidosis is in terms of the anion gap. Causes of high anion gap acidosis include diabetic ketoacidosis, L-lactic acidosis, D-lactic acidosis, alcoholic ketoacidosis, starvation ketoacidosis, uremic acidosis associated with advanced renal failure (CKD Stages 4-5), salicylate intoxication, and selected toxin exposure due to ingestion including methanol, ethylene, propylene glycol and paraldehyde. Causes of normal anion gap acidosis include early stage renal failure (CKD Stages 1-3), gastrointestinal loss of bicarbonate due to acute or chronic diarrhea, distal (type I) renal tubular acidosis, proximal (type II) renal tubular acidosis, type IV renal tubular acidosis, dilutional acidosis associated with large volume intravenous fluid administration, and treatment of diabetic ketoacidosis resulting from ketones lost in the urine.

With regard to lactic acidosis, hypoxic lactic acidosis results from an imbalance between oxygen balance and oxygen supply and is associated with tissue ischemia, seizure, extreme exercise, shock, cardiac arrest, low cardiac output and congestive heart failure, severe anemia, severe hypoxemia and carbon monoxide poisoning, vitamin deficiency and sepsis. In other types of lactic acidosis, oxygen delivery is normal but oxidative phosphorylation is impaired, often the result of cellular mitochondrial defects. This is commonly seen in inborn errors of metabolism or from the ingestion of drugs or toxins. Alternate sugars used for tube feedings or as irrigants during surgery (e.g., fructose, sorbitol) can also result in metabolism that triggers lactic acidosis.

There are three main classifications of renal tubular acidosis, each with distinctive etiologies with several subtypes. Distal (type I) renal tubular acidosis can be caused by hereditary and genomic changes, particularly mutation in the $HCO_3^-/Cl^-$ exchanger (AE1) or $H^+$/ATPase. Examples of acquired distal (type I) renal tubular acidosis include hyperparathyroidism, Sjogren's syndrome, medullary sponge kidney, cryoglobulinemia, systemic lupus erythematosus, kidney transplant rejection, chronic tubulointerstitial disease and exposure to various drugs including amphotericin B, lithium, ifosfamide, foscarnet, toluene and vanadium. A special classification of distal (type IV) renal tubular acidosis with hyperkalemia is found in lupus nephritis, obstructive nephropathy, sickle cell anemia, and voltage defects. Hereditary examples include pseudohypoaldosteronism type I and pseudohypoaldosteronism type II (Gordon's disease) and exposure to certain drugs (amiloride, triamterene, trimethoprim, and pentamidine) can also result in distal (type IV) renal tubular acidosis with hyperkalemia. Proximal (type II) renal tubular acidosis can be caused by hereditary or acquired causes. Hereditary causes include Wilson's disease and Lowe's syndrome. Acquired causes include cystinosis, galactosemia, multiple myeloma, light chain disease, amyloidosis, vitamin D deficiency, lead and mercury ingestion, and exposure to certain drugs including ifosfamide, cidofovir, aminoglycosides, and acetazolamide. Isolated defects in bicarbonate reabsorption can be a cause of proximal (type II) renal tubular acidosis; example of such defects include exposure to carbonic anhydrase inhibitors, acetazolamide, topiramate, sulfamylon and carbonic anhydrase deficiency. Combined proximal and distal renal tubular acidosis (type III) is uncommon and results from defects in both proximal bicarbonate reabsorption and distal proton secretion. Mutations in the gene for cystolic carbonic anhydrase can cause the defect, as well as certain drugs including ifosfamide. Type IV renal tubular acidosis with hyperkalemia is a cause of metabolic acidosis. The main etiology behind this type of acidosis is aldosterone deficiency; hypoaldosteronism results from primary adrenal failure, the syndrome of hyporeninemic hypoaldosteronism (Type IV RTA) commonly seen in elderly individuals, Addison's disease, and pseudohypoaldosteronism type I due to mineralocorticoid resistance. Chronic interstitial nephritis due to analgesic nephropathy, chronic pyelonephritis, obstructive nephropathy and sickle cell disease can also create an acidosis with hyperkalemia. Finally, drugs such as amiloride, spironolactone, triamterene, trimethoprim, heparin therapy, NSAIDs, angiotensin receptor blockers and angiotensin-converting enzyme inhibitors can induce metabolic acidosis accompanied by hyperkalemia.

All of the above causes and etiologies of metabolic acidosis are treatable with a polymer designed to bind and remove HCl in the gastrointestinal tract.

The method of treatment generally involves administering a therapeutically effective amount of a crosslinked amine polymer having the capacity to remove protons and chloride ions from the gastrointestinal tract of an animal, such as a human. In general, such crosslinked amine polymers have two or more of the characteristics of relatively low swelling, relatively high proton and chloride ion binding, and/or relatively low binding of interfering anions such as phosphate, citrate, short chain fatty acids and bile acids. In the following examples and embodiments, unless otherwise noted, the crosslinked amine polymers are used in the free amine form, and in order to bind anions require protonation of the amines. As such, many of the assays report anion binding, and due to the requisite low degree of amine quaternization, anion binding is presumed to approximate the amount of proton binding. For example, in one embodiment the crosslinked amine polymer possesses at least two of the following characteristics: (i) a proton-binding capacity and a chloride binding capacity of at least about 5 mmol/g in Simulated Gastric Fluid ("SGF"); (ii) a Swelling Ratio of less than about 5; (iii) a chloride to phosphate ion binding ratio of at least about 0.35:1, respectively, in Simulated Small Intestine Inorganic Buffer ("SIB"), (iv) a selectivity for chloride over other anions in Simulated Small Intestine Organic and Inorganic Buffer ("SOB"), (v) a mean particle size of about 80-120 microns, (vi) retention of more than about 50% of the HCl bound when submitted to a chloride retention assay ("CRA", defined below), (vii) no more than about 40% of quaternized amine groups before administration to an animal, including a human, as measured in the quaternized amine assay ("QAA") in order to ensure proton binding which constitutes the main therapeutic action of the polymer, (viii) a chloride to interfering anion binding ratio of at least about 0.35:1, respectively, in "SOB", (ix) a molecular weight per nitrogen of between 50 and 170 daltons, and/or (x) a crosslinker weight percent range of 25 to 90%. For example, in one such embodiment the crosslinked amine polymer possesses two characteristics of characteristics "(i)" to "(x)" identified in this paragraph. By way of further example, in one such embodiment the crosslinked amine polymer possesses at least three characteristics of characteristics "(i)" to "(x)" identified in this paragraph. By way of further example, in one such embodiment the crosslinked amine polymer possesses at least four characteristics of characteristics "(i)" to "(x)" identified in this paragraph. By way of further example, in one such embodiment the crosslinked amine polymer possesses at least five characteristics of characteristics "(i)" to "(x)" identified in this paragraph. By way of further example, in one such embodiment the crosslinked amine polymer possesses at least six characteristics of characteristics "(i)" to "(x)" identified in this paragraph. By way of further example, in one such embodiment the crosslinked amine polymer possesses at least seven characteristics of characteristics "(i)" to "(x)" identified in this paragraph. By way of further example, in one such embodiment the crosslinked amine polymer possesses at least eight characteristics of characteristics "(i)" to "(x)" identified in this paragraph.

In one embodiment, the crosslinked amine polymer is administered as a pharmaceutical composition comprising the crosslinked amine polymer and, optionally, a pharmaceutically acceptable carrier, diluent or excipient, or combination thereof that do not significantly interfere with the proton and/or chloride binding characteristics of the crosslinked amine polymer in vivo. Optionally, the pharmaceutical composition may also comprise an additional therapeutic agent.

In some embodiments, the pharmaceutical composition comprises a crosslinked amine polymer having (i) a chloride to phosphate ion binding ratio of at least 0.35:1, respectively, in Simulated Small Intestine Inorganic Buffer ("SIB"), and (ii) a Swelling Ratio not in excess of about 5.

In some embodiments, the pharmaceutical composition comprises a crosslinked amine polymer having (i) a selectivity for chloride over other anions in Simulated Small Intestine Organic and Inorganic Buffer ("SOB"), and (ii) a Swelling Ratio not in excess of about 5.

In some embodiments, the pharmaceutical composition comprises a crosslinked amine polymer having (i) a proton-binding capacity and a chloride binding capacity of at least 5 mmol/g in Simulated Gastric Fluid; and (ii) a Swelling Ratio not in excess of about 2.

In some embodiments, the pharmaceutical composition comprises a crosslinked amine polymer having (i) a proton-binding capacity and a chloride binding capacity of at least 5 mmol/g in Simulated Gastric Fluid; (ii) a Swelling Ratio of less than 5, and (iii) a chloride to phosphate ion binding ratio of at least 0.35:1, respectively, in Simulated Small Intestine Inorganic Buffer ("SIB").

In some embodiments, the pharmaceutical composition comprises a crosslinked amine polymer having (i) a proton-binding capacity and a chloride binding capacity of at least 5 mmol/g in Simulated Gastric Fluid; (ii) a Swelling Ratio of less than 5, and (iii) a selectivity for chloride over other anions in Simulated Small Intestine Organic and Inorganic Buffer ("SOB").

In some embodiments, the pharmaceutical composition comprises a crosslinked amine polymer having i) a chloride binding capacity of >2 mmol/g in Simulated Organic/Inorganic Buffer (SOB) and ii) >50% retention of the bound chloride when assessed in the chloride retention assay (CRA).

In some embodiments, the pharmaceutical composition comprises a crosslinked amine polymer having i) a chloride binding capacity of >5 mmol/g in simulated gastric fluid (SGF) and ii) has no more than 40% of quaternized amine groups as measured in the quaternized amine assay (QAA).

In some embodiments, the pharmaceutical composition comprises a crosslinked amine polymer comprising the residue of an amine corresponding to Formula 1

Formula 1 wherein $R_1$, $R_2$ and $R_3$ are independently hydrogen, hydrocarbyl, or substituted hydrocarbyl provided, however, at least one of $R_1$, $R_2$ and $R_3$ is other than hydrogen, and the crosslinked amine polymer has (i) an equilibrium proton binding capacity of at least 5 mmol/g and a chloride ion binding capacity of at least 5 mmol/g in an aqueous simulated gastric fluid buffer ("SGF") containing 35 mM NaCl and 63 mM HCl at pH 1.2 and 37° C., and (ii) an equilibrium swelling ratio in deionized water of about 2 or less.

In some embodiments, the pharmaceutical composition comprises a crosslinked amine polymer comprising the residue of an amine corresponding to Formula 1

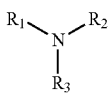

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen, the crosslinked amine polymer has an equilibrium swelling ratio in deionized water of about 5 or less, and the crosslinked amine polymer binds a molar ratio of chloride ions to interfering ions of at least 0.35:1, respectively, in an interfering ion buffer at 37° C. wherein (i) the interfering ions are phosphate ions and the interfering ion buffer is a buffered solution at pH 5.5 of 36 mM chloride and 20 mM phosphate or (ii) the interfering ions are phosphate, citrate and taurocholate ions and the interfering ion buffer is a buffered solution at pH 6.2 including 36 mM chloride, 7 mM phosphate, 1.5 mM citrate, and 5 mM taurocholate. Statted differently, in the embodiment in which the interfering ion buffer is a buffered solution at pH 5.5 of 36 mM chloride and 20 mM phosphate, the ratio of chloride to interfering ions is a ratio of chloride to phosphate ions and in the embodiment in which the interfering ion buffer is a buffered solution at pH 6.2 including 36 mM chloride, 7 mM phosphate, 1.5 mM citrate, and 5 mM taurocholate, the ratio of chloride to interfering ions is a ratio of chloride ions to the combined (total) amount of phosphate, citrate and taurocholate ions.

In some embodiments, the crosslinked amine polymer is derived from the polymerization of an amine corresponding to Formula 2

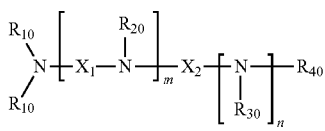

Formula 2 wherein m and n are independently non-negative integers;

$R_{10}$, $R_{20}$, $R_{30}$, and $R_{40}$ are independently hydrogen, hydrocarbyl, or substituted hydrocarbyl, $X_1$ is

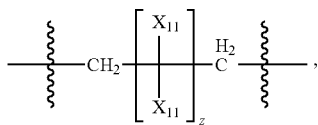

$X_2$ is hydrocarbyl or substituted hydrocarbyl;

each is independently hydrogen, hydrocarbyl, substituted hydrocarbyl, hydroxyl, amino, boronic acid, or halo; and z is a non-negative number.

A further aspect of the present disclosure is a method of crosslinking a proton-binding intermediate with a polyfunctional crosslinker to provide one or more of the characteristics of relatively low swelling, relatively high proton and chloride ion binding, and/or relatively low interference from interfering ions. The proton-binding intermediate may be, for example, an oligomer or polymer containing amine moieties prepared by (i) substitution polymerization, (ii) addition polymerization, or (iii) post-polymerization crosslinking of an intermediate.

Other aspects and features will be in part apparent and in part pointed out hereinafter.

ABBREVIATIONS AND DEFINITIONS

Figure 1A:
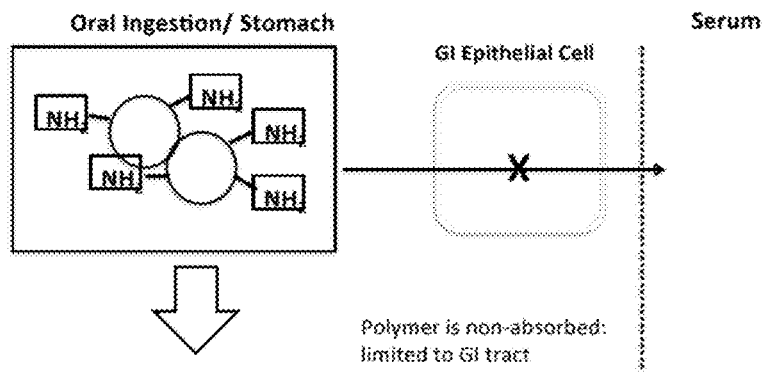
FIG. 1A-1C is a flow chart schematically depicting the mechanism of action of the polymer when passing through the gastrointestinal tract of an individual from oral ingestion/stomach (FIG. 1A), to the upper GI tract (FIG. 1B) to the lower GI tract/colon (FIG. 1C).

The following definitions and methods are provided to better define the present invention and to guide those of ordinary skill in the art in the practice of the present invention. Unless otherwise noted, terms are to be understood according to conventional usage by those of ordinary skill in the relevant art.

The term "acrylamide" denotes a moiety having the structural formula $H_2C=CH-C(O)NR-$*, where * denotes the point of attachment of the moiety to the remainder of the molecule and R is hydrogen, hydrocarbyl, or substituted hydrocarbyl.

The term "acrylic" denotes a moiety having the structural formula $H_2C=CH-C(O)O-$*, where * denotes the point of attachment of the moiety to the remainder of the molecule.

The term "alicyclic", "alicyclo" or "alicyclyl" means a saturated monocyclic group of 3 to 8 carbon atoms and includes cyclopentyl, cyclohexyl, cycloheptyl, and the like.

The term "aliphatic" denotes saturated and non-aromatic unsaturated hydrocarbyl moieties having, for example, one to about twenty carbon atoms or, in specific embodiments, one to about twelve carbon atoms, one to about ten carbon atoms, one to about eight carbon atoms, or even one to about four carbon atoms. The aliphatic groups include, for example, alkyl moieties such as methyl, ethyl, n-propyl, isopropyl, n-butyl, isobutyl, sec-butyl, tert-butyl, pentyl, iso-amyl, hexyl and the like, and alkenyl moieties of comparable chain length.

The term "alkanol" denotes an alkyl moiety that has been substituted with at least one hydroxyl group. In some embodiments, alkanol groups are "lower alkanol" groups comprising one to six carbon atoms, one of which is attached to an oxygen atom. In other embodiments, lower alkanol groups comprise one to three carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In certain embodiments, alkenyl groups are "lower alkenyl" groups having two to about four carbon atoms. Examples of alkenyl groups include, but are not limited thereto, ethenyl, propenyl, allyl, vinyl, butenyl and 4-methylbutenyl. The terms "alkenyl group" and "lower alkenyl group", encompass groups having "cis" or "trans" orientations, or alternatively, "E" or "Z" orientations.

The term "alkyl group" as used, either alone or within other terms such as "haloalkyl group," "aminoalkyl group" and "alkylamino group", encompasses saturated linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkylamino group" refers to amino groups directly attached to the remainder of the molecule via the nitrogen atom of the amino group and wherein the nitrogen atom of the alkylamino group is substituted by one or two alkyl groups. In some embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino, pentamethyleneamine and the like.

The term "allyl" denotes a moiety having the structural formula $H_2C=CH-CH_2-*$, where * denotes the point of attachment of the moiety to the remainder of the molecule and the point of attachment is to a heteroatom or an aromatic moiety.

The term "allylamine" denotes a moiety having the structural formula $H_2C=CH-CH_2N(X_8)(X_9)$, wherein $X_8$ and $X_9$ are independently hydrogen, hydrocarbyl, or substituted hydrocarbyl, or $X_8$ and $X_9$ taken together form a substituted or unsubstituted alicyclic, aryl, or heterocyclic moiety, each as defined in connection with such term, typically having from 3 to 8 atoms in the ring.

The term "amine" or "amino" as used alone or as part of another group, represents a group of formula $-N(X_8)(X_9)$, wherein $X_8$ and $X_9$ are independently hydrogen, hydrocarbyl, or substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring.

The term "aminoalkyl group" encompasses linear or branched alkyl groups having one to about ten carbon atoms, any one of which may be substituted with one or more amino groups, directly attached to the remainder of the molecule via an atom other than a nitrogen atom of the amine group(s). In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 5 to 10 carbon atoms, typically 5 to 7 carbon atoms, and more typically 5 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "bead" is used to describe a crosslinked polymer that is substantially spherical in shape.

The term "binds" as used herein in connection with a polymer and one or more ions, that is, a cation (e.g. "proton-binding" polymer) and an anion, is an "ion-binding" polymer and/or when it associates with the ion, generally though not necessarily in a non-covalent manner, with sufficient association strength that at least a portion of the ion remains bound under the in vitro or in vivo conditions in which the polymer is used for sufficient time to effect a removal of the ion from solution or from the body.

The term "chloride retention assay" or "CRA" denotes an assay where the retention of chloride and other anions by free amine test polymers, as well as that of free amine sevelamer and bixalomer control polymers, is evaluated by exposing them to competing anion concentrations typical of the colon lumen. The anions released from the polymers and anions retained by the polymers under these conditions are measured. The first step in the retention assay is to perform a specific organic/inorganic buffer assay (SOB screen) as described elsewhere herein. Blank tubes that contain no polymer are included and processed in an identical manner throughout the retention screen. Instead of discarding the polymer and SOB matrix from the assay tubes, the contents are transferred to solid phase extraction (SPE) tubes, fitted with 20 micrometer pore-size frits. The excess SOB matrix is removed either by applying negative pressure to the bottom of the SPE tubes, or positive pressure to the tops. The SOB assay tubes are rinsed twice with deionized water and the contents transferred to the SPE tubes to ensure that as much of the polymer as possible is recovered. Retention assay matrix is then added to the SPE tubes. The retention assay matrix comprises 50 mM 2-(N-morpholino)ethanesulfonic acid (MES), 100 mM sodium acetate, 5 mM sodium phosphate, 15 mM sulphate, adjusted to pH 6.2. The concentrations of potential competing anions reflect typical late-colon lumen concentrations (Wrong, 0 et al. [1965] Clinical Science 28, 357-375). Chloride is omitted since the objective is to measure chloride retention and bicarbonate is omitted since it is unstable due to conversion to water and $CO_2$. Retention buffer is added to achieve a final polymer concentration of 2.5 mg/ml (assuming no loss of polymer since the original weighing into the SOB assay tubes). The SPE tubes are capped and sealed and incubated at 37° C. for approximately 40 hours. A 600 microliter sample is removed, filtered, diluted if necessary, and assayed for anion content as described above for SOB. For each tested polymer, chloride, citrate and taurocholate released from the polymer in retention matrix are calculated using the following calculation $$\text{mmol of ion released } g^{-1} \text{ polymer} = \frac{([\text{Ion}]ret - [\text{Ion}] \, retblank \times \text{dilution factor}}{2.5}$$

where [Ion] ret corresponds to the concentration of an ion in the retention matrix at the end of the 48 hour incubation, [Ion] retblank corresponds to the value of that particular ion in the retention matrix from the blank SPE tubes, dilution factor is the dilution factor if necessary, and 2.5 is the polymer concentration in mg/ml. The excess retention matrix is removed either by applying negative pressure to the bottom of the SPE tubes, or positive pressure to the tops. The SPE columns are washed briefly with 10 ml of deionized water and excess water is removed. Ions that remain bound to the polymers are eluted by adding 0.2M NaOH to the SPE tubes to achieve a final polymer concentration of 2.5 mg/ml (assuming no loss of polymer since the original weighing into the SOB assay tubes) and incubating for 16-20 hours at 37° C. A 600 microliter sample is removed, filtered, diluted if necessary, and assayed for anion content as described above for SOB. For each tested polymer, chloride, phosphate, citrate and taurocholate released from the polymer in retention matrix is calculated using the following calculation $$\text{mmol of ion released } g^{-1} \text{ polymer} = \frac{([\text{Ion}]elu - [\text{Ion}] \; elublank \times \text{dilution factor}}{2.5}$$

where [Ion] elu corresponds to the concentration of an ion in the 0.2M NaOH elution matrix at the end of the 16-20 hours incubation, [Ion] elublank corresponds to the value of that particular ion in the elution matrix from the blank SPE tubes, dilution factor is the dilution factor if necessary, and 2.5 is the polymer concentration in mg/ml.

The term "crosslink density" denotes the average number of connections of the amine containing repeat unit to the rest of the polymer. The number of connections can be 2, 3, 4 and higher. Repeat units in linear, non crosslinked polymers are incorporated via 2 connections. In order to form an insoluble gel, the number of connections should be greater than 2. Low crosslinking density materials such as sevelamer have on average about 2.1 connections between repeat units. More crosslinked systems such as bixalomer have on average about 4.6 connections between the amine-containing repeat units. "Crosslinking density" represents a semi-quantitative measure based on the ratios of the starting materials used. Limitations include the fact that it does not account for different crosslinking and polymerization methods. For example, small molecule amine systems require higher amounts of crosslinker as the crosslinker also serves as the monomer to form the polymer backbone whereas for radical polymerizations the polymer chain is formed independent from the crosslinking reaction. This can lead to inherently higher crosslinking densities under this definition for the substitution polymerization/small molecule amines as compared to radical polymerization crosslinked materials.

The term "crosslinker" as used, either alone or within other terms, encompasses hydrocarbyl or substituted hydrocarbyl, linear or branched molecules capable of reacting with any of the described monomers, or the infinite polymer network, as described in Formula 1, more than one time. The reactive group in the crosslinker can include, but is not limited to alkyl halide, epoxide, phosgene, anhydride, carbamate, carbonate, isocyanate, thioisocyanate, esters, activated esters, carboxylic acids and derivatives, sulfonates and derivatives, acyl halides, aziridines, alpha,beta-unsaturated carbonyls, ketones, aldehydes, pentafluoroaryl groups, vinyl, allyl, acrylate, methacrylate, acrylamide, methacrylamide, styrenic, acrylonitriles and combinations thereof. In one exemplary embodiment, the crosslinker's reactive group will include alkyl halide, epoxide, anhydrides, isocyanates, allyl, vinyl, acrylamide, and combinations thereof. In one such embodiment, the crosslinker's reactive group will be alkyl halide, epoxide, or allyl.

The term "diallylamine" denotes an amino moiety having two allyl groups.

The term "ethereal" denotes a moiety having an oxygen bound to two separate carbon atoms as depicted the structural formula $*-H_xC-O-CH_x-*$, where * denotes the point of attachment to the remainder of the moiety and x independently equals 0, 1, 2, or 3.

The term "gel" is used to describe a crosslinked polymer that has an irregular shape.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are mono-haloalkyl, dihaloalkyl and polyhaloalkyl groups including perhaloalkyl. A monohaloalkyl group, for example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaliphatic" describes a chain of 1 to 25 carbon atoms, typically 1 to 12 carbon atoms, more typically 1 to 10 carbon atoms, and most typically 1 to 8 carbon atoms, and in some embodiments 1 to 4 carbon atoms that can be saturated or unsaturated (but not aromatic), containing one or more heteroatoms, such as halogen, oxygen, nitrogen, sulfur, phosphorus, or boron. A heteroatom atom may be a part of a pendant (or side) group attached to a chain of atoms (e.g., —CH(OH)—CH(NH$_2$)— where the carbon atom is a member of a chain of atoms) or it may be one of the chain atoms (e.g., —ROR— or —RNHR— where each R is aliphatic). Heteroaliphatic encompasses heteroalkyl and heterocyclo but does not encompass heteroaryl.

The term "heteroalkyl" describes a fully saturated heteroaliphatic moiety.

The term "heteroaryl" means a monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. "Heteroarylene" means a divalent heteroaryl radical.

The term "heteroatom" means an atom other than carbon and hydrogen. Typically, but not exclusively, heteroatoms are selected from the group consisting of halogen, sulfur, phosphorous, nitrogen, boron and oxygen atoms. Groups containing more than one heteroatom may contain different heteroatoms.

The term "heterocyclo," "heterocyclic," or heterocyclyl" means a saturated or unsaturated group of 4 to 8 ring atoms in which one or two ring atoms are heteroatom such as N, O, B, P and S(O)$_n$, where n is an integer from 0 to 2, the remaining ring atoms being carbon. Additionally, one or two ring carbon atoms in the heterocyclyl ring can optionally be replaced by a —C(O)— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

"Initiator" is a term used to describe a reagent that initiates a polymerization.

The term "molecular weight per nitrogen" or "MW/N" represents the calculated molecular weight in the polymer per nitrogen atom. It represents the average molecular weight to present one amine function within the crosslinked polymer. It is calculated by dividing the mass of a polymer sample by the moles of nitrogen present in the sample. "MW/N" is the inverse of theoretical capacity, and the calculations are based upon the feed ratio, assuming full reaction of crosslinker and monomer. The lower the molecular weight per nitrogen the higher the theoretical capacity of the crosslinked polymer.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes embodiments in which the heterocyclyl group is substituted with an alkyl group and embodiments in which the heterocyclyl group is not substituted with alkyl.

"Pharmaceutically acceptable" as used in connection with a carrier, diluent or excipient means a carrier, diluent or an excipient, respectively, that is useful in preparing a pharmaceutical composition that is generally safe, non-toxic and neither biologically nor otherwise undesirable for veterinary use and/or human pharmaceutical use.

The term "post polymerization crosslinking" is a term that describes a reaction to an already formed bead or gel, where more crosslinking is introduced to the already formed bead or gel to create a bead or gel that has an increased amount of crosslinking.

The term "post polymerization modification" is a term that describes a modification to an already formed bead or gel, where a reaction or a treatment introduces an additional functionality. This functionality can be linked either covalently or non-covalently to the already formed bead.

The term "quaternized amine assay" ("QAA") describes a method to estimate the amount of quaternary amines present in a given crosslinked polymer sample. This assay measures chloride binding of a crosslinked amine polymer at a pH of 11.5. At this pH, primary, secondary and tertiary amines are not substantially protonated and do not substantially contribute to chloride binding. Therefore, any binding observed under these conditions can be attributed to the presence of permanently charged quaternary amines. The test solution used for QAA assay is 100 mM sodium chloride at a pH of 11.5. The concentration of chloride ions is similar to that in the SGF assay which is used to assess total binding capacity of crosslinked amine polymers. Quaternary amine content as a percentage of total amines present is calculated as follows:

$$\% \text{ Quaternary amines} = \frac{\text{Chloride bound (mmol/g) in } QAA}{\text{Chloride bound (mmol/g) in } SGF} \times 100$$

To perform the QAA assay, the free-amine polymer being tested is prepared at a concentration of 2.5 mg/ml (e.g. 25 mg dry mass) in 10 mL of QAA buffer. The mixture is incubated at 37° C. for ~16 hours with agitation on a rotisserie mixer. After incubation and mixing, 600 microliters of supernatant is removed and filtered using a 800 microliter, 0.45 micrometer pore size, 96-well poly propylene filter plate. With the samples arrayed in the filter plate and the collection plate fitted on the bottom, the unit is centrifuged at 1000×g for 1 minute to filter the samples. After filtration into the collection plate, the respective filtrates are diluted appropriately before measuring for chloride content. The IC method (e.g. ICS-2100 Ion Chromatography, Thermo Fisher Scientific) used for the analysis of chloride content in the filtrates consists of a 15 mM KOH mobile phase, an injection volume of 5 microliters, with a run time of three minutes, a washing/rinse volume of 1000 microliters, and flow rate of 1.25 mL/min. To determine the chloride bound to the polymer, the following calculation is completed:

$$\text{Binding capacity expressed as mmol chloride/g dry polymer} = \frac{(\text{Cl start} - \text{Cl } eq)}{2.5}$$

where Cl start corresponds to the starting concentration of chloride in the QAA buffer, Cl eq corresponds to the equilibrium value of chloride in the measured filtrates after exposure to the test polymer, and 2.5 is the polymer concentration in mg/ml.

"Simulated Gastric Fluid" or "SGF" Assay describes a test to determine total chloride binding capacity for a test polymer using a defined buffer that simulates the contents of gastric fluid as follows: Simulated gastric fluid (SGF) consists of 35 mM NaCl, 63 mM HCl, pH 1.2. To perform the assay, the free-amine polymer being tested is prepared at a concentration of 2.5 mg/ml (25 mg dry mass) in 10 mL of SGF buffer. The mixture is incubated at 37° C. overnight for ~12-16 hours with agitation on a rotisserie mixer. After incubation and mixing, the tubes containing the polymer are centrifuged for 2 minutes at 500-1000×g to pellet the test samples. Approximately 750 microliters of supernatant are removed and filtered using an appropriate filter, for example a 0.45 micrometer pore-size syringe filter or an 800 microliter, 1 micrometer pore-size, 96-well, glass filter plate that has been fitted over a 96-well 2 mL collection plate. With the latter arrangement multiple samples tested in SGF buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL container. After filtration, the respective filtrates are diluted 4× with water and the chloride content of the filtrate is measured via ion chromatography (IC). The IC method (e.g. Dionex ICS-2100, Thermo Scientific) consists of an AS11 column and a 15 mM KOH mobile phase, an injection volume of 5 microliters, with a run time of 3 minutes, a washing/rinse volume of 1000 microliters, and flow rate of 1.25 mL/min. To determine the chloride bound to the polymer, the following calculation is completed:

$$\frac{(\text{Cl start} - \text{Cl } eq) \times 4}{2.5}.$$

Binding capacity expressed as mmol chloride/g polymer: where Cl start corresponds to the starting concentration of chloride in the SGF buffer, Cl eq corresponds to the equilibrium value of chloride in the diluted measured filtrates after exposure to the test polymer, 4 is the dilution factor and 2.5 is the polymer concentration in mg/ml.

"Simulated Small Intestine Inorganic Buffer" or "SIB" is a test to determine the chloride and phosphate binding capacity of free amine test polymers in a selective specific interfering buffer assay (SIB). The chloride and phosphate binding capacity of free amine test polymers, along with the chloride and phosphate binding capacity of free amine sevelamer and bixalomer control polymers, was determined using the selective specific interfering buffer assay (SIB) as follows: The buffer used for the SIB assay comprises 36 mM NaCl, 20 mM NaH$_2$PO$_4$, 50 mM 2-(N-morpholino)ethanesulfonic acid (MES) buffered to pH 5.5. The SIB buffer contains concentrations of chloride, phosphate and pH that are present in the human duodenum and upper gastrointestinal tract (Stevens T, Conwell D L, Zuccaro G, Van Lente F, Khandwala F, Purich E, et al. Electrolyte composition of endoscopically collected duodenal drainage fluid after synthetic porcine secretin stimulation in healthy subjects. Gastrointestinal endoscopy. 2004; 60(3):351-5, Fordtran J, Locklear T. Ionic constituents and osmolality of gastric and small-intestinal fluids after eating. Digest Dis Sci. 1966; 11(7):503-21) and is an effective measure of the selectivity of chloride binding compared to phosphate binding by a polymer. To perform the assay, the free amine polymer being tested is prepared at a concentration of 2.5 mg/ml (25 mg dry mass) in 10 mL of SIB buffer. The mixture is incubated at 37° C. for 1 hour with agitation on a rotisserie mixer. After incubation and mixing, the tubes containing the polymer are centrifuged for 2 minutes at 1000×g to pellet the test samples. 750 microliter of supernatant is removed and filtered using an 800 microliter, 1 micrometer pore-size, 96-well, glass filter plate that has been fitted over a 96-well 2 mL collection plate; with this arrangement multiple samples tested in SIB buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter (0.45 micrometer) may be used in lieu of the filter plate, to retrieve ~2-4 mL of filtrate into a 15 mL vial. After filtration into the collection plate, the respective filtrates are diluted before measuring for chloride or phosphate content. For the measurement of chloride and phosphate, the filtrates under analysis are diluted 4× with water. The chloride and phosphate content of the filtrate is measured via ion chromatography (IC). The IC method (e.g. Dionex ICS-2100, Thermo Scientific) consists of an AS24A column, a 45 mM KOH mobile phase, an injection volume of 5 microliters, with a run time of about 10 minutes, a washing/rinse volume of 1000 microliter, and flow rate of 0.3 mL/min. To determine the chloride bound to the polymer, the following calculation is completed:

Binding capacity expressed as mmol chloride/g polymer =

$$\frac{(\text{Cl}_{start} - \text{Cl}_{final}) \times 4}{2.5}$$

where Cl$_{start}$ corresponds to the starting concentration of chloride in the SIB buffer, Cl$_{final}$ corresponds to the final value of chloride in the measured diluted filtrates after exposure to the test polymer, 4 is the dilution factor and 2.5 is the polymer concentration in mg/ml. To determine the phosphate bound to the polymer, the following calculation is completed:

Binding capacity expressed as mmol phosphate/g polymer =

$$\frac{(\text{P}_{start} - \text{P}_{final}) \times 4}{2.5}$$

where P$_{start}$ corresponds to the starting concentration of phosphate in the SIB buffer, P$_{final}$ corresponds to the final value of phosphate in the measured diluted filtrates after exposure to the test polymer, 4 is the dilution factor and 2.5 is the polymer concentration in mg/ml.

"Simulated Small Intestine Organic and Inorganic Buffer" or "SOB" is a test to determine the chloride binding capacity, measured in the presence of specific organic and inorganic interferents commonly found in the gastrointestinal tract. The chloride binding capacity, as well as the binding capacity for other anions, of free amine test polymers and of free amine sevelamer and bixalomer control polymers, was measured in the presence of specific organic interferents commonly found in the gastrointestinal tract as follows: To mimic the conditions of the GI lumen, the SOB screen is used to determine the chloride binding capacity of free amine polymers when they are exposed to chloride in the presence of other potential competing anions such as bile acid, fatty acid, phosphate, acetate and citrate. The test buffer used for SOB assay comprises 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM Sodium taurocholate, buffered to pH 6.2. The concentrations of potential competing anions reflect typical gastrointestinal lumen concentrations found at various points of the GI tract and the pH is an average value representative of pH values encountered both the duodenum and the large intestine. The chloride concentration used is the same as that used in the SIB screen. To perform the assay, the free amine polymer to be tested is accurately weighed in a 16×100 mm glass tube with a liquid-tight screw cap. An appropriate amount of SOB buffer is added to the test tube to achieve a final polymer concentration of 2.5 mg/ml. The mixture is incubated at 37° C. for 2 hours with agitation on a rotisserie mixer. After incubation and mixing, 600 microliters of supernatant is removed and filtered using a 96-well glass filter plate. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL vial. After filtration into the collection plate, the respective filtrates are diluted appropriately before measuring for anion content. The IC method (e.g. Dionex ICS-2100, Thermo Scientific) consists of an AS24A column, a KOH gradient from 20 mM to 100 mM, an injection volume of 5 microliters, with a run time of about 30 minutes, a washing/rinse volume of 1000 microliters, and flow rate of 0.3 mL/min. This method is suitable for quantitating chloride, phosphate, and taurocholate. Other appropriate methods may be substituted. To determine the ions bound to the polymer, the following calculation is completed Binding capacity expressed as mmol of ion/g polymer =
$$\frac{([Ion]_{start} - [Ion]_{final}) \times [\text{dilution factor}]}{2.5}$$

where $[Ion]_{start}$ corresponds to the starting concentration of an ion in the SOB buffer, $[Ion]_{final}$ corresponds to the final value of that particular ion in the measured filtrates after exposure to the test polymer, dilution factor is the dilution factor and 2.5 is the polymer concentration in mg/ml.

The term "substituted hydrocarbyl," "substituted alkyl," "substituted alkenyl," "substituted aryl," "substituted heterocyclo," or "substituted heteroaryl" as used herein denotes hydrocarbyl, alkyl, alkenyl, aryl, heterocyclo, or heteroaryl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters and ethers.

"Swelling Ratio" or simply "Swelling" describes the amount of water absorbed by a given amount of polymer divided by the weight of the polymer aliquot. The swelling ratio is expressed as: swelling=(g swollen polymer–g dry polymer)/g dry polymer. The method used to determine the swelling ratio for any given polymer comprised the following:
 a. 50-100 mg of dry (less than 5 weight % water content) polymer is placed into an 11 mL sealable test tube (with screw cap) of known weight (weight of tube=Weight A).
 b. Deionized water (10 mL) is added to the tube containing the polymer. The tube is sealed and tumbled for 16 hours (overnight) at room temperature. After incubation, the tube is centrifuged at 3000×g for 3 minutes and the supernatant is carefully removed by vacuum suction. For polymers that form a very loose sediment, another step of centrifugation is performed.
 c. After step (b), the weight of swollen polymer plus tube (Weight B) is recorded.
 d. Freeze at −40° C. for 30 minutes. Lyophilize for 48 h. Weigh dried polymer and test tube (recorded as Weight C).
 e. Calculate g water absorbed per g of polymer, defined as: [(Weight B−Weight A)−(Weight C−Weight A)]/(Weight C−Weight A).

A "target ion" is an ion to which the polymer binds, and usually refers to the major ions bound by the polymer, or the ions whose binding to the polymer is thought to produce the therapeutic effect of the polymer (e.g. proton and chloride binding which leads to net removal of HCl).

The term "theoretical capacity" represents the calculated, expected binding of hydrochloric acid in an "SGF" assay, expressed in mmol/g. The theoretical capacity is based on the assumption that 100% of the amines from the monomer(s) and crosslinker(s) are incorporated in the crosslinked polymer based on their respective feed ratios. Theoretical capacity is thus equal to the concentration of amine functionalities in the polymer (mmol/g). The theoretical capacity assumes that each amine is available to bind the respective anions and cations and is not adjusted for the type of amine formed (e.g. it does not subtract capacity of quaternary amines that are not available to bind proton).

"Therapeutically effective amount" means the amount of a proton-binding crosslinked amine polymer that, when administered to a patient for treating a disease, is sufficient to effect such treatment for the disease. The amount constituting a "therapeutically effective amount" will vary depending on the polymer, the severity of the disease and the age, weight, etc., of the mammal to be treated.

"Treating" or "treatment" of a disease includes (i) inhibiting the disease, i.e., arresting or reducing the development of the disease or its clinical symptoms; or (ii) relieving the disease, i.e., causing regression of the disease or its clinical symptoms. Inhibiting the disease, for example, would include prophylaxis.

The term "triallylamine" denotes an amino moiety having three allyl groups.

The term "vinyl" denotes a moiety having the structural formula $R_xH_yC{=}CH{-}*$, where * denotes the point of attachment of the moiety to the remainder of the molecule wherein the point of attachment is a heteroatom or aryl, X and Y are independently 0, 1 or 2, such that X+Y=2, and R is hydrocarbyl or substituted hydrocarbyl.

The term "weight percent crosslinker" represents the calculated percentage, by mass, of a polymer sample that is derived from the crosslinker. Weight percent crosslinker is calculated using the feed ratio of the polymerization, and assumes full conversion of the monomer and crosslinker(s). The mass attributed to the crosslinker is equal to the expected increase of molecular weight in the infinite polymer network after reaction (e.g. 1,3,-dichloropropane is 113 amu, but only 42 amu are added to a polymer network after crosslinking with DCP because the chlorine atoms, as leaving groups, are not incorporated into the polymer network).

When introducing elements of the present invention or the preferred embodiments(s) thereof, the articles "a", "an", "the" and "said" are intended to mean that there are one or more of the elements. The terms "comprising", "including" and "having" are intended to be inclusive and not exclusive (i.e., there may be other elements in addition to the recited elements).

EMBODIMENTS

As previously noted, among the various aspects of the present disclosure may be noted treatment methods using compositions comprising a nonabsorbed, crosslinked polymer containing free amine moieties. In one embodiment, the crosslinked amine polymers have the capacity to remove clinically significant quantities of protons and chloride ions from the gastrointestinal tract of an animal, including for example humans, upon administration of a therapeutically effective amount (i.e., an effective dose) of the crosslinked amine polymer to achieve a therapeutic or prophylactic benefit.

A therapeutically effective dose of the crosslinked amine polymers disclosed herein will depend, at least in part, on the disease being treated, the capacity of the crosslinked free amine polymer, and the intended effect. In one embodiment, the daily dose of the crosslinked free amine polymer is sufficient to retard the rate of reduction of serum bicarbonate levels over a prolonged period. In another embodiment, the daily dose of the crosslinked free amine polymer is sufficient to maintain serum bicarbonate levels over a prolonged period. In another embodiment, the daily dose of the crosslinked free amine polymer is sufficient to increase serum bicarbonate levels over a prolonged period. For example, in one embodiment, the daily dose is sufficient to achieve or maintain a serum bicarbonate level of at least about 20 mEq/L over a prolonged period. By way of further example, in one such embodiment, the daily dose is sufficient to achieve or maintain a serum bicarbonate level of at least about 21 mEq/L over a prolonged period. By way of further example, in one such embodiment, the daily dose is sufficient to achieve or maintain a serum bicarbonate level of at least about 22 mEq/L over a prolonged period. In yet another embodiment, the daily dose is sufficient to achieve or maintain a serum bicarbonate level of at least about 24 mEq/L over a prolonged period. In each of the foregoing embodiments, a prolonged period is a period of at least one month; for example, at least two months, at least three months, or even at least several months.

In general, the dosage levels of the crosslinked amine polymers for therapeutic and/or prophylactic uses may range from about 0.5 g/day to about 20 g/day. To facilitate patient compliance, it is generally preferred that the dose be in the range of about 1 g/day to about 10 g/day. For example, in one such embodiment, the dose will be about 2 g/day to about 7 g/day. By way of further example, in one such embodiment, the dose will be about 3 g/day to about 6 g/day. By way of further example, in one such embodiment, the dose will be about 4 g/day to about 5 g/day. Optionally, the daily dose may be administered as a single dose (i.e., one time a day), or divided into multiple doses (e.g., two, three or more doses) over the course of a day. In general the crosslinked amine polymers for therapeutic and/or prophylactic uses may be administered as a fixed daily dose or titrated based on the serum bicarbonate values of the patient in need of treatment or other indicators of acidosis. The titration may occur at the onset of treatment or throughout, as required, and starting and maintenance dosage levels may differ from patient to patient based on severity of the underlying disease.

Figure 1B:
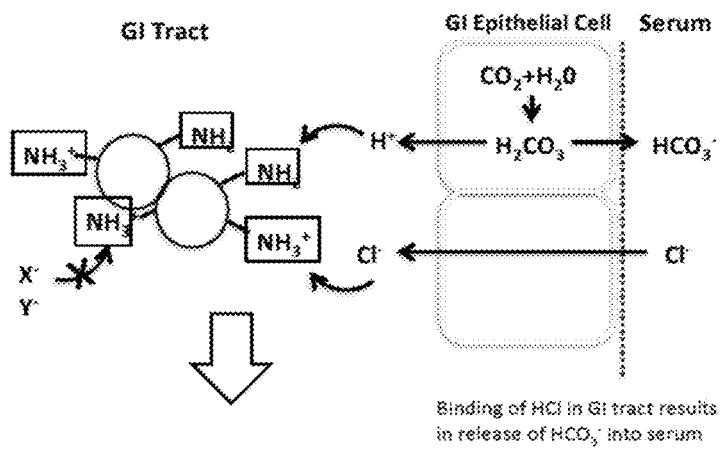
Figure 1C:
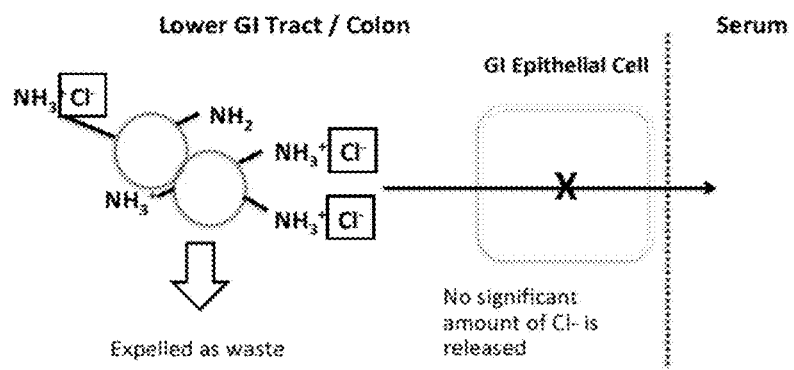

As schematically depicted in FIGS. 1A-1C and in accordance with one embodiment, a non-absorbed, free-amine polymer of the present disclosure is orally ingested and used to treat metabolic acidosis (including by increasing serum bicarbonate and normalizing blood pH) in a mammal by binding HCl in the gastrointestinal ("GI") tract and removing HCl through the feces. Free-amine polymer is taken orally (FIG. 1A) at compliance enhancing dose targeted to chronically bind sufficient amounts of HCl to enable clinically meaningful increase in serum bicarbonate of 3 mEq/L. In the stomach (FIG. 1B), free amine becomes protonated by binding H$^+$. Positive charge on polymer is then available to bind Cl$^-$; by controlling access of binding sites through crosslinking and hydrophilicity/hydrophobicity properties, other larger organic anions (e.g., acetate, propionate, butyrate, etc., depicted as X$^-$ and Y$^-$) are bound to a lesser degree, if at all. The net effect is therefore binding of HCl. In the lower GI tract/colon (FIG. 1C), Cl$^-$ is not released and HCl is removed from the body through regular bowel movement and fecal excretion, resulting in net alkalinization in the serum. Cl$^-$ bound in this fashion is not available for exchange via the Cl$^-$/HCO$_3^-$ antiporter system.

In one embodiment, the polymer is designed to simultaneously maximize efficacy (net HCl binding and excretion) and minimize GI side effects (through low swelling particle design and particle size distribution). Optimized HCl binding may be accomplished through a careful balance of capacity (number of amine binding sites), selectivity (preferred binding of chloride versus other anions, in particular organic anions in the colon) and retention (not releasing significant amounts of chloride in the lower GI tract to avoid the activity of the Cl$^-$/HCO$_3^-$ exchanger [antiporter] in the colon and intestine; if chloride is not tightly bound to the polymer the Cl$^-$/HCO$_3^-$ exchanger can mediate uptake of chloride ion from the intestinal lumen and reciprocal exchange for bicarbonate from the serum, thus effectively decreasing serum bicarbonate.

Competing anions that displace chloride lead to a decrease in net bicarbonate through the following mechanisms. First, displacement of chloride from the polymer in the GI lumen, particularly the colon lumen, provides for a facile exchange with bicarbonate in the serum. The colon has an anion exchanger (chloride/bicarbonate antiporter) that moves chloride from the luminal side in exchange for secreted bicarbonate. When free chloride is released from the polymer in the GI tract it will exchange for bicarbonate, which will then be lost in the stool and cause a reduction in total extracellular bicarbonate (Davis, 1983; D'Agostino, 1953). The binding of short chain fatty acids (SCFA) in exchange for bound chloride on the polymer, will result in the depletion of extracellular HCO3− stores. Short chain fatty acids are the product of bacterial metabolism of complex carbohydrates that are not catabolized by normal digestive processes (Chemlarova, 2007). Short chain fatty acids that reach the colon are absorbed and distributed to various tissues, with the common metabolic fate being the generation of H2O and CO2, which is converted to bicarbonate equivalents. Thus, binding of SCFA to the polymer to neutralize the proton charge would be detrimental to overall bicarbonate stores and buffering capacity, necessitating the design of chemical and physical features in the polymer that limit SCFA exchange. Finally, phosphate binding to the polymer should be limited as well, since phosphate represents an additional source of buffering capacity in the situation where ammoniagenesis and/or hydrogen ion secretion is compromised in chronic renal disease.

For each binding of proton, an anion is preferably bound as the positive charge seeks to leave the human body as a neutral polymer. "Binding" of an ion, is more than minimal binding, i.e., at least about 0.2 mmol of ion/gm of polymer, at least about 1 mmol of ion/gm of polymer in some embodiments, at least about 1.5 mmol of ion/gm of polymer in some embodiments, and at least about 3 mmol of ion/gm of polymer in some embodiments. In one embodiment, the polymers are characterized by their high capacity of proton binding while at the same time providing selectivity for anions; selectivity for chloride is accomplished by reducing the binding of interfering anions that include but are not limited to phosphate, citrate, acetate, bile acids and fatty acids. For example, in some embodiments, polymers of the present disclosure bind phosphate with a binding capacity of less than about 5 mmol/gm, less than about 4 mmol/gm, less than about 3 mmol/gm, less than about 2 mmol/gm or even less than about 1 mmol/gm. In some embodiments, polymers of the invention bind bile and fatty acids with a binding capacity of less than about less than about 5 mmol/g, less than about 4 mmol/g, less than about 3 mmol/g, less than about 2 mmol/gm, less than about 1 mmol/gm in some embodiments, less than about 0.5 mmol/gm in some embodiments, less than about 0.3 mmol/gm in some embodiments, and less than about 0.1 mmol/gm in some embodiments.

The effectiveness of the polymer may be established in animal models, or in human volunteers and patients. In addition, in vitro, ex vivo and in vivo approaches are useful to establish HCl binding. In vitro binding solutions can be used to measure the binding capacity for proton, chloride and other ions at different pHs. Ex vivo extracts, such as the gastrointestinal lumen contents from human volunteers or from model animals can be used for similar purposes. The selectivity of binding and/or retaining certain ions preferentially over others can also be demonstrated in such in vitro and ex vivo solutions. In vivo models of metabolic acidosis can be used to test the effectiveness of the polymer in normalizing acid/base balance—for example 5/6 nephrectomized rats fed casein-containing chow (as described in Phisitkul S, Hacker C, Simoni J, Tran R M, Wesson D E. Dietary protein causes a decline in the glomerular filtration rate of the remnant kidney mediated by metabolic acidosis and endothelin receptors. Kidney international. 2008; 73(2): 192-9).

In one embodiment, the polymers described in the current disclosure are provided to an animal, including a human, in once, twice or three times a day dosing most preferably not exceeding a daily dose of 5 g or less per day) to treat metabolic acidosis and achieve a clinically significant and sustained increase of serum bicarbonate of approximately 3 mEq/L at these daily doses. The amount of HCl binding achieved by oral administration of the polymer is determined by the polymer binding capacity, which is generally in the range of 5-25 mEq of HCl per 1 g of polymer. Additionally, the polymer is preferably selective in terms of the anion that is bound to counterbalance the proton binding, with chloride being the preferred anion. Anions other than chloride, bound to neutralize the proton positive charge, include phosphate, short chain fatty acids, long chain fatty acids, bile acids or other organic or inorganic anions. Binding of these anions, other than chloride, influences overall bicarbonate stores in the intracellular and extracellular compartments.

In one embodiment, the mechanism of action for the HCl polymeric binder comprises the following. In the stomach or elsewhere in the GI tract, the free amine polymer becomes protonated by binding proton ($H^+$). The positive charge formed as a result of this binding is then available for chloride anion binding. After exiting the stomach, the polymer sequentially encounters different GI tract environments in the order duodenum, jejunum, ileum and colon, each with a complement of distinct organic and inorganic anions. Physical and chemical properties of the polymer are designed to control access of protonated binding sites to this collection of anions. Physical barriers include crosslinking (size exclusion to prevent anion binding) and chemical moieties (to repel larger, organic ions such as acetate, propionate, butyrate or other short chain fatty acids commonly present in the colon), and combinations of the two properties to limit phosphate, bile acid and fatty acid binding. By tailoring the bead crosslinking and the chemical nature of the amine binding sites, chloride can be bound tightly so that exchange for other anions and release in the lower GI tract is reduced or eliminated. Without being bound by theory, anions with a larger ionic and/or hydration radius than chloride can be excluded, or their binding reduced, by incorporating these properties into the HCl binding polymer. For example, the ionic radius of chloride, either in the hydrated or unhydrated form is smaller than the corresponding values for phosphate and other anions commonly encountered in the GI tract lumen (Supramolecular Chemistry, Steed, J W (2009) John Wiley and Sons, page 226; Kielland, J (1937), J. Am. Chem. Soc. 59:1675-1678). To selectively bind smaller ions, polymers typically display high crosslinking densities in order to create preferential access to the polymer binding sites. High crosslinking density materials are, however, typically characterized by low swelling ratios. The swelling ratio, can be affected by the following composition and process variables: 1) the molar ratio of amine monomer (or polymer) and crosslinker, 2) the monomer+crosslinker to solvent ratio in the crosslinking reaction, 3) the net charge of the polymer (at the physiological pH and tonicity of the milieu in which it will be used), 4) the hydrophilic/hydrophobic balance of the backbone polymer and/or 5) post-crosslinking of an existing material.

Figure 2:
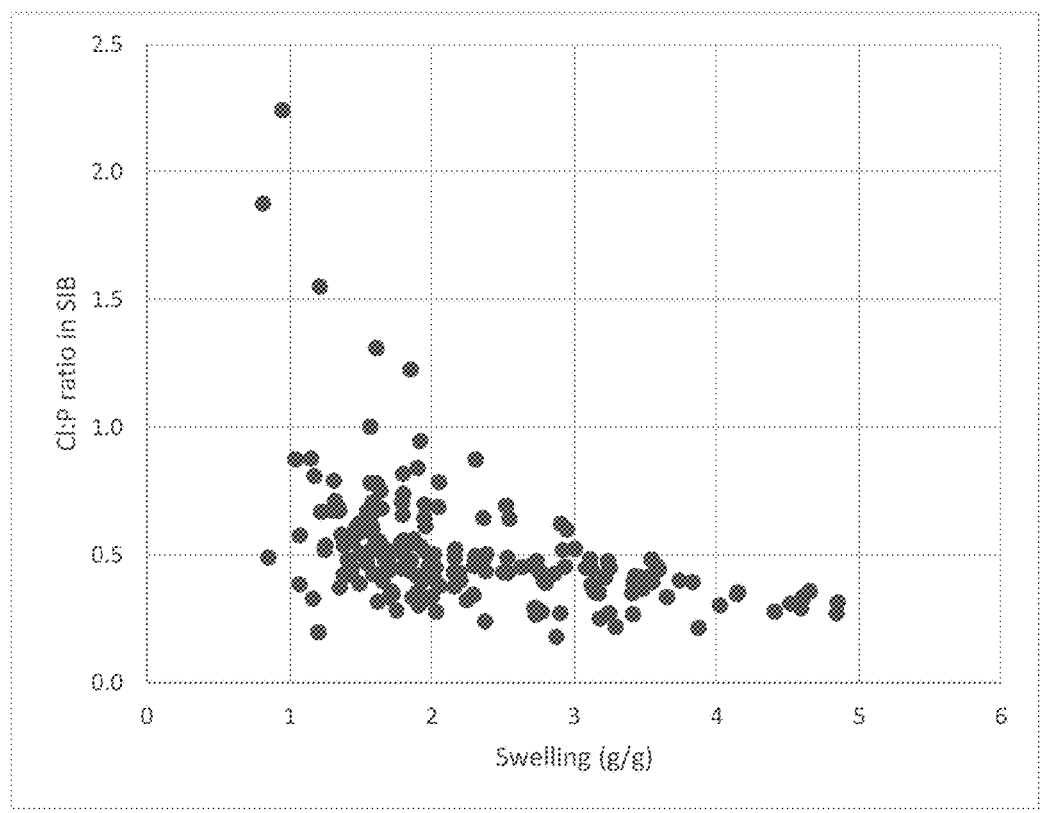
FIG. 2 is Is a graph of the relationship between swelling ratios of polymers of the current disclosure versus the chloride:phosphate binding ratio in SIB.

In general, a crosslinked amine polymer of the present disclosure is typically characterized by a low swelling ratio. In one embodiment, the relative chloride binding to phosphate binding ratio in SIB is an indicator of the selectivity of the crosslinked polymers of the current disclosure for chloride versus larger anions. A graph of the relationship between swelling ratios for certain polymers of the current disclosure versus the chloride:phosphate binding ratio in SIB is shown in FIG. 2. For example, in one embodiment, a polymer of the current disclosure has a chloride to phosphate binding ratio in SIB of $\geq 0.35$ and a swelling ratio of $\leq 2$ g water per g of dry polymer. By way of further example, in one embodiment a polymer of the current disclosure has a chloride to phosphate binding ratio in SIB of $\geq 0.5$ and a swelling ratio of $\leq 2$ g water per g of dry polymer. By way of further example, in one embodiment a polymer of the current disclosure has a chloride to phosphate binding ratio in SIB of $\geq 1$ and a swelling ratio of $\leq 2$ g water per g of dry polymer. By way of further example, in one embodiment a polymer of the current disclosure has a chloride to phosphate binding ratio in SIB of $\geq 2$ and a swelling ratio of $\leq 2$ g water per g of dry polymer. By way of further example, in one embodiment a polymer of the current disclosure has a chloride to phosphate binding ratio in SIB of $\geq 0.35$ and a swelling ratio of $\leq 1$ g water per g of dry polymer. By way of further example, in one embodiment a polymer of the current disclosure has a chloride to phosphate binding ratio in SIB of $\geq 0.5$ and a swelling ratio of $\leq 1$ g water per g of dry polymer. By way of further example, in one embodiment a polymer of the current disclosure has a chloride to phosphate binding ratio in SIB of $\geq 1$ and a swelling ratio of $\leq 1$ g water per g of dry polymer. By way of further example, in one embodiment a polymer of the current disclosure has a chloride to phosphate binding ratio in SIB of $\geq 2$ and a swelling ratio of $\leq 1$ g water per g of dry polymer.

In some embodiments, a crosslinked amine polymer of the current disclosure versus the chloride:phosphate binding ratio in SIB is shown in FIG. 2. For example, in one embodiment a polymer of the current disclosure has a chloride binding capacity in SGF of $\geq 10$ mmol/g and a swelling ratio of $\leq 2$ g water per g of dry polymer. By way of further example, in one embodiment a polymer of the current disclosure has a chloride binding capacity in SGF of $\geq 12$ mmol/g and a swelling ratio of $\leq 2$ g water per g of dry polymer. By way of further example, in one embodiment a polymer of the current disclosure has a chloride binding capacity in SGF of $\geq 14$ mmol/g and a swelling ratio of $\leq 2$ g water per g of dry polymer. By way of further example, in one embodiment a polymer of the current disclosure has a chloride binding capacity in SGF of ≥10 mmol/g and a swelling ratio of ≤1.5 g water per g of dry polymer. By way of further example, in one embodiment a polymer of the current disclosure has a chloride binding capacity in SGF of ≥12 mmol/g and a swelling ratio of ≤1.5 g water per g of dry polymer. By way of further example, in one embodiment a polymer of the current disclosure has a chloride binding capacity in SGF of ≥14 mmol/g and a swelling ratio of ≤1.5 g water per g of dry polymer.

In some embodiments, the theoretical chloride binding capacity of the polymers of the present disclosure may range from about 1 mmol/g to about 25 mmol/g. In one embodiment, the theoretical chloride binding capacity of the polymer is about 3 mmol/g to about 25 mmol/g. In another embodiment, the theoretical chloride binding capacity of the polymer is about 6 mmol/g to about 20 mmol/g. In another embodiment, the theoretical chloride binding capacity of the polymer about 9 mmol/g to about 17 mmol/g.

In some embodiments, the molecular weight per nitrogen of the polymers of the present disclosure may range from about 40 to about 1000 daltons. In one embodiment, the molecular weight per nitrogen of the polymer is from about 40 to about 500 daltons. In another embodiment, the molecular weight per nitrogen of the polymer is from about 50 to about 170 daltons. In another embodiment, the molecular weight per nitrogen of the polymer is from about 60 to about 110 daltons.

In some embodiments, the crosslinker weight % range will be about 10 to 90 weight % of the crosslinked amine polymer. For example, in some embodiments the crosslinker weight % range will be about 15 to 90 weight % of the crosslinked amine polymer or even about 25 to 90 weight % of the crosslinked amine polymer.

The crosslinked amine polymers may be prepared using a range of chemistries, including for example, (i) substitution polymerization of polyfunctional reagents at least one of which comprises amine moieties, (2) radical polymerization of a monomer comprising at least one amine moiety or nitrogen containing moiety, and (3) crosslinking of an amine-containing intermediate with a polyfunctional crosslinker, optionally containing amine moieties. The resulting crosslinked polymers may thus, for example, be crosslinked homopolymers or crosslinked copolymers. By way of further example, the resulting crosslinked polymers will typically possess repeat units comprising free amine moieties, separated by the same or varying lengths of repeating linker (or intervening) units. In some embodiments, the polymers comprise repeat units comprising an amine moiety and an intervening linker unit. In other embodiments, multiple amine-containing repeat units are separated by one or more linker units. Additionally, the polyfunctional crosslinkers may comprise HCl binding functional groups, e.g. amines, ("active crosslinkers") or may lack HCl binding functional groups such as amines ("passive crosslinkers").

In some embodiments, an amine-containing monomer is polymerized and the polymer is concurrently crosslinked in a substitution polymerization reaction. The amine reactant (monomer) in the concurrent polymerization and crosslinking reaction can react more than one time for the substitution polymerization. In one such embodiment, the amine monomer is a linear amine possessing at least two reactive amine moieties to participate in the substitution polymerization reaction. In another embodiment, the amine monomer is a branched amine possessing at least two reactive amine moieties to participate in the substitution polymerization reaction. Crosslinkers for the concurrent substitution polymerization and crosslinking typically have at least two amine-reactive moieties such as alkyl-chlorides, and alkyl-epoxides. In order to be incorporated into the polymer, primary amines react at least once and potentially may react up to three times with the crosslinker, secondary amines can react up to twice with the crosslinkers, and tertiary amines can only react once with the crosslinker. In general, however, and in accordance with one aspect of the present disclosure, the formation of a significant number of quaternary nitrogens/amines is generally not preferred because quaternary amines cannot bind protons.

Exemplary amines that may be used in substitution polymerization reactions described herein include 1,3-Bis[bis(2-aminoethyl)amino]propane, 3-Amino-1-{[2-(bis{2-[bis(3-aminopropyl)amino]ethyl}amino)ethyl](3-aminopropyl)amino}propane, 2-[Bis(2-aminoethyl)amino]ethanamine, Tris(3-aminopropyl)amine, 1,4-Bis[bis(3-aminopropyl)amino]butane, 1,2-Ethanediamine, 2-Amino-1-(2-aminoethylamino)ethane, 1,2-Bis(2-aminoethylamino)ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl)ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, 3-(Methylamino)pyrrolidine Exemplary crosslinking agents that may be used in substitution polymerization reactions and post-polymerization crosslinking reactions include include, but are not limited to, one or more multifunctional crosslinking agents such as: dihaloalkanes, haloalkyloxiranes, alkyloxirane sulfonates, di(haloalkyl)amines, tri(haloalkyl) amines, diepoxides, triepoxides, tetraepoxides, bis (halomethyl)benzenes, tri(halomethyl)benzenes, tetra(halomethyl)benzenes, epihalohydrins such as epichlorohydrin and epibromohydrin poly (epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy) diphenylmethane, bisphenol F diglycidyl ether, 1,4-bis(2',3'epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl) tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo [7,3,3,15,11]heptasiloxane, 4,4'methylenebis(N,N-diglycidylaniline), bis(halomethyl)benzene, bis(halomethyl)biphenyl and bis(halomethyl)naphthalene, toluene diisocyanate, acrylol chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino)ethane, Bis(3-chloropropyl)amine, 1,3-Dichloro-2-propanol, 1,3-Dichloropropane, 1-chloro-2,3-epoxypropane, tris[(2-oxiranyl)methyl]amine.

For the radical polymerization, the amine monomer will typically be a mono-functional vinyl, allyl, or acrylamide (e.g., allylamine) and crosslinkers will have two or more vinyl, allyl or acrylamide functionalities (e.g., diallylamine). Concurrent polymerization and crosslinking occurs through radically initiated polymerization of a mixture of the mono- and multifunctional allylamines. The resulting polymer network is thusly crosslinked through the carbon backbone. Each crosslinking reaction forms a carbon-carbon bond (as opposed to substitution reactions in which a carbon-heteroatom bond is formed during crosslinking). During the concurrent polymerization and crosslinking, the amine functionalities of the monomers do not undergo crosslinking reactions and are preserved in the final polymer (i.e., primary amines remain primary, secondary amines remain secondary, and tertiary amines remain tertiary).

In those embodiments in which the preparation of the polymers comprises radical polymerization, a wide range of initiators may be used including cationic and radical initiators. Some examples of suitable initiators that may be used include: the free radical peroxy and azo type compounds, such as azodiisobutyronitrile, azodiisovaleronitrile, dimethylazodiisobutyrate, 2,2'azo bis(isobutyronitrile), 2,2'-azobis(N,N'-dimethyl-eneisobutyramidine)dihydrochloride, 2,2'-azobis(2-am idinopropane)dihydrochloride, 2,2'-azobis(N, N'-dimethyleneisobutyramidine), 1,1'-azo bis(I-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxypivalates, dodecylbenzene peroxide, benzoyl peroxide, di-t-butyl hydroperoxide, t-butyl peracetate, acetyl peroxide, dicumyl peroxide, cumylhydroperoxide, dimethyl bis(butylperoxy)hexane.

In some embodiments, the crosslinked amine polymer comprises the residue of an amine corresponding to Formula 1:

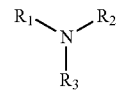

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen. Stated differently, at least one of $R_1$, $R_2$ and $R_3$ is hydrocarbyl or substituted hydrocarbyl, and the others of $R_1$, $R_2$ and $R_3$ are independently hydrogen, hydrocarbyl, or substituted hydrocarbyl. In one embodiment, for example, $R_1$, $R_2$ and $R_3$ are independently hydrogen, aryl, aliphatic, heteroaryl, or heteroaliphatic provided, however, each of $R_1$, $R_2$ and $R_3$ are not hydrogen. By way of further example, in one such embodiment $R_1$, $R_2$ and $R_3$ are independently hydrogen, saturated hydrocarbons, unsaturated aliphatic, unsaturated heteroaliphatic, heteroalkyl, heterocyclic, aryl or heteroaryl, provided, however, each of $R_1$, $R_2$ and $R_3$ are not hydrogen. By way of further example, in one such embodiment $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ are not hydrogen. By way of further example, in one such embodiment $R_1$, $R_2$ and $R_3$ are independently hydrogen, alkyl, aminoalkyl, alkanol, aryl, haloalkyl, hydroxyalkyl, ethereal, heteroaryl or heterocyclic provided, however, each of $R_1$, $R_2$ and $R_3$ are not hydrogen. By way of further example, in one such embodiment $R_1$ and $R_2$ (in combination with the nitrogen atom to which they are attached) together constitute part of a ring structure, so that the monomer as described by Formula 1 is a nitrogen-containing heterocycle (e.g., piperidine) and $R_3$ is hydrogen, or heteroaliphatic. By way of further example, in one embodiment $R_1$, $R_2$ and $R_3$ are independently hydrogen, aliphatic or heteroaliphatic provided, however, at least one of $R_1$, $R_2$ and $R_3$ is other than hydrogen. By way of further example, in one embodiment $R_1$, $R_2$ and $R_3$ are independently hydrogen, allyl, or aminoalkyl.

In one embodiment, the crosslinked amine polymer comprises the residue of an amine corresponding to Formula 1 wherein $R_1$, $R_2$, and $R_3$ are independently hydrogen, heteroaryl, aryl, aliphatic or heteroaliphatic provided, however, at least one of $R_1$, $R_2$, and $R_3$ is aryl or heteroaryl. For example, in this embodiment $R_1$ and $R_2$, in combination with the nitrogen atom to which they are attached, may form a saturated or unsaturated nitrogen-containing heterocyclic ring. By way of further example, $R_1$ and $R_2$, in combination with the nitrogen atom to which they are attached may constitute part of a pyrrolidino, pyrole, pyrazolidine, pyrazole, imidazolidine, imidazole, piperidine, pyridine, piperazine, diazine, or triazine ring structure. By way of further example, $R_1$ and $R_2$, in combination with the nitrogen atom to which they are attached may constitute part of a piperidine ring structure.

In one embodiment, the crosslinked amine polymer comprises the residue of an amine corresponding to Formula 1 wherein $R_1$, $R_2$, and $R_3$ are independently hydrogen, aliphatic, or heteroaliphatic provided, however, at least one of $R_1$, $R_2$, and $R_3$ is other than hydrogen. For example, in this embodiment $R_1$, $R_2$, and $R_3$ may independently be hydrogen, alkyl, alkenyl, allyl, vinyl, aminoalkyl, alkanol, haloalkyl, hydroxyalkyl, ethereal, or heterocyclic provided, however, at least one of $R_1$, $R_2$, and $R_3$ is other than hydrogen. By way of further example, in one such embodiment $R_1$ and $R_2$, in combination with the nitrogen atom to which they are attached, may form a saturated or unsaturated nitrogen-containing heterocyclic ring. By way of further example, in one such embodiment $R_1$ and $R_2$, in combination with the nitrogen atom to which they are attached may constitute part of a pyrrolidino, pyrole, pyrazolidine, pyrazole, imidazolidine, imidazole, piperidine, piperazine, or diazine ring structure. By way of further example, in one such embodiment $R_1$ and $R_2$, in combination with the nitrogen atom to which they are attached may constitute part of a piperidine ring structure. By way of further example, in one such embodiment the amine corresponding to Formula 1 is acyclic and at least one of $R_1$, $R_2$, and $R_3$ is aliphatic or heteroaliphatic. By way of further example, in one such embodiment $R_1$, $R_2$, and $R_3$ are independently hydrogen, alkyl, allyl, vinyl, alicyclic, aminoalkyl, alkanol, or heterocyclic, provided at least one of $R_1$, $R_2$, and $R_3$ is other than hydrogen.

In one embodiment, the crosslinked amine polymer comprises the residue of an amine corresponding to Formula 1 and the crosslinked amine polymer is prepared by substitution polymerization of the amine corresponding to Formula 1 with a polyfunctional crosslinker (optionally also comprising amine moieties) wherein $R_1$, $R_2$, and $R_3$ are independently hydrogen, alkyl, aminoalkyl, or alkanol, provided at least one of $R_1$, $R_2$, and $R_3$ is other than hydrogen.

In some embodiments, the crosslinked amine polymer comprises the residue of an amine corresponding to Formula 1a and the crosslinked amine polymer is prepared by radical polymerization of an amine corresponding to Formula 1a:

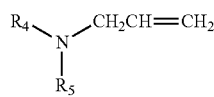

Formula 1a wherein $R_4$ and $R_5$ are independently hydrogen, hydrocarbyl, or substituted hydrocarbyl. In one embodiment, for example, $R_4$ and $R_5$ are independently hydrogen, saturated hydrocarbon, unsaturated aliphatic, aryl, heteroaryl, unsaturated heteroaliphatic, heterocyclic, or heteroalkyl. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl.

In some embodiments, the crosslinked amine polymer comprises the residue of an amine corresponding to Formula 1 b and the crosslinked amine polymer is prepared by substitution polymerization of the amine corresponding to Formula 1b with a polyfunctional crosslinker (optionally also comprising amine moieties):

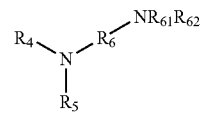

Formula 1b wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic. In one embodiment, for example, $R_4$ and $R_5$ are independently hydrogen, saturated hydrocarbon, unsaturated aliphatic, aryl, heteroaryl, heteroalkyl, or unsaturated heteroaliphatic. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, alkenyl, aminoalkyl, alkanol, aryl, haloalkyl, hydroxyalkyl, ethereal, heteroaryl or heterocyclic. By way of further example, in one such embodiment $R_4$ and $R_5$ (in combination with the nitrogen atom to which they are attached) together constitute part of a ring structure, so that the monomer as described by Formula 1a is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, allyl, or aminoalkyl. By way of further example, in each of the embodiments recited in this paragraph, $R_6$ may be methylene, ethylene or propylene, and $R_{61}$ and $R_{62}$ may independently be hydrogen, allyl or aminoalkyl.

In some embodiments, the crosslinked amine polymer comprises the residue of an amine corresponding to Formula 1c:

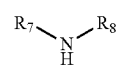

Formula 1c wherein $R_7$ is hydrogen, aliphatic or heteroaliphatic and $R_8$ is aliphatic or heteroaliphatic. For example, in one such embodiment, for example, $R_7$ is hydrogen and $R_8$ is aliphatic or heteroaliphatic. By way of further example, in one such embodiment $R_7$ and $R_8$ are independently aliphatic or heteroaliphatic. By way of further example, in one such embodiment at least one of $R_7$ and $R_8$ comprises an allyl moiety. By way of further example, in one such embodiment at least one of $R_7$ and $R_8$ comprises an aminoalkyl moiety. By way of further example, in one such embodiment $R_7$ and $R_8$ each comprise an allyl moiety. By way of further example, in one such embodiment $R_7$ and $R_8$ each comprise an aminoalkyl moiety. By way of further example, in one such embodiment $R_7$ comprises an allyl moiety and $R_8$ comprises an aminoalkyl moiety.

In some embodiments, the crosslinked amine polymer comprises the residue of an amine corresponding to Formula 2:

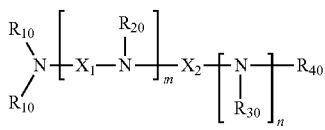

Formula 2 wherein m and n are independently non-negative integers;

$R_{10}$, $R_{20}$, $R_{30}$, and $R_{40}$ are independently hydrogen, hydrocarbyl, or substituted hydrocarbyl;

$X_1$ is

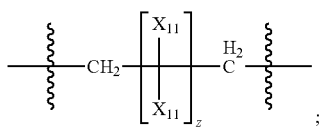

;

$X_2$ is hydrocarbyl or substituted hydrocarbyl;

each $X_{11}$ is independently hydrogen, hydrocarbyl, substituted hydrocarbyl, hydroxyl, amino, boronic acid, or halo; and z is a non-negative number.

In one embodiment, the crosslinked amine polymer comprises the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently 0, 1, 2 or 3 and n is 0 or 1.

In one embodiment, the crosslinked amine polymer comprises the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and $R_{10}$, $R_{20}$, $R_{30}$, and $R_{40}$ are independently hydrogen, aliphatic, aryl, heteroaliphatic, or heteroaryl. By way of further example, in one such embodiment $R_{10}$, $R_{20}$, $R_{30}$, and $R_{40}$ are independently hydrogen, aliphatic, or heteroaliphatic. By way of further example, in one such embodiment $R_{10}$, $R_{20}$, $R_{30}$, and $R_{40}$ are independently hydrogen, alkyl, allyl, vinyl, or aminoalkyl. By way of further example, in one such embodiment $R_{10}$, $R_{20}$, $R_{30}$, and $R_{40}$ are independently hydrogen, alkyl, allyl, vinyl, —$(CH_2)_d NH_2$, —$(CH_2)_d [(CH_2)_e NH_2)]_2$ where d and e are independently 2-4. In each of the foregoing exemplary embodiments of this paragraph, m and z may independently be 0, 1, 2 or 3 and n is 0 or 1.

In one embodiment, the crosslinked amine polymer comprises the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and $X_2$ is aliphatic or heteroaliphatic. For example, in one such embodiment $X_2$ is aliphatic or heteroaliphatic and $R_{10}$, $R_{20}$, $R_{30}$, and $R_{40}$ are independently hydrogen, aliphatic, heteroaliphatic. By way of further example, in one such embodiment $X_2$ is alkyl or aminoalkyl and $R_{10}$, $R_{20}$, $R_{30}$, and $R_{40}$ are independently hydrogen, aliphatic, or heteroaliphatic. By way of further example, in one such embodiment $X_2$ is alkyl or aminoalkyl and $R_{10}$, $R_{20}$, $R_{30}$, and $R_{40}$ are independently hydrogen, alkyl, allyl, vinyl, or aminoalkyl. In each of the foregoing exemplary embodiments of this paragraph, m and z may independently be 0, 1, 2 or 3 and n is 0 or 1.

In one embodiment, the crosslinked amine polymer comprises the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and m is a positive integer. For example, in one such embodiment m is a positive integer, z is zero and $R_{20}$ is hydrogen, aliphatic or heteroaliphatic. By way of further example, in one such embodiment m is a positive integer (e.g., 1 to 3), z is a positive integer (e.g., 1 to 2), $X_{11}$ is hydrogen, aliphatic or heteroaliphatic, and $R_{20}$ is hydrogen, aliphatic or heteroaliphatic. By way of further example, in one such embodiment m is a positive integer, z is zero, one or two, $X_{11}$ is hydrogen alkyl, alkenyl, or aminoalkyl, and $R_{20}$ is hydrogen, alkyl, alkenyl, or aminoalkyl.

In one embodiment, the crosslinked amine polymer comprises the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and n is a positive integer and $R_{30}$ is hydrogen, aliphatic or heteroaliphatic. By way of further example, in one such embodiment n is 0 or 1, and $R_{30}$ is hydrogen, alkyl, alkenyl, or aminoalkyl.

In one embodiment, the crosslinked amine polymer comprises the residue of an amine corresponding to Formula 2, the crosslinked amine polymer is prepared by (i) substitution polymerization of the amine corresponding to Formula 2 with a polyfunctional crosslinker (optionally also comprising amine moieties) or (2) radical polymerization of an amine corresponding to Formula 2, and m and n are independently non-negative integers and $X_2$ is aliphatic or heteroaliphatic. For example, in one such embodiment m is 0 to 2, n is 0 or 1, $X_2$ is aliphatic or heteroaliphatic, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, aliphatic, or heteroaliphatic. By way of further example, in one such embodiment m is 0 to 2, n is 0 or 1, $X_2$ is alkyl or aminoalkyl, and $R_{10}$, $R_{20}$, $R_{30}$, and $R_{40}$ are independently hydrogen, alkyl, alkenyl, or aminoalkyl.

In some embodiments, the crosslinked amine polymer comprises the residue of an amine corresponding to Formula 2a and the crosslinked amine polymer is prepared by substitution polymerization of the amine corresponding to Formula 2a with a polyfunctional crosslinker (optionally also comprising amine moieties):

Formula 2a

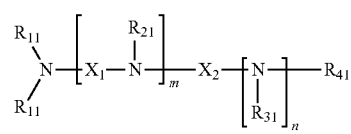

wherein
m and n are independently non-negative integers;
each $R_{11}$ is independently hydrogen, hydrocarbyl, heteroaliphatic, or heteroaryl;
$R_{21}$ and $R_{31}$, are independently hydrogen or heteroaliphatic;
$R_{41}$ is hydrogen, substituted hydrocarbyl, or hydrocarbyl;
$X_1$ is

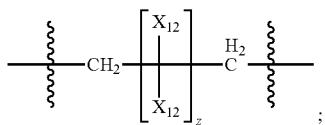

$X_2$ is alkyl or substituted hydrocarbyl;
each $X_{12}$ is independently hydrogen, hydroxy, amino, aminoalkyl, boronic acid or halo; and
z is a non-negative number.

In one embodiment, the crosslinked amine polymer comprises the residue of an amine corresponding to Formula 2a, the crosslinked amine polymer is prepared by substitution polymerization of the amine corresponding to Formula 1 with a polyfunctional crosslinker (optionally also comprising amine moieties). For example, in one such embodiment, m and z are independently 0, 1, 2 or 3, and n is 0 or 1.

In one embodiment, the crosslinked amine polymer comprises the residue of an amine corresponding to Formula 2a, the crosslinked amine polymer is prepared by substitution polymerization of the amine corresponding to Formula 2a with a polyfunctional crosslinker (optionally also comprising amine moieties), and each $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl. For example, in one such embodiment each $R_{11}$ is hydrogen, aliphatic, aminoalkyl, or haloalkyl, $R_{21}$ and $R_{31}$ are independently hydrogen or heteroaliphatic and $R_{41}$ is hydrogen, alkylamino, aminoalkyl, aliphatic, or heteroaliphatic. By way of further example, in one such embodiment each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic. By way of further example, in one such embodiment each $R_{11}$ and $R_{41}$ is independently hydrogen, alkyl, or aminoalkyl, and $R_{21}$ and $R_{31}$ are independently hydrogen or heteroaliphatic. By way of further example, in one such embodiment each $R_{11}$ and $R_{41}$ is independently hydrogen, alkyl, —$(CH_2)_d NH_2$, —$(CH_2)_d N[(CH_2)_e NH_2)]_2$ where d and e are independently 2-4, and $R_{21}$ and $R_{31}$ are independently hydrogen or heteroaliphatic. In each of the foregoing exemplary embodiments of this paragraph, m and z may independently be 0, 1, 2 or 3, and n is 0 or 1.

Exemplary amines for the synthesis of polymers comprising repeat units corresponding to Formula 2a include, but are not limited to, amines appearing in Table 1.

TABLE 1

| Abbreviation | IUPAC name | Other names | | MW (g/mol) |
|---|---|---|---|---|
| C2A3BTA | 1,3-Bis[bis(2-aminoethyl)amino]propane | | | 288.48 |
| C2A3G2 | 3-Amino-1-{[2-(bis{2-[bis(3-aminopropyl)amino]ethyl}amino)ethyl](3-aminopropyl)amino}propane | | | 488.81 |

TABLE 1-continued

| Abbreviation | IUPAC name | Other names | | MW (g/mol) |
|---|---|---|---|---|
| C2PW | 2-[Bis(2-aminoethyl)amino]ethanamine | 2,2',2''-Triaminotriethylamine or 2,2',2''-Nitrilotriethylamine | (structure) | 146.24 |
| C3PW | Tris(3-aminopropyl)amine | | (structure) | 188.32 |
| C4A3BTA | 1,4-Bis[bis(3-aminopropyl)amino]butane | | (structure) | 316.54 |
| EDA1 | 1,2-Ethanediamine | | (structure) | 60.1 |
| EDA2 | 2-Amino-1-(2-aminoethylamino)ethane | Bis(2-aminoethyl)amine or 2,2'-Diaminodiethylamine | (structure) | 103.17 |
| EDA3 | 1,2-Bis(2-aminoethylamino)ethane | N,N'-Bis(2-aminoethyl)ethane-1,2-diamine | (structure) | 146.24 |
| PDA1 | 1,3-Propanediamine | | (structure) | 74.3 |
| PDA2 | 3,3'-Diaminodipropylamine | | (structure) | 131.22 |

Exemplary crosslinkers for the synthesis of polymers comprising the residue of amines corresponding to Formula 2a include but are not limited to crosslinkers appearing in Table 2.

$X_2$ is alkyl, aminoalkyl, or alkanol;

each $X_{13}$ is independently hydrogen, hydroxy, alicyclic, amino, aminoalkyl, halogen, alkyl, heteroaryl, boronic acid or aryl;

TABLE 2

| Abbreviation | Common name | IUPAC name | | MW (g/mol) |
|---|---|---|---|---|
| BCPA | Bis(3-chloropropyl)amine | Bis(3-chloropropyl)amine | Cl~~~N(H)~~~Cl · HCl | 206.54 |
| DC2OH | 1,3-dichloroisopropanol | 1,3-Dichloro-2-propanol | Cl~~~CH(OH)~~~Cl | 128.98 |
| DCP | Dichloropropane | 1,3-Dichloropropane | Cl~~~Cl | 112.98 |
| ECH | Epichlorohydrin | 1-chloro-2,3-epoxypropane | epoxide-CH2-Cl | 92.52 |
| TGA | Triglycidyl amine | Tris[(2-oxiranyl)methyl]amine | tri-epoxide amine | 185.22 |
| BCPOH | Bis(3-chloropropyl) amine-OH | 3-Chloro-1-(3-chloropropylamino)-2-propanol | Cl~~~N(H)~~~CH(OH)~~~Cl | 186.08 |
| BCPEDA | Bis(chloropropyl) ethylenediamine | 1,2-Bis(3-chloropropylamino)ethane | Cl~~~NH~~~CH2CH2~~~NH~~~Cl | 213.15 |

In some embodiments, the crosslinked amine polymer comprises the residue of an amine corresponding to Formula 2b and the crosslinked amine polymer is prepared by radical polymerization of an amine corresponding to Formula 2b:

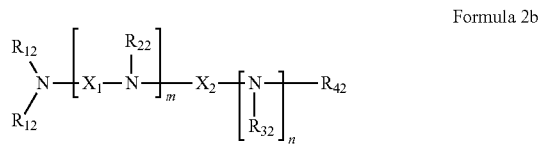

Formula 2b wherein m and n are independently non-negative integers;

each $R_{12}$ is independently hydrogen, substituted hydrocarbyl, or hydrocarbyl;

$R_{22}$ and $R_{32}$ are independently hydrogen substituted hydrocarbyl, or hydrocarbyl;

$R_{42}$ is hydrogen, hydrocarbyl or substituted hydrocarbyl;

$X_1$ is

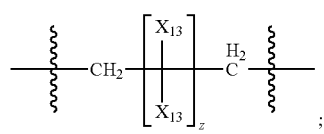

z is a non-negative number, and the amine corresponding to Formula 2b comprises at least one allyl group.

In one embodiment, the crosslinked amine polymer comprises the residue of an amine corresponding to Formula 2b, the crosslinked amine polymer is prepared by radical polymerization of an amine corresponding to Formula 2b, and m and z are independently 0, 1, 2 or 3, and n is 0 or 1.

In one embodiment, the crosslinked amine polymer comprises the residue of an amine corresponding to Formula 2b, the crosslinked amine polymer is prepared by radical polymerization of an amine corresponding to Formula 1, and (i) $R_{12}$ or $R_{42}$ independently comprise at least one allyl or vinyl moiety, (ii) m is a positive integer and $R_{22}$ comprises at least one allyl or vinyl moiety, and/or (iii) n is a positive integer and $R_{32}$ comprises at least one allyl moiety. For example, in one such embodiment, m and z are independently 0, 1, 2 or 3 and n is 0 or 1. For example, in one such embodiment $R_{12}$ or $R_{42}$, in combination comprise at least two allyl or vinyl moieties. By way of further example, in in one such embodiment, m is a positive integer and $R_{12}$, $R_{22}$ and $R_{42}$, in combination comprise at least two allyl or vinyl moieties. By way of further example, in in one such embodiment, n is a positive integer and $R_{12}$, $R_{32}$ and $R_{42}$, in combination comprise at least two allyl or vinyl moieties. By way of further example, in in one such embodiment, m is a positive integer, n is a positive integer and $R_{12}$, $R_{22}$, $R_{32}$ and $R_{42}$, in combination, comprise at least two allyl or vinyl moieties.

In one embodiment, the crosslinked amine polymer comprises the residue of an amine corresponding to Formula 2b, the crosslinked amine polymer is prepared by radical polymerization of an amine corresponding to Formula 2b, and each $R_{12}$ is independently hydrogen, aminoalkyl, allyl, or vinyl, $R_{22}$ and $R_{32}$ are independently hydrogen, alkyl, aminoalkyl, haloalkyl, alkenyl, alkanol, heteroaryl, alicyclic heterocyclic, or aryl, and $R_{42}$ is hydrogen or substituted hydrocarbyl. For example, in one such embodiment each $R_{12}$ is aminoalkyl, allyl or vinyl, $R_{22}$ and $R_{32}$ are independently hydrogen, alkyl, aminoalkyl, haloalkyl, alkenyl, or alkanol, and $R_{42}$ is hydrogen or substituted hydrocarbyl. By way of further example, in one such embodiment each $R_{12}$ and $R_{42}$ is independently hydrogen, alkyl, allyl, vinyl, —$(CH_2)_d NH_2$ or —$(CH_2)_d N[(CH_2)_e NH_2]_2$ where d and e are independently 2-4, and $R_{22}$ and $R_{32}$ are independently hydrogen or heteroaliphatic.

Exemplary amines and crosslinkers (or the salts thereof, for example the hydrochloric acid, phosphoric acid, sulfuric acid, or hydrobromic acid salts thereof) for the synthesis of polymers described by Formula 2b include but are not limited to the ones in Table 3.

In some embodiments, the crosslinked amine polymer is derived from a reaction of the resulting polymers that utilize monomers described in any of Formulae 1, 1a, 1b, 1c, 2, 2a and 2b or a linear polymer comprised of a repeat unit described by Formula 3 with external crosslinkers or pre-existing polymer functionality that can serve as crosslinking sites. Formula 3 can be a repeat unit of a copolymer or terpolymer where $X_{15}$ is either a random, alternating, or block copolymer. The repeating unit in Formula 3 can also represent the repeating unit of a polymer that is branched, or hyperbranched, wherein the primary branch point can be from any atom in the main chain of the polymer:

Formula 3

TABLE 3

| Abbreviation | Common name | IUPAC name | | MW (g/mol) |
|---|---|---|---|---|
| DABDA1 | Diallylbutyldiamine | 1,4-Bis(allylamino)butane | | 241.2 |
| DAEDA1 | Diallylethyldiamine | 1,2-Bis(allylamino)ethane | | 213.15 |
| DAEDA2 | Diallyldiethylenetriamine | 2-(Allylamino)-1-[2-(allylamino)ethylamino]ethane | | 292.67 |
| DAPDA | Diallylpropyldiamine | 1,3-Bis(allylamino)propane | | 227.17 |
| POHDA | Diallylamineisopropanol | 1,3-Bis(allylamino)-2-propanol | | 243.17 |
| AAH | Allylamine | 2-Propen-1-ylamine | | 93.5 |
| AEAAH | Aminoethylallylamine | 1-(Allylamino)-2-aminoethane | | 173.08 |
| BAEAAH | Bis(2-aminoethyl)allylamine | 1-[N-Allyl(2-aminoethyl)amino]-2-aminoethane | | 252.61 |
| TAA | Triallylamine | N,N,N-triallylamine | | 137.22 | wherein $R_{15}$, $R_{16}$ and $R_{17}$ are independently hydrogen, hydrocarbyl, substituted hydrocarbyl, hydroxyl, amino, boronic acid or halo;

$X_{15}$ is

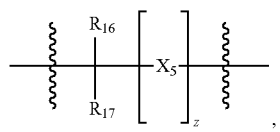

$X_5$ is hydrocarbyl, substituted hydrocarbyl, oxo (—O—), or amino and z is a non-negative number.

In one embodiment, $R_{15}$, $R_{16}$ and $R_{17}$ are independently hydrogen, aryl, or heteroaryl, $X_5$ is hydrocarbyl, substituted hydrocarbyl, oxo or amino, and m and z are non-negative integers. In another embodiment, $R_{15}$, $R_{16}$ and $R_{17}$ are independently aliphatic or heteroaliphatic, $X_5$ is hydrocarbyl, substituted hydrocarbyl, oxo (—O—) or amino, and m and z are non-negative integers. In another embodiment, $R_{15}$, $R_{16}$ and $R_{17}$ are independently unsaturated aliphatic or unsaturated heteroaliphatic, $X_5$ is hydrocarbyl, substituted hydrocarbyl, oxo, or amino, and z is a non-negative integer. In another embodiment, $R_{15}$, $R_{16}$ and $R_{17}$ are independently alkyl or heteroalkyl, $X_5$ is hydrocarbyl, substituted hydrocarbyl, oxo, or amino, and z is a non-negative integer. In another embodiment, $R_{15}$, $R_{16}$ and $R_{17}$ are independently alkylamino, aminoalkyl, hydroxyl, amino, boronic acid, halo, haloalkyl, alkanol, or ethereal, $X_5$ is hydrocarbyl, substituted hydrocarbyl, oxo, or amino, and z is a non-negative integer. In another embodiment, $R_{15}$, $R_{16}$ and $R_{17}$ are independently hydrogen, hydrocarbyl, substituted hydrocarbyl, hydroxyl, amino, boronic acid or halo, $X_5$ is oxo, amino, alkylamino, ethereal, alkanol, or haloalkyl, and z is a non-negative integer.

Exemplary crosslinking agents that may be used in radical polymerization reactions include, but are not limited to, one or more multifunctional crosslinking agents such as: 1,4-bis(allylamino)butane, 1,2-bis(allylamino)ethane, 2-(allylamino)-1-[2-(allylamino)ethylamino]ethane, 1,3-bis(allylamino)propane, 1,3-bis(allylamino)-2-propanol, triallylamine, diallylamine, divinylbenzene, 1,7-octadiene, 1,6-heptadiene, 1,8-nonadiene, 1,9-decadiene, 1,4-divinyloxybutane, 1,6-hexamethylenebisacrylamide, ethylene bisacrylamide, N,N'-bis(vinylsulfonylacetyl)ethylene diamine, 1,3-bis(vinylsulfonyl) 2-propanol, vinylsulfone, N,N'-methylenebisacrylamide polyvinyl ether, polyallylether, divinylbenzene, 1,4-divinyloxybutane, and combinations thereof.

Crosslinked polymers derived from the monomers and polymers in formulas 1 through 3 may be synthesized either in solution or bulk or in dispersed media. Examples of solvents that are suitable for the synthesis of polymers of the present disclosure include, but are not limited to water, low boiling alcohols (methanol, ethanol, propanol, butanol), dimethylformamide, dimethylsulfoxide, heptane, chlorobenzene, toluene.

Alternative polymer processes may include, a lone polymerization reaction, stepwise addition of individual starting material monomers via a series of reactions, the stepwise addition of blocks of monomers, combinations or any other method of polymerization such as living polymerization, direct polymerization, indirect polymerization, condensation, radical, emulsion, precipitation approaches, spray dry polymerization or using some bulk crosslinking reaction methods and size reduction processes such as grinding, compressing, extrusion. Processes can be carried out as a batch, semi-continuous and continuous processes. For processes in dispersed media, the continuous phase can be non-polar solvents, such as toluene, benzene, hydrocarbon, halogenated solvents, super critical carbon dioxide. With a direct suspension reaction, water can be used and salt can be used to tune the properties of the suspension.

The starting molecules described in formulas 1 through 3 may be copolymerized with one or more other monomers of the invention, oligomers or other polymerizable groups. Such copolymer architectures can include, but are not limited to, block or block-like polymers, graft copolymers, and random copolymers. Incorporation of monomers described by formulas 1 through 3 can range from 1% to 99%. In some embodiments, the incorporation of comonomer is between 20% and 80%.

Non-limiting examples of comonomers which may be used alone or in combination include: styrene, allylamine hydrochloride, substituted allylamine hydrochloride, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof. Functionalized versions of these monomers may also be used. Additional specific monomers or comonomers that may be used in this invention include, but are not limited to, 2-propen-1-ylamine, 1-(allylamino)-2-aminoethane, 1-[N-allyl(2-aminoethyl)amino]-2-aminoethane, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, amethylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacryl amide, N-Nbutylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinyltether, butadiene, isoprene, chloroprene, ethylene, vinyl acetate, and combinations thereof.

Additional modification to the preformed crosslinked polymer can be achieved through the addition of modifiers, including but not limited to amine monomers, additional crosslinkers, and polymers. Modification can be accomplished through covalent or non-covalent methods. These modifications can be evenly or unevenly dispersed throughout the preformed polymer material, including modifications biased to the surface of the preformed crosslinked polymer. Furthermore, modifications can be made to change the physical properties of the preformed crosslinked polymer, including but not limited to reactions that occur with remaining reactive groups such as haloalkyl groups and allyl groups in the preformed polymer. Reactions and modifications to the preformed crosslinked polymer can include but are not limited to acid-base reactions, nucleophilic substitution reactions, Michael reactions, non-covalent electrostatic interactions, hydrophobic interactions, physical interactions (crosslinking) and radical reactions.

As described in greater detail in the Examples, polymers in which crosslinking and/or entanglement were increased were found to have lower swelling than those with lower crosslinking and/or entanglement, yet also had a binding capacity for target ion (e.g., chloride) that was as great as or greater than the lower crosslinking and/or entanglement polymers while binding of interfering ions such as phosphate were significantly reduced. The selectivity effect was introduced in two different manners: 1) Overall capacity was sacrificed for chloride specificity. Crosslinkers that don't include chloride binding sites (e.g. epichlorohydrin) allow for increased crosslinking while overall capacity is decreased proportional to the amount of crosslinker incorporated into the polymer. 2) Overall capacity is preserved for chloride specificity: Crosslinkers that include chloride binding sites (e.g. diallylamines) allow for increased crosslinking while overall capacity is staying the same or is reduced by only a small amount.

The polymers described herein exhibit ion binding properties, generally proton binding to form the positive charge followed by anion-binding. In preferred embodiments, the polymers exhibit chloride binding properties. Ion (e.g., chloride) binding capacity is a measure of the amount of a particular ion an ion binder can bind in a given solution. For example, binding capacities of ion-binding polymers can be measured in vitro, e.g., in water or in saline solution or in solutions/matrices containing cations and anions representative of gastrointestinal lumen conditions, or in vivo, e.g., from ion (e.g., bicarbonate or citrate) urinary excretion, or ex vivo, for example using aspirate liquids, e.g., chime/gastrointestinal lumen contents obtained from lab animals, patients or volunteers. Measurements can be made in a solution containing only the target ion, or at least no other competing solutes that compete with target ions for binding to the polymer. In these cases, a non-interfering buffer would be used (e.g. a solution of hydrochloric acid, with or without additional sodium chloride). Alternatively, measurements can be made in an interfering buffer that contains other competing solutes, e.g., other ions or metabolites that compete with target ions for binding to the resin.

In some embodiments the polymer binds hydrochloric acid. For in vivo use, e.g., in treating metabolic acidosis, it is desirable that the polymer have a high proton and chloride binding capacity. In vitro measurements of binding capacity do not necessarily translate into in vivo binding capacities. Hence, it is useful to define binding capacity in terms of both in vitro and in vivo capacity.

The in vitro chloride binding capacity of the polymers of the invention in HCl can be greater than about 5, 6, 7, 8, 9, 10, 11, 12, 13, 14 or 15 mmol/g. In some embodiments, the in vitro chloride binding capacity of the polymers of the invention for target ion is greater than about 5.0 mmol/g, preferably greater than about 7.0 mmol/g, even more preferably greater than about 9.0 mmol/g, and yet even more preferably greater than about 10.0 mmol/g. In some embodiments, the chloride binding capacity can range from about 5.0 mmol/g to about 25 mmol/g, preferably from about 7.5 mmol/g to about 20 mmol/g, and even more preferably from about 10 mmol/g to about 15 mmol/g. Several techniques are known in the art to determine the chloride binding capacity.

The in vivo maximum binding capacity (i.e. the maximum amount of [proton and] chloride bound in conditions likely to be encountered in the GI tract of a human) can be evaluated by 12-16 h chloride binding in the Simulated Gastric Fluid assay ("SGF") and is a structural measure for how well the monomers and crosslinkers were incorporated. The SGF values represent an experimental confirmation of the theoretical maximum binding capacity of the polymers and fall in the same range as the calculated capacity based on the stoichiometry of the starting materials.

In order to counterbalance the proton binding, chloride is the anion of choice to be bound as its removal has no negative impact on serum bicarbonate. Anions other than chloride, bound to neutralize the proton positive charge, include phosphate, short chain fatty acids, long chain fatty acids, bile acids or other organic or inorganic anions. Binding of these anions, other than chloride, influences overall bicarbonate stores in the intracellular and extracellular compartments.

The selectivity of the polymer for binding chloride can be evaluated in vitro using conditions that mimic various conditions, anions and anion concentrations encountered in the GI lumen. The chloride binding can be compared versus phosphate alone (e.g. SIB [Simulated Intestinal Buffer]; or versus a range of anions found in the GI tract (e.g., SOB).

In some embodiments, the chloride binding in the SIB assay after one hours exposure of the polymer to the test buffer at 37° C. is greater than about 2.0 mmol per gram of polymer, preferably greater than about 2.5 mmol/g of polymer, more preferably greater than about 3.0 mmol/g of polymer, even more preferably greater than about 3.5 mmol/g of polymer and most preferably greater than about 4.0 mmol/g of polymer.

In some embodiments, the chloride binding in the SOB assay after two hours exposure of the polymer to the test buffer at 37° C. is greater than about 1.0 mmol per gram of polymer, preferably greater than about 2.0 mmol/g of polymer, more preferably greater than about 3.0 mmol/g of polymer, even more preferably greater than about 3.5 mmol/g of polymer and most preferably greater than about 4.0 mmol/g of polymer.

In some embodiments, the chloride binding in this SOB assay after forty eight hours exposure of the polymer to the test buffer at 37° C. is greater than about 0.5 mmol per gram of polymer, preferably greater than about 1 mmol/g of polymer, more preferably greater than about 2.0 mmol/g of polymer, even more preferably greater than about 3.0 mmol/g of polymer and most preferably greater than about 4.0 mmol/g of polymer. The chloride binding in SOB after 48 hours exposure at 37° C. is one measure of the ability of a polymer to retain chloride as it passes through the GI tract.

Another way of measuring (proton and) chloride retention is to first expose the polymer to SOB, to isolate the polymer and then to expose the polymer to conditions that are typical of the colon lumen, for example using the "chloride retention assay" (CRA) buffer. In some embodiments, the amount of chloride remaining bound to the polymer after two hours exposure to SOB at 37° C. and then 48 hours exposure to CRA at 37° C. is greater than about 0.2 mmol per gram of polymer, preferably greater than about 0.5 mmol/g of polymer, more preferably greater than about 1.0 mmol/g of polymer, even more preferably greater than about 2.0 mmol/g of polymer and most preferably greater than about 3.0 mmol/g of polymer.

In some embodiments, the in vivo binding performance of polymers of the present disclosure can be evaluated by measuring the change in urine acid levels after administration to an animal, including a human, with normal renal function. The removal of additional HCl (or HCl equivalent) from the body by the action of the administered polymer, given enough time to reach metabolic equilibrium, is reflected in changes in urine bicarbonate, titratable acid, citrate or other indicators of urinary acid excretion.

In order to bind protons, the amine constituents of the polymers can be primary, secondary or tertiary amines, but not quaternary amines. Quaternary amines remain substantially charged at all physiological conditions and therefore do not bind a proton before an anion is bound. The percentage of quaternary amines can be measured in a number of ways, including titration and back titration approaches. Another simple but accurate method is to compare anion (e.g. chloride) binding at low and high pH. While chloride binding at low pH (e.g. the SGF buffer conditions; pH 1.2) does not distinguish quaternary amines from other amines, chloride binding assay at high pH (e.g. QAA buffer conditions; pH 11.5) does. At this high pH, primary, secondary and tertiary amines are not substantially protonated and do not contribute to chloride binding. Therefore any binding observed under these conditions can be attributed to the presence of permanently charged quaternary amines. A comparison of chloride binding at low pH (e.g. SGF conditions) versus high pH (e.g. QAA conditions) is a measure of the degree of quaternization and by extension is a measure of the amount of proton bound along with the chloride. The polymers of the current disclosure contain no more than 40%, 30%, 20%, 10% most preferably 5% quaternary amines.

The swelling ratio of the polymers of the present disclosure represent an experimental confirmation of the degree of crosslinking and by extension the relative pore sizes of the polymers and accessibility to anions larger than (or with a hydration ratio larger than) chloride. In some embodiments the swelling is measured in deionized water and is expressed in terms of grams of water per gram of dry polymer. The polymers of the current disclosure have a swelling ratio in deionized water of ≤5 g/g, ≤4 g/g, ≤3 g/g, ≤2 g/g or ≤1 g/g.

The ability of polymer to retain chloride (and not release it, allowing exchange with other anions) as it passes through different conditions experienced in the GI lumen is an important characteristic that is likely to be a predictor of relative in vivo efficacy. The chloride retention assay (CRA) can be used to evaluate chloride retention. An SOB (Simulated Intestinal Organic/Inorganic Buffer) screen is first performed to allow chloride and other anions to bind to the polymers, the polymers are isolated and exposed to conditions mimicking the colon lumen (e.g. retention assay matrix) for 40 hours. The polymers are again isolated and the anions remaining bound to the polymer are eluted in sodium hydroxide and measured. The polymers of the current disclosure retain more than 50%, 60%, 70%, 80% or most preferably more than 90% of chloride bound after being submitted to the chloride retention assay as described.

Using heterogeneous polymerization processes, polymer particles are obtained as spherical beads, whose diameter is controlled in the 5 to 1000 microns range, preferably 10 to 500 microns and most preferred 40-180 microns.

In general, a pharmaceutical composition of the present disclosure comprises a proton-binding, crosslinked amine polymer described herein. Preferably, the pharmaceutical composition comprising the crosslinked amine polymer is formulated for oral administration. The form of the pharmaceutical in which the polymer is administered includes powders, tablets, pills, lozenges, sachets, cachets, elixirs, suspensions, syrups, soft or hard gelatin capsules, and the like. In one embodiment, the pharmaceutical composition comprises only the crosslinked amine polymer. Alternatively, the pharmaceutical composition may comprise a carrier, a diluent, or excipient in addition to the crosslinked amine polymer. Examples of carriers, excipients, and diluents that may be used in these formulations as well as others, include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc. Pharmaceutical excipients useful in the pharmaceutical compositions further include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumarate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), Remington's Pharmaceutical Sciences, 20th Edition.

In one embodiment, pharmaceutical compositions comprising a crosslinked amine polymer of the present disclosure contain relatively low amounts of sodium. For example, in one such embodiment the pharmaceutical composition comprises less than 1 g of sodium per dose. By way of further example, in one such embodiment the pharmaceutical composition comprises less than 0.5 g sodium per dose. By way of further example, in one such embodiment the pharmaceutical composition comprises less than 0.1 g sodium per dose. By way of further example, in one such embodiment the pharmaceutical composition is sodium-free.

In one embodiment, the daily dose of the new chronic metabolic acidosis treatment is compliance enhancing (approximately 5 g or less per day) and achieves a clinically significant and sustained increase of serum bicarbonate of approximately 3 mEq/L at these daily doses. The non-absorbed nature of the polymer and the lack of sodium load and/or introduction of other deleterious ions for such an oral drug enable for the first time a safe, chronic treatment of metabolic acidosis without worsening blood pressure/hypertension and/or without causing increased fluid retention and fluid overload. Another benefit is further slowing of the progression of kidney disease and time to onset of lifelong renal replacement therapy (End Stage Renal Disease "ESRD" including 3 times a week dialysis) or need for kidney transplants. Both are associated with significant mortality, low quality of life and significant burden to healthcare systems around the world. In the United States alone, approximately 20% of the 400,000 ESRD patients die and 100,000 new patients start dialysis every year.

In one embodiment, the pharmaceutical composition comprises a sodium-free, non-absorbed, cross-linked, amine polymer for treatment of metabolic acidosis that increases serum bicarbonate and normalizes blood pH in a mammal by binding HCl. One preferred embodiment includes the polymer binding $H^+$ in the stomach/upper GI tract followed by binding $Cl^-$ in sufficient amounts to cause a clinically meaningful increase of serum bicarbonate of at least 1.6 mEq/L, more preferred of at least 2 mEq/L and most preferred of equal or greater 3 mEq/L. The amount of HCl binding is determined by the polymer's capacity (targeted range of HCl binding capacity of 5-20 mEq of HCl per 1 g of polymer) and selectivity. In the stomach, free amine becomes protonated by binding $H^+$. The positive charge formed in situ on the polymer is then available to bind $Cl^-$; by controlling access of binding sites through crosslinking (size exclusion, mesh size) and chemical moieties (to repel larger, organic ions (such as acetate, propionate and butyrate or other short chain fatty acids commonly present in the colon), phosphate, bile and fatty acids through tailored hydrophilicity/hydrophobicity), anions other than chloride are bound to a lesser degree if at all. By tailoring the bead crosslinking and the chemical nature of the amine binding sites, chloride can be bound tightly to ensure that it is not released in the lower GI tract. HCl is removed from the body through regular bowel movement/feces, resulting in net HCl binding. In another embodiment, the polymer comes preformed with some quaternized/protonated amine groups and chloride binding is achieved through ion exchange with citrate or carbonate where up to 90% of cationic binding sites on the polymer come pre-loaded with citrate and/or carbonate as the counter-ion.

In one embodiment, a key feature of the sodium-free, non-absorbed, amine polymer for treatment of metabolic acidosis that increases serum bicarbonate and normalizes blood pH in a mammal is that it does not increase blood pressure or worsen hypertension which is of particular concern in diabetic kidney disease patients. An additional benefit of not introducing sodium is the lack of related increase in fluid retention causing fluid overload which is of particular concern in heart failure patients. The polymer's ability to safely and efficaciously treat metabolic acidosis without introducing deleterious counter-ions allows for slowing of progression of kidney disease which is of particular concern in chronic kidney disease patients who are not on dialysis yet. The onset of dialysis could be delayed by at least 3, 6, 9 or 12 months.

In yet another embodiment of the sodium-free, non-absorbed, amine polymer for treatment of metabolic acidosis, the polymer is a crosslinked bead with a preferred particle size range that is (i) large enough to avoid passive or active absorption through the GI tract and (ii) small enough to not cause grittiness or unpleasant mouth feel when ingested as a powder, sachet and/or chewable tablet/dosage form with an average particle size of 40-180 microns. Preferably, the desired particle size morphology is accomplished through a heterogeneous polymerization reaction such as a suspension or emulsion polymerization. To minimize GI side effects in patients that are often related to a large volume polymer gel moving through the GI tract, a low swelling ratio of the polymer is preferred (0.5-5 times its own weight in water). In yet another embodiment, the polymer carries a molecular entity permanently/covalently and/or temporarily attached to a polymer or on its own that blocks the $Cl^-/HCO_3^-$ exchanger (antiporter) in the colon and intestine. The net effect of blocking the antiporter is to reduce uptake of $Cl^-$ from the intestinal lumen and related exchange for bicarbonate from the serum, thus effectively increasing serum bicarbonate.

In one embodiment, the crosslinked amine polymer may be co-administered with other active pharmaceutical agents depending on the condition being treated. This co-administration may include simultaneous administration of the two agents in the same dosage form, simultaneous administration in separate dosage forms, and separate administration. For example, for the treatment of metabolic acidosis, the crosslinked amine polymer may be co-administered with common treatments that are required to treat underlying co-morbidities including but not limited to hypertension, diabetes, obesity, heart failure and complications of Chronic Kidney Disease. These medications and the crosslinked amine polymer can be formulated together in the same dosage form and administered simultaneously as long as they do not display any clinically significant drug-drug-interactions. Alternatively, these treatments and the crosslinked amine polymer may be separately and sequentially administered with the administration of one being followed by the administration of the other.

In further embodiments, numbered 1-104 below, the present includes

Embodiment 1

A pharmaceutical composition comprising a proton-binding, crosslinked amine polymer comprising the residue of an amine corresponding to Formula 1:

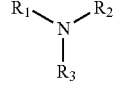

Formula 1 wherein $R_1$, $R_2$ and $R_3$ are independently hydrogen, hydrocarbyl, or substituted hydrocarbyl provided, however, at least one of $R_1$, $R_2$ and $R_3$ is other than hydrogen, and the crosslinked amine polymer has (i) an equilibrium proton binding capacity of at least 5 mmol/g and a chloride ion binding capacity of at least 5 mmol/g in an aqueous simulated gastric fluid buffer ("SGF") containing 35 mM NaCl and 63 mM HCl at pH 1.2 and 37° C., and (ii) an equilibrium swelling ratio in deionized water of about 2 or less.

Embodiment 2

A pharmaceutical composition comprising a proton-binding, crosslinked amine polymer comprising the residue of an amine corresponding to Formula 1:

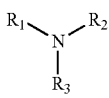

Formula 1 wherein $R_1$, $R_2$ and $R_3$ are independently hydrogen, hydrocarbyl, substituted hydrocarbyl provided, however, at least one of $R_1$, $R_2$ and $R_3$ is other than hydrogen, the crosslinked amine polymer has an equilibrium swelling ratio in deionized water of about 5 or less, and the crosslinked amine polymer binds a molar ratio of chloride ions to interfering ions of at least 0.35:1, respectively, in an interfering ion buffer at 37° C. wherein (i) the interfering ions are phosphate ions and the interfering ion buffer is a buffered solution at pH 5.5 of 36 mM chloride and 20 mM phosphate or (ii) the interfering ions are phosphate, citrate and taurocholate ions (combined amount) and the interfering ion buffer is a buffered solution at pH 6.2 including 36 mM chloride, 7 mM phosphate, 1.5 mM citrate, and 5 mM taurocholate.

Embodiment 3

The pharmaceutical composition of embodiment 1 wherein the crosslinked amine polymer has an equilibrium chloride binding capacity of at least 7.5 mmol/g in an aqueous simulated gastric fluid buffer ("SGF") containing 35 mM NaCl and 63 mM HCl at pH 1.2 and 37° C.

Embodiment 4

The pharmaceutical composition of embodiment 1 wherein the crosslinked amine polymer has an equilibrium chloride binding capacity of at least 10 mmol/g in an aqueous simulated gastric fluid buffer ("SGF") containing 35 mM NaCl and 63 mM HCl at pH 1.2 and 37° C.

Embodiment 5

The pharmaceutical composition of embodiment 2 wherein the crosslinked amine polymer binds more chloride than any one of the interfering anions in the interfering ion buffer, the interfering ions are phosphate, citrate and taurocholate ions and the interfering ion buffer is a buffered solution at pH 6.2 including 36 mM chloride, 7 mM phosphate, 1.5 mM citrate, and 5 mM taurocholate.

Embodiment 6

The pharmaceutical composition of embodiment 2 wherein at least 66% of the combined amount of chloride and interfering ions bound by the crosslinked amine polymer in the interfering ion buffer are chloride anions, the interfering ions are phosphate, citrate and taurocholate, and the interfering ion buffer is a buffered solution at pH 6.2 including 36 mM chloride, 7 mM phosphate, 1.5 mM citrate, and 5 mM taurocholate.

Embodiment 7

The pharmaceutical composition of embodiment 2 wherein 90% or more of the combined amount of chloride and interfering ions bound by the crosslinked amine polymer in the interfering ion buffer are chloride anions, the interfering ions are phosphate, citrate and taurocholate, and the interfering ion buffer is a buffered solution at pH 6.2 including 36 mM chloride, 7 mM phosphate, 1.5 mM citrate, and 5 mM taurocholate.

Embodiment 8

The pharmaceutical composition of embodiment 2 wherein the crosslinked amine polymer has an equilibrium swelling ratio in deionized water of about 4 or less.

Embodiment 9

The pharmaceutical composition of embodiment 2 wherein the crosslinked amine polymer has an equilibrium swelling ratio in deionized water of about 3 or less.

Embodiment 10

The pharmaceutical composition of embodiment 2 wherein the crosslinked amine polymer has an equilibrium swelling ratio in deionized water of about 2 or less.

Embodiment 11

The pharmaceutical composition of any preceding embodiment wherein $R_1$, $R_2$ and $R_3$ are independently hydrogen, alkyl, alkenyl, allyl, vinyl, aryl, aminoalkyl, alkanol, haloalkyl, hydroxyalkyl, ethereal, heteroaryl or heterocyclic provided, however, each of $R_1$, $R_2$ and $R_3$ is not hydrogen.

Embodiment 12

The pharmaceutical composition of any preceding embodiment wherein $R_1$, $R_2$ and $R_3$ are independently hydrogen, aliphatic or heteroaliphatic provided, however, at least one of $R_1$, $R_2$ and $R_3$ is other than hydrogen.

Embodiment 13

The pharmaceutical composition of any preceding embodiment wherein the crosslinked amine polymer is prepared by substitution polymerization of the amine with a polyfunctional crosslinker, optionally also comprising amine moieties.

Embodiment 14

The pharmaceutical composition of any of embodiments 1-12 wherein the crosslinked amine polymer comprises the residue of an amine corresponding to Formula 1a and the crosslinked amine polymer is prepared by radical polymerization of an amine corresponding to Formula 1a:

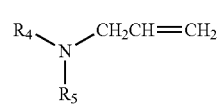

Formula 1a wherein $R_4$ and $R_5$ are independently hydrogen, hydrocarbyl, or substituted hydrocarbyl.

Embodiment 15

The pharmaceutical composition of embodiment 14 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 16

The pharmaceutical composition of embodiment 14 wherein $R_4$ and $R_5$ are independently hydrogen, aliphatic or heteroaliphatic.

Embodiment 17

The pharmaceutical composition of any of embodiments 1-12 wherein the crosslinked amine polymer comprises the residue of an amine corresponding to Formula 1 b and the crosslinked amine polymer is prepared by substitution polymerization of the amine corresponding to Formula 1 b with a polyfunctional crosslinker:

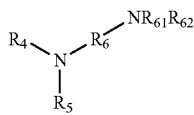

Fromula 1b wherein $R_4$ and $R_5$ are independently hydrogen, hydrocarbyl, or substituted hydrocarbyl, $R_6$ is aliphatic and $R_{61}$ and $R_{62}$ are independently hydrogen, aliphatic, or heteroaliphatic.

Embodiment 18

The pharmaceutical composition of embodiment 17 wherein $R_4$ and $R_5$ are independently hydrogen, saturated hydrocarbon, unsaturated aliphatic, aryl, heteroaryl, heteroalkyl, or unsaturated heteroaliphatic.

Embodiment 19

The pharmaceutical composition of embodiment 17 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

Embodiment 20

The pharmaceutical composition of embodiment 17 wherein $R_4$ and $R_5$ are independently hydrogen, allyl, or aminoalkyl.

Embodiment 21

The pharmaceutical composition of any preceding embodiment wherein the crosslinked amine polymer comprises the residue of an amine corresponding to Formula 1c:

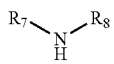

Formula 1c wherein $R_7$ is hydrogen, aliphatic or heteroaliphatic and $R_8$ is aliphatic or heteroaliphatic.

Embodiment 22

The pharmaceutical composition of any of embodiments 1-12 wherein the crosslinked amine polymer comprises the residue of an amine corresponding to Formula 2:

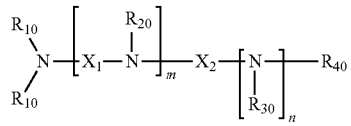

Formula 2 wherein
m and n are independently non-negative integers;
$R_{10}$, $R_{20}$, $R_{30}$, and $R_{40}$ are independently hydrogen, hydrocarbyl, or substituted hydrocarbyl;
$X_1$ is

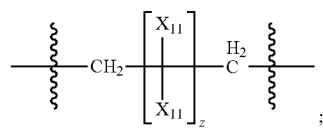

$X_2$ is hydrocarbyl or substituted hydrocarbyl;
each $X_{11}$ is independently hydrogen, hydrocarbyl, substituted hydrocarbyl, hydroxy, or amino; and
z is a non-negative number.

Embodiment 23

The pharmaceutical composition of embodiment 22 wherein $R_{10}$, $R_{20}$, $R_{30}$, and $R_{40}$ are independently hydrogen, aliphatic, aryl, heteroaliphatic, or heteroaryl, m and z are independently 0-3 and n is 0 or 1.

Embodiment 24

The pharmaceutical composition of embodiment 22 or 23 wherein $X_2$ is aliphatic or heteroaliphatic.

Embodiment 25

The pharmaceutical composition of embodiment 22, 23 or 24 wherein m is 1-3 and $X_{11}$ is hydrogen, aliphatic or heteroaliphatic.

Embodiment 26

The pharmaceutical composition of any of embodiments 1-12 wherein the crosslinked amine polymer comprises the residue of an amine corresponding to Formula 2a:

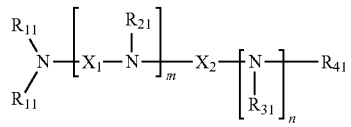

Formula 2a wherein
m and n are independently non-negative integers;
each $R_{11}$ is independently hydrogen, hydrocarbyl, heteroaliphatic, or heteroaryl;
$R_{21}$ and $R_{31}$, are independently hydrogen or heteroaliphatic;
$R_{41}$ is hydrogen, substituted hydrocarbyl, or hydrocarbyl;

$X_1$ is

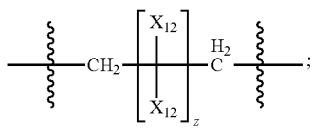

$X_2$ is alkyl or substituted hydrocarbyl;
each $X_{12}$ is independently hydrogen, hydroxy, amino, aminoalkyl, boronic acid or halo; and
z is a non-negative number.

Embodiment 27

The pharmaceutical composition of embodiment 26 wherein m and z are independently 0-3 and n is 0 or 1.

Embodiment 28

The pharmaceutical composition of embodiment 26 or 27 wherein $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl.

Embodiment 29

The pharmaceutical composition of embodiment 26 or 27 wherein each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic.

Embodiment 30

The pharmaceutical composition of any of embodiments 1-12 wherein the crosslinked amine polymer comprises the residue of an amine corresponding to Formula 2b:

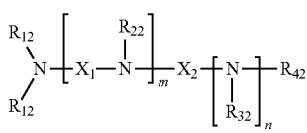

Formula 2b wherein
m and n are independently non-negative integers;
each $R_{12}$ is independently hydrogen, substituted hydrocarbyl, or hydrocarbyl;
$R_{22}$ and $R_{32}$ are independently hydrogen substituted hydrocarbyl, or hydrocarbyl;
$R_{42}$ is hydrogen, hydrocarbyl or substituted hydrocarbyl;
$X_1$ is

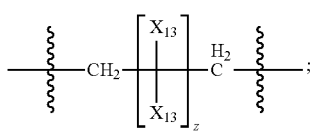

$X_2$ is alkyl, aminoalkyl, or alkanol;
each $X_{13}$ is independently hydrogen, hydroxy, alicyclic, amino, aminoalkyl, halogen, alkyl, heteroaryl, boronic acid or aryl;

z is a non-negative number; and
the amine corresponding to Formula 2b comprises at least one allyl group.

Embodiment 31

The pharmaceutical composition of embodiment 30 wherein m and z are independently 0-3 and n is 0 or 1.

Embodiment 32

The pharmaceutical composition of embodiment 30 or 31 wherein $R_{12}$ or $R_{42}$ independently comprise at least one allyl or vinyl moiety.

Embodiment 33

The pharmaceutical composition of embodiment 30 or 31 wherein (i) m is a positive integer and $R_{12}$, $R_{22}$ and $R_{42}$, in combination comprise at least two allyl or vinyl moieties or (ii) n is a positive integer and $R_{12}$, $R_{32}$ and $R_{42}$, in combination, comprise at least two allyl or vinyl moieties.

Embodiment 34

The pharmaceutical composition of embodiment 30 or 31 wherein the crosslinked amine polymer comprises the residue of an amine appearing in Table 1.

Embodiment 35

The pharmaceutical composition of embodiment 30, 31 or 34 wherein the crosslinked amine polymer is crosslinked with a crosslinking agent appearing in Table 2.

Embodiment 36

The pharmaceutical composition of any preceding embodiment wherein the crosslinked amine polymer comprises a repeat unit corresponding to Formula 3:

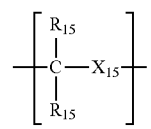

Formula 3 wherein
$R_{15}$, $R_{16}$ and $R_{17}$ are independently hydrogen, hydrocarbyl, substituted hydrocarbyl, hydroxyl, amino, boronic acid or halo;
$X_{15}$ is

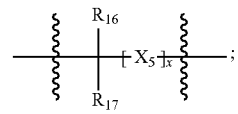

$X_5$ is hydrocarbyl, substituted hydrocarbyl, oxo (—O—), or amino; and
z is a non-negative number.

Embodiment 37

The pharmaceutical composition of embodiment 36 wherein $R_{15}$, $R_{16}$ and $R_{17}$ are independently aliphatic or heteroaliphatic.

Embodiment 38

The pharmaceutical composition of embodiment 36 or 37 wherein $X_5$ is oxo, amino, alkylamino, ethereal, alkanol, or haloalkyl.

Embodiment 39

The pharmaceutical composition of any of embodiments 1-12 wherein the crosslinked amine polymer is prepared by (i) substitution polymerization of polyfunctional reagents at least one of which comprises amine moieties, (2) radical polymerization of a monomer comprising at least one amine moiety or nitrogen containing moiety, or (3) crosslinking of an amine-containing intermediate with a crosslinking agent, optionally containing amine moieties.

Embodiment 40

The pharmaceutical composition of embodiment 39 wherein the crosslinked amine polymer is a crosslinked homopolymer or a crosslinked copolymer.

Embodiment 41

The pharmaceutical composition of embodiment 39 wherein the crosslinked amine polymer comprises free amine moieties, separated by the same or varying lengths of repeating linker units.

Embodiment 42

The pharmaceutical composition of embodiment 39 wherein the crosslinked amine polymer is prepared by polymerizing an amine-containing monomer with a crosslinking agent in a substitution polymerization reaction.

Embodiment 43

The pharmaceutical composition of embodiment 42 wherein the amine-containing monomer is a linear amine possessing at least two reactive amine moieties to participate in the substitution polymerization reaction.

Embodiment 44

The pharmaceutical composition of embodiment 42 or 43 wherein the amine-containing monomer is 1,3-Bis[bis(2-aminoethyl)amino]propane, 3-Amino-1-{[2-(bis{2-[bis(3-aminopropyl)amino]ethyl}amino)ethyl](3-aminopropyl)amino}propane, 2-[Bis(2-aminoethyl)amino]ethanamine, Tris(3-aminopropyl)amine, 1,4-Bis[bis(3-aminopropyl)amino]butane, 1,2-Ethanediamine, 2-Amino-1-(2-aminoethylamino)ethane, 1,2-Bis(2-aminoethylamino)ethane, 1,3-Propanediamine, 3,3'-Diaminodipropylamine, 2,2-dimethyl-1,3-propanediamine, 2-methyl-1,3-propanediamine, N,N'-dimethyl-1,3-propanediamine, N-methyl-1,3-diaminopropane, 3,3'-diamino-N-methyldipropylamine, 1,3-diaminopentane, 1,2-diamino-2-methylpropane, 2-methyl-1,5-diaminopentane, 1,2-diaminopropane, 1,10-diaminodecane, 1,8-diaminooctane, 1,9-diaminooctane, 1,7-diaminoheptane, 1,6-diaminohexane, 1,5-diaminopentane, 3-bromopropylamine hydrobromide, N,2-dimethyl-1,3-propanediamine, N-isopropyl-1,3-diaminopropane, N,N'-bis(2-aminoethyl)-1,3-propanediamine, N,N'-bis(3-aminopropyl) ethylenediamine, N,N'-bis(3-aminopropyl)-1,4-butanediamine tetrahydrochloride, 1,3-diamino-2-propanol, N-ethylethylenediamine, 2,2'-diamino-N-methyldiethylamine, N,N'-diethylethylenediamine, N-isopropylethylenediamine, N-methylethylenediamine, N,N'-di-tert-butylethylenediamine, N,N'-diisopropylethylenediamine, N,N'-dimethylethylenediamine, N-butylethylenediamine, 2-(2-aminoethylamino)ethanol, 1,4,7,10,13,16-hexaazacyclooctadecane, 1,4,7,10-tetraazacyclododecane, 1,4,7-triazacyclononane, N,N'-bis(2-hydroxyethyl)ethylenediamine, piperazine, bis(hexamethylene)triamine, N-(3-hydroxypropyl)ethylenediamine, N-(2-Aminoethyl)piperazine, 2-Methylpiperazine, Homopiperazine, 1,4,8,11-Tetraazacyclotetradecane, 1,4,8,12-Tetraazacyclopentadecane, 2-(Aminomethyl)piperidine, or 3-(Methylamino)pyrrolidino.

Embodiment 45

The pharmaceutical composition of any of embodiments 39, 41, 43 and 44 wherein the crosslinking agent is selected from the group consisting of dihaloalkanes, haloalkyloxiranes, alkyloxirane sulfonates, di(haloalkyl)amines, tri(haloalkyl) amines, diepoxides, triepoxides, tetraepoxides, bis(halomethyl)benzenes, tri(halomethyl)benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol diglycidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy) diphenylmethane, bisphenol F diglycidyl ether, 1,4-bis(2',3'epoxypropyl) perfluoro-n-butane, 2,6-di(oxiran-2-ylmethyl)-1,2,3,5,6,7-hexahydropyrrolo[3,4-t]isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo [7,3,3,15,11]heptasiloxane, 4,4'methylenebis(N,N-diglycidylaniline), bis(halomethyl)benzene, bis(halomethyl)

biphenyl and bis(halomethyl)naphthalene, toluene diisocyanate, acrylol chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino)ethane, Bis(3-chloropropyl)amine, 1,3-Dichloro-2-propanol, 1,3-Dichloropropane, 1-chloro-2,3-epoxypropane, tris[(2-oxiranyl)methyl]amine, and combinations thereof.

Embodiment 46

The pharmaceutical composition of embodiment 39 wherein the preparation of the crosslinked amine polymer comprises radical polymerization of an amine monomer comprising at least one amine moiety or nitrogen containing moiety.

Embodiment 47

The pharmaceutical composition of any preceding embodiment wherein the crosslinked amine polymer has an equilibrium swelling ratio in deionized water of about 1.5 or less.

Embodiment 48

The pharmaceutical composition of any preceding embodiment wherein the crosslinked amine polymer has an equilibrium swelling ratio in deionized water of about 1 or less.

Embodiment 49

The pharmaceutical composition of any preceding embodiment wherein the crosslinked amine polymer has a chloride ion to phosphate ion binding molar ratio of at least 0.5:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

Embodiment 50

The pharmaceutical composition of any preceding embodiment wherein the crosslinked amine polymer has a chloride ion to phosphate ion binding molar ratio of at least 1:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

Embodiment 51

The pharmaceutical composition of any preceding embodiment wherein the crosslinked amine polymer has a chloride ion to phosphate ion binding molar ratio of at least 2:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

Embodiment 52

The pharmaceutical composition of any preceding embodiment wherein the crosslinked amine polymer has a proton binding capacity of at least 10 mmol/g and a chloride ion binding capacity of at least 10 mmol/g in an aqueous simulated gastric fluid buffer ("SGF") containing 35 mM NaCl and 63 mM HCl at pH 1.2 and 37° C.

Embodiment 53

The pharmaceutical composition of any preceding embodiment wherein the crosslinked amine polymer has an equilibrium proton binding capacity of at least 12 mmol/g and a chloride ion binding capacity of at least 12 mmol/g in an aqueous simulated gastric fluid buffer ("SGF") containing 35 mM NaCl and 63 mM HCl at pH 1.2 and 37° C.

Embodiment 54

The pharmaceutical composition of any preceding embodiment wherein the crosslinked amine polymer has an equilibrium proton binding capacity of at least 14 mmol/g and a chloride ion binding capacity of at least 14 mmol/g in an aqueous simulated gastric fluid buffer ("SGF") containing 35 mM NaCl and 63 mM HCl at pH 1.2 and 37° C.

Embodiment 55

The pharmaceutical composition of any preceding embodiment wherein the crosslinked amine polymer has a chloride binding capacity of at least 1 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 56

The pharmaceutical composition of any preceding embodiment wherein the crosslinked amine polymer has a chloride binding capacity of at least 2 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 57

The pharmaceutical composition of any preceding embodiment wherein the crosslinked amine polymer has a chloride binding capacity of at least 3 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 58

The pharmaceutical composition of any preceding embodiment wherein the crosslinked amine polymer has a chloride binding capacity of at least 4 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 59

The pharmaceutical composition of any preceding embodiment wherein the crosslinked amine polymer has a chloride binding capacity of at least 5 mmol/g in an aqueous simulated small intestine organic and inorganic buffer ("SOB") containing 50 mM 2-(N-morpholino)ethanesulfonic acid (MES), 50 mM sodium acetate, 36 mM sodium chloride, 7 mM sodium phosphate, 1.5 mM sodium citrate, 30 mM oleic acid and 5 mM sodium taurocholate, buffered to pH 6.2 and at 37° C.

Embodiment 60

The pharmaceutical composition of any preceding embodiment wherein the percentage of quaternized amines is less than 40%.

Embodiment 61

The pharmaceutical composition of any preceding embodiment wherein the percentage of quaternized amines is less than 30%.

Embodiment 62

The pharmaceutical composition of any preceding embodiment wherein the percentage of quaternized amines is less than 20%.

Embodiment 63

The pharmaceutical composition of any preceding embodiment wherein the percentage of quaternized amines is less than 10%.

Embodiment 64

The pharmaceutical composition of any preceding embodiment wherein the percentage of quaternized amines is less than 5%.

Embodiment 65

The pharmaceutical composition of any preceding embodiment wherein the crosslinked amine polymer is a gel or a bead having a mean particle size of 40 to 180 micrometers.

Embodiment 66

The pharmaceutical composition of any preceding embodiment wherein the crosslinked amine polymer is a gel or a bead having a mean particle size of 60 to 160 micrometers.

Embodiment 67

The pharmaceutical composition of any preceding embodiment wherein the crosslinked amine polymer is a gel or a bead having a mean particle size of 80 to 140 micrometers.

Embodiment 68

The pharmaceutical composition of any one of embodiments 65-67 wherein less than about 0.5 volume percent of the particles have a diameter of less than about 10 micrometers.

Embodiment 69

The pharmaceutical composition of any one of embodiments 65-67 wherein less than about 5 volume percent of the particles have a diameter of less than about 20 micrometers.

Embodiment 70

The pharmaceutical composition of any one of embodiments 65-67 wherein less than about 0.5 volume percent of the particles have a diameter of less than about 20 micrometers.

Embodiment 71

The pharmaceutical composition of any one of embodiments 65-67 wherein less than about 5 volume percent of the particles have a diameter of less than about 30 micrometers.

Embodiment 72

The pharmaceutical composition of any preceding embodiment in a dosage unit form.

Embodiment 73

The pharmaceutical composition of embodiment 72 wherein the dosage unit form is a capsule, tablet or sachet dosage form.

Embodiment 74

The pharmaceutical composition of any preceding embodiment wherein the pharmaceutical composition comprises a pharmaceutically acceptable carrier, excipient, or diluent.

Embodiment 75

A method of treating and acid/base disorder in an animal including a human by removing HCl through oral administration of a pharmaceutical composition of any of the preceding embodiments.

Embodiment 76

The method of treatment of embodiment 75 wherein the acid/base disorder is metabolic acidosis.

Embodiment 77

The method of treatment of embodiment 75 wherein the pH is controlled or normalized.

Embodiment 78

The method of treatment of embodiment 75 wherein the serum bicarbonate is controlled or normalized.

Embodiment 79

The method of treatment of embodiment 75 wherein less than 1 g of sodium or potassium is administered per day.

Embodiment 80

The method of treatment of embodiment 75 wherein less than 0.5 g of sodium or potassium is administered per day.

Embodiment 81

The method of treatment of embodiment 75 wherein less than 0.1 g of sodium or potassium is administered per day.

Embodiment 82

The method of treatment of embodiment 75 wherein no sodium or potassium is administered.

Embodiment 83

The method of treatment of embodiment 75 wherein the daily dose administered is less than 20 g.

Embodiment 84

The method of treatment of embodiment 75 wherein the daily dose administered is less than 15 g.

Embodiment 85

The method of treatment of embodiment 75 wherein the daily dose administered is less than 10 g.

Embodiment 86

The method of treatment of embodiment 75 wherein the daily dose administered is less than 5 g.

Embodiment 87

The method of treatment of embodiment 75 wherein the daily dose administered is less than 4 g.

Embodiment 88

The method of treatment of embodiment 75 wherein the daily dose administered is less than 3 g.

Embodiment 89

The method of treatment of embodiment 75 wherein the daily dose is administered once a day.

Embodiment 90

The method of treatment of embodiment 75 wherein the daily dose is administered twice a day.

Embodiment 91

The method of treatment of embodiment 75 wherein the daily dose is administered three times a day.

Embodiment 92

The method of treatment of embodiment 75 wherein the metabolic acidosis is acute metabolic acidosis.

Embodiment 93

The method of treatment of embodiment 75 wherein administration is chronic.

Embodiment 94

The method of treatment of embodiment 75 wherein the daily dose results in a sustained serum bicarbonate increase of 1.6 mEq/L.

Embodiment 95

The method of treatment of embodiment 75 wherein the daily dose results in a sustained serum bicarbonate increase of mEq/L.

Embodiment 96

The method of treatment of embodiment 75 wherein the daily dose results in a sustained serum bicarbonate increase of mEq/L.

Embodiment 97

The method of treatment of embodiment 75 wherein the daily dose results in a sustained serum bicarbonate increase of mEq/L.

Embodiment 98

The method of treatment of embodiment 75 wherein the daily dose results in a sustained serum bicarbonate increase of mEq/L.

Embodiment 99

The method of treatment of embodiment 75 wherein a daily dose of 10 g or less per day results in an increase in serum bicarbonate of mEq/L.

Embodiment 100

The method of treatment of embodiment 75 wherein a daily dose of 5 g or less per day results in an increase in serum bicarbonate of mEq/L.

Embodiment 101

The method of treatment of any of embodiments 83 to 99 and the dose is titrated based on the serum bicarbonate values of the patient in need of treatment or other indicators of acidosis.

Embodiment 102

The pharmaceutical composition of any of embodiments 1-74 wherein the crosslinked amine polymer retains 1 mmol/g chloride through the GI tract.

Embodiment 103

The pharmaceutical composition of any of embodiments 1-74 wherein the crosslinked amine polymer retains 2 mmol/g chloride through the GI tract.

Embodiment 104

The pharmaceutical composition of any of embodiments 1-74 wherein the crosslinked amine polymer retains 4 mmol/g chloride through the GI tract.

Embodiment 105

The pharmaceutical composition of any of embodiments 1-74 wherein the crosslinked amine polymer retains 8 mmol/g chloride through the GI tract.

Embodiment 106

The pharmaceutical composition of any of embodiments 1-74 wherein a dose of the pharmaceutical composition is titrated based on the serum bicarbonate values of a patient in need of treatment or other indicators of acidosis.

Embodiment 107

The pharmaceutical composition of any of embodiments 1-74 or the method of embodiments 75-101 wherein an aliphatic moiety is alkyl or alkenyl.

Embodiment 108

The pharmaceutical composition of any of embodiments 1-74 or the method of embodiments 75-101 wherein a heteroaliphatic moiety is a heteroalkyl or heteroalkenyl moiety.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

I. Preparation and Synthesis of Control Polymers

A. Free Amine Sevelamar

Renvela was obtained from commercial sources. Eighty-four sachets (i.e. 201.4 gm) of Renvela (sevelamer carbonate) were poured into a 5 L plastic beaker. Four liters of Milli-Q water were added to the beaker and the content was stirred using a magnetic stir plate and stir bar for 30 minutes. The content was then transferred in to a filter frit fitted with a P8 Whatman filter paper and excess supernatant was removed by applying negative vacuum. The steps of adding water, stirring, filtering and removing supernatant were repeated for a total of three times. After the final water wash, three liters of 1M sodium hydroxide were added to the beaker and stirred for 30 minutes. This was followed by vacuum filtering to remove excess sodium hydroxide. The steps of adding sodium hydroxide, stirring and vacuum filtering were repeated for a total of two sodium hydroxide washes. The polymer was then washed with Milli-Q water to remove excess sodium hydroxide. The pH of the filtrate was measured using pH strips, and the polymer was washed with water until the pH of the filtrate was 7 or less. The wet polymer was transferred into glass trays and frozen at −40° C. for 1 hour, and then lyophilized for 3-5 days to dry the polymer. The loss on drying of the polymer was measured using an A&D MX-50 moisture analyzer (standard mode, ramp to 130° C. and hold).

B. Bixalomer

Kiklin (Bixalomer) capsules were obtained from commercial sources and free amine polymer was isolated directly from the capsules without additional purification. Additional bixalomer reference material was prepared following information in the Kiklin product insert (prescription information) and procedures in U.S. Pat. No. 7,459,502. The bixalomer reference material used as a comparator in several examples below was prepared using an epichlorohydrin ("ECH") to 1,4-Bis[bis(3-aminopropyl)amino]butane ("C4A3BTA") molar ratio of 2.35 to 1, which falls within the acceptable range of 2.4:1 to 2:1 described in the Kiklin product insert and yielded a polymer with performance equivalent to Kiklin as measured in the Swelling and SGF assays described above. An aqueous stock solution was made by dissolving C4A3BTA (25.06 g), HCl (15.58 g conc. HCl), and Calimulse EM-99 (branched dodecylbenzene sulfonate, 1.39 g) in water (17.99 g). A 3-neck round bottom flask with four side baffles equipped with an overhead stirrer, a Dean Stark apparatus and condenser, and a nitrogen inlet was charged with the aqueous stock solution and toluene. The reaction mixture was stirred under inert atmosphere and heated to 80° C. ECH (17.47 g) was introduced as a 40 weight % solution in toluene which was added via syringe pump semi-continuously over the course of one hour. The reaction mixture was stirred for 30-45 minutes at 80° C., after which the bath temperature was increased to 110° C. for a final dehydration step. When 24 mL of water was collected, the flask was cooled to room temperature and the toluene was removed by filtration. The resultant polymer beads were purified by washing with toluene (100 mL, three times), 27 wt % HCl (50 mL, three times), water (100 mL, three times), a solution of 10:9:1 water:methanol:NaOH (100 mL, two times), water (100 mL, five times), methanol (50 mL, three times), 20 wt % NaOH (300 mL, two times), and water until the pH of solution after washing was 7. The beads were then dried in a lyophilizer for 48 hours. Swelling and SGF assays were used to determine the performance equivalence of the synthesized bixalomer polymer as compared to commercial Kiklin, which was used "as is" from the capsule as a reference for the performance of synthesized polymers.

II. Chemistry Examples

The following chemistry examples are presented in five categories based on the mechanism of polymerization used:

(a) substitution polymerization (condensation/step growth) gels
(b) substitution polymerization (condensation/step growth) beads
(c) radical polymerization (addition/chain growth) gels
(d) radical polymerization (addition/chain growth) beads
(e) post-polymerization crosslinking In each case, a general polymerization procedure is described and specific examples are called out with reference to tables of synthesis parameters that were varied within the general procedure. Tables of the physicochemical performance characteristics (SGF and swelling) of the resulting polymers are also provided.

A. Substitution Polymerization of Small Molecule Amines

Under stirring, amine monomer, crosslinker, solvent, and base or acid were added to a reaction vessel. Upon mixing, the solution was heated and stirred. After the reaction was complete, the reaction was allowed to cool. The gel was mechanically ground to a fine powder and purified and dried to constant weight. Examples of amines and crosslinkers that are suitable for the synthesis of polymers described in this example include, but are not limited to, the combinations of amines and crosslinkers shown in Table 4. Table 5 describes key physicochemical properties (i.e. SGF binding and swelling ratio) of the polymer examples shown in Table 4.

1. Specific Procedure for C2PW+DCP Gel

2-[Bis(2-aminoethyl)amino]ethanamine ("C2PW") (1.00 g), water (1.00 g), and sodium hydroxide (1.64 g) were added to a 20 mL scintillation vial equipped with a stir bar. Under vigorous stirring, a single aliquot of 1,3-Dichloropropane ("DCP") (2.32 g) was added. Upon mixing, the solution was heated to 80° C. and stirred vigorously for 16 hours. The reaction was allowed to cool to 25° C. and 10 mL of water was added to the solidified gel. The gel was mechanically ground to a fine powder. The resulting solution was centrifuged and the aqueous phase was decanted off. The resultant ground polymer gels were purified by washing with methanol (100 mL, two times), water (100 mL), 1M HCl (100 mL, two times), water (100 mL), 1M NaOH (100 mL, three times), and finally water until the pH of solution after washing was 7. This polymer is shown in Table 4 and Table 5 as polymer#37.

2. Specific Procedure for EDA3+BCPA Gel 1,2-Bis(2-aminoethylamino)ethane ("EDA3") (0.11 g), water (0.50 g), Bis(3-chloropropyl)amine ("BCPA") (0.50 g), and sodium hydroxide (0.19 g) were added to a 20 mL scintillation vial equipped with a stir bar. Upon mixing, the solution was heated to 80° C. and stirred vigorously for 16 hours. The reaction was allowed to cool to 25° C. and 10 mL of water was added to the solidified gel. The gel was mechanically ground to a fine powder. The resulting solution was centrifuged and the aqueous phase was decanted off. The resultant ground polymer gels were purified by washing with methanol (100 mL, two times), water (100 mL), 1M HCl (100 mL, two times), water (100 mL), 1M NaOH (100 mL, three times), and finally water until the pH of the solution after washing was 7. This polymer is shown in Table 4 and Table 5 as polymer#54.

3. Specific Procedure for C2PW+TGA Gel

C2PW (0.50 g) and water (0.75 g) were added to a 20 mL scintillation vial equipped with a stir bar. Under vigorous stirring, a single aliquot of Tris[(2-oxiranyl)methyl]amine ("TGA") (0.79 g) was added. Upon mixing, the solution was heated to 80° C. and stirred vigorously for 16 hours. The reaction was allowed to cool to 25° C. and 10 mL of water was added to the solidified gel. The gel was mechanically ground to a fine powder. The resulting solution was centrifuged and the aqueous phase was decanted off. The resultant ground polymer gels were purified by washing with methanol (100 mL, two times), water (100 mL), 1M HCl (100 mL, two times), water (100 mL), 1M NaOH (100 mL, three times), and finally water until the pH of solution after washing was 7. This polymer is shown in Table 4 and Table 5 as polymer#71.

TABLE 4

Synthesis of substitution polymerization (condensation/step growth) gels

| Polymer # | Amine | Crosslinker | Solvent | Amine (g) | Crosslinker (g) | Solvent (g) | 37% HCl (g) | NaOH (g) |
|---|---|---|---|---|---|---|---|---|
| 1 | PDA1 | ECH | Water | 0.27 | 0.50 | 0.50 | 0.00 | 0.00 |
| 2 | PDA1 | ECH | Water | 0.23 | 0.50 | 0.50 | 0.00 | 0.00 |
| 3 | PDA1 | ECH | Water | 0.20 | 0.50 | 0.50 | 0.00 | 0.00 |
| 4 | PDA1 | ECH | Water | 0.18 | 0.50 | 0.50 | 0.00 | 0.00 |
| 5 | PDA1 | ECH | Water | 0.16 | 0.50 | 0.50 | 0.00 | 0.00 |
| 6 | C4A3BTA | ECH | Water | 0.50 | 0.34 | 0.60 | 0.12 | 0.00 |
| 7 | C4A3BTA | ECH | Water | 0.50 | 0.48 | 0.60 | 0.12 | 0.00 |
| 8 | C4A3BTA | ECH | Water | 0.50 | 0.63 | 0.60 | 0.12 | 0.00 |
| 9 | C4A3BTA | ECH | Water | 0.50 | 0.77 | 0.60 | 0.12 | 0.00 |
| 10 | C4A3BTA | ECH | Water | 0.50 | 0.92 | 0.60 | 0.12 | 0.00 |
| 11 | C4A3BTA | ECH | Water | 0.50 | 1.07 | 0.60 | 0.12 | 0.00 |
| 12 | C4A3BTA | DCP | Water | 0.50 | 0.41 | 0.72 | 0.00 | 0.29 |
| 13 | C4A3BTA | DCP | Water | 0.50 | 0.50 | 0.72 | 0.00 | 0.35 |
| 14 | C4A3BTA | DCP | Water | 0.50 | 0.59 | 0.72 | 0.00 | 0.42 |
| 15 | C4A3BTA | DCP | Water | 0.50 | 0.68 | 0.72 | 0.00 | 0.48 |
| 16 | C4A3BTA | DCP | Water | 0.50 | 0.77 | 0.72 | 0.00 | 0.54 |
| 17 | C4A3BTA | DCP | Water | 0.50 | 0.95 | 0.72 | 0.00 | 0.67 |
| 18 | C4A3BTA | DCP | Water | 0.50 | 1.12 | 0.72 | 0.00 | 0.80 |
| 19 | C4A3BTA | DCP | Water | 0.50 | 1.30 | 0.72 | 0.00 | 0.92 |
| 20 | PDA1 | DCP | Water | 0.29 | 0.50 | 0.50 | 0.00 | 0.35 |
| 21 | PDA1 | DCP | Water | 0.16 | 0.50 | 0.52 | 0.00 | 0.35 |
| 22 | PDA1 | DCP | Water | 0.11 | 0.50 | 0.46 | 0.00 | 0.35 |
| 23 | PDA1 | DCP | Water | 0.08 | 0.50 | 0.44 | 0.00 | 0.35 |
| 24 | PDA1 | DCP | Water | 0.07 | 0.50 | 0.42 | 0.00 | 0.35 |
| 25 | PDA1 | DCP | Water | 0.06 | 0.50 | 0.41 | 0.00 | 0.35 |

TABLE 4-continued

Synthesis of substitution polymerization (condensation/step growth) gels

| Polymer # | Amine | Crosslinker | Solvent | Amine (g) | Crosslinker (g) | Solvent (g) | 37% HCl (g) | NaOH (g) |
|---|---|---|---|---|---|---|---|---|
| 26 | EDA1 | DCP | Water | 0.50 | 1.41 | 0.72 | 0.00 | 1.00 |
| 27 | EDA1 | DCP | Water | 0.50 | 1.65 | 0.72 | 0.00 | 1.17 |
| 28 | EDA1 | DCP | Water | 0.50 | 1.88 | 0.72 | 0.00 | 1.33 |
| 29 | EDA2 | DCP | Water | 0.50 | 0.82 | 0.72 | 0.00 | 0.58 |
| 30 | EDA2 | DCP | Water | 0.50 | 0.96 | 0.72 | 0.00 | 0.68 |
| 31 | EDA2 | DCP | Water | 0.50 | 1.10 | 0.72 | 0.00 | 0.78 |
| 32 | EDA3 | DCP | Water | 1.00 | 1.55 | 1.00 | 0.00 | 1.09 |
| 33 | EDA3 | DCP | Water | 1.00 | 1.93 | 1.00 | 0.00 | 1.37 |
| 34 | EDA3 | DCP | Water | 1.00 | 2.32 | 1.00 | 0.00 | 1.64 |
| 35 | EDA3 | DCP | Water | 1.00 | 2.70 | 1.00 | 0.00 | 1.91 |
| 36 | C2PW | DCP | Water | 1.00 | 1.93 | 1.00 | 0.00 | 1.37 |
| 37 | C2PW | DCP | Water | 1.00 | 2.32 | 1.00 | 0.00 | 1.64 |
| 38 | C2PW | DCP | Water | 1.00 | 2.70 | 1.00 | 0.00 | 1.91 |
| 39 | C2PW | DCP | Water | 1.00 | 3.09 | 1.00 | 0.00 | 2.19 |
| 40 | C2PW | DCP | Water | 1.00 | 3.48 | 1.00 | 0.00 | 2.46 |
| 41 | C2PW | DCP | Water | 1.00 | 3.86 | 1.00 | 0.00 | 2.74 |
| 42 | C4A3BTA | BCPA | Water | 0.26 | 0.50 | 0.50 | 0.00 | 0.19 |
| 43 | C4A3BTA | BCPA | Water | 0.15 | 0.50 | 0.50 | 0.00 | 0.19 |
| 44 | C4A3BTA | BCPA | Water | 0.11 | 0.50 | 0.50 | 0.00 | 0.19 |
| 45 | C4A3BTA | BCPA | Water | 0.09 | 0.50 | 0.50 | 0.00 | 0.19 |
| 46 | PDA1 | BCPA | Water/MeOH | 0.06 | 0.50 | 0.23/0.03 | 0.00 | 0.19 |
| 47 | PDA1 | BCPA | Water/MeOH | 0.05 | 0.50 | 0.22/0.02 | 0.00 | 0.19 |
| 48 | PDA1 | BCPA | Water/MeOH | 0.04 | 0.50 | 0.21/0.02 | 0.00 | 0.19 |
| 49 | C2PW | BCPA | Water | 0.09 | 0.50 | 0.50 | 0.00 | 0.19 |
| 50 | C2PW | BCPA | Water | 0.06 | 0.50 | 0.50 | 0.00 | 0.19 |
| 51 | C2PW | BCPA | Water | 0.04 | 0.50 | 0.50 | 0.00 | 0.19 |
| 52 | C2PW | BCPA | Water | 0.04 | 0.50 | 0.50 | 0.00 | 0.19 |
| 53 | EDA3 | BCPA | Water | 0.17 | 0.50 | 0.50 | 0.00 | 0.19 |
| 54 | EDA3 | BCPA | Water | 0.11 | 0.50 | 0.50 | 0.00 | 0.19 |
| 55 | EDA3 | BCPA | Water | 0.08 | 0.50 | 0.50 | 0.00 | 0.19 |
| 56 | EDA3 | BCPA | Water | 0.07 | 0.50 | 0.50 | 0.00 | 0.19 |
| 57 | C4A3BTA | BCPA | Water | 0.11 | 0.75 | 0.75 | 0.00 | 0.29 |
| 58 | C4A3BTA | BCPA | Water | 0.10 | 0.75 | 0.75 | 0.00 | 0.29 |
| 59 | C4A3BTA | BCPA | Water | 0.09 | 0.75 | 0.75 | 0.00 | 0.29 |
| 60 | EDA3 | BDE | Water | 0.50 | 1.13 | 0.50 | 0.00 | 0.00 |
| 61 | EDA3 | BDE | Water | 0.50 | 1.38 | 0.50 | 0.00 | 0.00 |
| 62 | EDA3 | BDE | Water | 0.50 | 1.63 | 0.50 | 0.00 | 0.00 |
| 63 | EDA3 | BDE | Water | 0.50 | 1.88 | 0.50 | 0.00 | 0.00 |
| 64 | C4A3BTA | TGA | Water | 0.50 | 0.29 | 0.75 | 0.00 | 0.00 |
| 65 | C4A3BTA | TGA | Water | 0.50 | 0.49 | 0.75 | 0.00 | 0.00 |
| 66 | C4A3BTA | TGA | Water | 0.50 | 0.68 | 0.75 | 0.00 | 0.00 |
| 67 | C4A3BTA | TGA | Water | 0.50 | 0.88 | 0.75 | 0.00 | 0.00 |
| 68 | PDA1 | TGA | Water | 0.33 | 0.50 | 0.50 | 0.00 | 0.00 |
| 69 | PDA1 | TGA | Water | 0.18 | 0.50 | 0.27 | 0.00 | 0.00 |
| 70 | PDA1 | TGA | Water | 0.13 | 0.50 | 0.19 | 0.00 | 0.00 |
| 71 | C2PW | TGA | Water | 0.50 | 0.79 | 0.75 | 0.00 | 0.00 |
| 72 | C2PW | TGA | Water | 0.50 | 1.11 | 0.75 | 0.00 | 0.00 |
| 73 | C2PW | TGA | Water | 0.50 | 1.42 | 0.75 | 0.00 | 0.00 |
| 74 | EDA3 | BCPA | Water | 0.06 | 0.75 | 0.75 | 0.00 | 0.29 |
| 75 | EDA3 | BCPA | Water | 0.06 | 0.75 | 0.75 | 0.00 | 0.29 |
| 76 | EDA3 | BCPA | Water | 0.05 | 0.75 | 0.75 | 0.00 | 0.29 |
| 77 | C2PW | BCPA | Water | 0.07 | 0.50 | 0.40 | 0.00 | 0.15 |
| 78 | C3PW | DCP | Water | 0.42 | 0.50 | 0.77 | 0.00 | 0.35 |
| 79 | C3PW | DCP | Water | 0.33 | 0.50 | 0.69 | 0.00 | 0.35 |
| 80 | C3PW | DCP | Water | 0.28 | 0.50 | 0.63 | 0.00 | 0.35 |
| 81 | C3PW | DCP | Water | 0.24 | 0.50 | 0.59 | 0.00 | 0.35 |
| 82 | C2PW | DC2OH | DMF | 1.00 | 1.32 | 3.00 | 0.00 | 0.00 |
| 83 | C2PW | DC2OH | DMF | 1.00 | 2.21 | 3.00 | 0.00 | 0.00 |
| 84 | C2PW | DC2OH | DMF | 1.00 | 2.64 | 3.00 | 0.00 | 0.00 |
| 85 | C2PW | DC2OH | DMF | 1.00 | 3.09 | 3.00 | 0.00 | 0.00 |
| 86 | C2PW | ECH | Water | 1.00 | 1.58 | 1.50 | 0.00 | 0.00 |
| 87 | C2PW | ECH | Water | 1.00 | 1.90 | 1.50 | 0.00 | 0.00 |
| 88 | C2PW | ECH | Water | 1.00 | 2.21 | 1.50 | 0.00 | 0.00 |
| 89 | C2A3BTA | ECH | Water | 0.50 | 0.51 | 0.21 | 0.39 | 0.00 |
| 90 | C2A3BTA | ECH | Water | 0.50 | 0.66 | 0.21 | 0.39 | 0.00 |
| 91 | C2A3BTA | ECH | Water | 0.50 | 0.82 | 0.21 | 0.39 | 0.00 |
| 92 | C2A3G2 | ECH | Water | 0.50 | 0.41 | 1.43 | 0.08 | 0.00 |
| 93 | C2A3G2 | ECH | Water | 0.50 | 0.55 | 1.43 | 0.08 | 0.00 |
| 94 | C2A3G2 | ECH | Water | 0.50 | 0.69 | 1.43 | 0.08 | 0.00 |

TABLE 5

Properties of substitution polymerization (condensation/step growth) gels

| Polymer # | Amine | Crosslinker | Weight % Crosslinker | MW/N | Theoretical Capacity (mmol/g) | SGF Cl (mmol/g) | Swelling |
|---|---|---|---|---|---|---|---|
| 1 | PDA1 | ECH | 54.7% | 79.6 | 12.6 | 12.4 | 1.8 |
| 2 | PDA1 | ECH | 58.5% | 86.9 | 11.5 | 11.0 | 1.4 |
| 3 | PDA1 | ECH | 61.7% | 94.1 | 10.6 | 10.0 | 1.6 |
| 4 | PDA1 | ECH | 64.4% | 101.4 | 9.9 | 9.8 | 1.4 |
| 5 | PDA1 | ECH | 66.8% | 108.7 | 9.2 | 9.3 | 1.8 |
| 6 | C4A3BTA | ECH | 29.7% | 74.9 | 13.3 | 13.4 | 1.9 |
| 7 | C4A3BTA | ECH | 37.8% | 84.6 | 11.8 | 11.8 | 1.4 |
| 8 | C4A3BTA | ECH | 44.1% | 94.3 | 10.6 | 10.7 | 1.5 |
| 9 | C4A3BTA | ECH | 49.3% | 104.0 | 9.6 | 10.0 | 1.3 |
| 10 | C4A3BTA | ECH | 53.7% | 113.7 | 8.8 | 9.2 | 1.6 |
| 11 | C4A3BTA | ECH | 57.3% | 123.3 | 8.1 | 8.8 | 1.9 |
| 12 | C4A3BTA | DCP | 23.4% | 68.8 | 14.5 | 14.7 | 1.7 |
| 13 | C4A3BTA | DCP | 27.2% | 72.3 | 13.8 | 14.5 | 1.4 |
| 14 | C4A3BTA | DCP | 30.5% | 75.8 | 13.2 | 13.5 | 1.7 |
| 15 | C4A3BTA | DCP | 33.6% | 79.3 | 12.6 | 12.8 | 1.6 |
| 16 | C4A3BTA | DCP | 36.4% | 82.8 | 12.1 | 11.9 | 1.8 |
| 17 | C4A3BTA | DCP | 41.4% | 89.8 | 11.1 | 10.6 | 1.2 |
| 18 | C4A3BTA | DCP | 45.6% | 96.9 | 10.3 | 10.9 | 1.8 |
| 19 | C4A3BTA | DCP | 49.3% | 103.9 | 9.6 | 9.0 | 1.6 |
| 20 | PDA1 | DCP | 50.5% | 72.9 | 13.7 | 12.9 | 4.1 |
| 21 | PDA1 | DCP | 53.9% | 78.1 | 12.8 | 13.0 | 1.8 |
| 22 | PDA1 | DCP | 63.6% | 99.2 | 10.1 | 11.4 | 1.4 |
| 23 | PDA1 | DCP | 70.0% | 120.2 | 8.3 | 9.6 | 1.6 |
| 24 | PDA1 | DCP | 74.5% | 141.3 | 7.1 | 9.2 | 2.4 |
| 25 | PDA1 | DCP | 77.8% | 162.3 | 6.2 | 8.3 | 2.9 |
| 26 | EDA1 | DCP | 51.2% | 61.6 | 16.2 | 12.1 | 3.4 |
| 27 | EDA1 | DCP | 55.1% | 66.9 | 15.0 | 13.0 | 2.5 |
| 28 | EDA1 | DCP | 58.3% | 72.1 | 13.9 | 10.7 | 2.5 |
| 29 | EDA2 | DCP | 41.6% | 58.9 | 17.0 | 13.7 | 2.8 |
| 30 | EDA2 | DCP | 47.9% | 66.0 | 15.2 | 11.8 | 2.5 |
| 31 | EDA2 | DCP | 52.9% | 73.0 | 13.7 | 10.9 | 2.3 |
| 32 | EDA3 | DCP | 36.5% | 57.6 | 17.4 | 11.8 | 2.1 |
| 33 | EDA3 | DCP | 41.8% | 62.9 | 15.9 | 11.5 | 2.9 |
| 34 | EDA3 | DCP | 46.3% | 68.1 | 14.7 | 10.6 | 2.5 |
| 35 | EDA3 | DCP | 50.2% | 73.4 | 13.6 | 10.0 | 2.5 |
| 36 | C2PW | DCP | 41.8% | 62.9 | 15.9 | 13.2 | 2.2 |
| 37 | C2PW | DCP | 46.3% | 68.1 | 14.7 | 12.1 | 2.4 |
| 38 | C2PW | DCP | 50.2% | 73.4 | 13.6 | 11.1 | 2.0 |
| 39 | C2PW | DCP | 53.5% | 78.6 | 12.7 | 10.1 | 1.6 |
| 40 | C2PW | DCP | 56.4% | 83.9 | 11.9 | 9.4 | 1.6 |
| 41 | C2PW | DCP | 59.0% | 89.2 | 11.2 | 8.8 | 2.1 |
| 42 | C4A3BTA | BCPA | 48.5% | 68.2 | 14.7 | 15.2 | 3.4 |
| 43 | C4A3BTA | BCPA | 61.1% | 73.8 | 13.5 | 13.5 | 2.3 |
| 44 | C4A3BTA | BCPA | 68.7% | 77.7 | 12.9 | 12.9 | 2.0 |
| 45 | C4A3BTA | BCPA | 73.9% | 80.6 | 12.4 | 11.6 | 1.8 |
| 46 | PDA1 | BCPA | 80.5% | 73.9 | 13.5 | 13.8 | 2.6 |
| 47 | PDA1 | BCPA | 84.6% | 78.1 | 12.8 | 12.9 | 2.4 |
| 48 | PDA1 | BCPA | 87.3% | 81.1 | 12.3 | 12.1 | 1.8 |
| 49 | C2PW | BCPA | 73.1% | 67.9 | 14.7 | 12.7 | 2.0 |
| 50 | C2PW | BCPA | 80.3% | 74.1 | 13.5 | 12.2 | 1.5 |
| 51 | C2PW | BCPA | 84.4% | 78.3 | 12.8 | 11.4 | 1.3 |
| 52 | C2PW | BCPA | 87.2% | 81.3 | 12.3 | 10.9 | 1.3 |
| 53 | EDA3 | BCPA | 67.0% | 63.4 | 15.8 | 10.0 | 3.3 |
| 54 | EDA3 | BCPA | 75.3% | 69.7 | 14.3 | 10.3 | 2.9 |
| 55 | EDA3 | BCPA | 80.3% | 74.1 | 13.5 | 12.2 | 3.3 |
| 56 | EDA3 | BCPA | 83.6% | 77.4 | 12.9 | 10.6 | 2.9 |
| 57 | C4A3BTA | BCPA | 76.7% | 82.3 | 12.2 | 11.8 | 1.8 |
| 58 | C4A3BTA | BCPA | 79.0% | 83.7 | 12.0 | 12.0 | 1.4 |
| 59 | C4A3BTA | BCPA | 80.9% | 84.9 | 11.8 | 10.9 | 1.5 |
| 60 | EDA3 | BDE | 57.0% | 85.0 | 11.8 | 6.2 | 1.5 |
| 61 | EDA3 | BDE | 61.8% | 95.7 | 10.4 | 5.4 | 1.9 |
| 62 | EDA3 | BDE | 65.7% | 106.5 | 9.4 | 5.1 | 1.9 |
| 63 | EDA3 | BDE | 68.8% | 117.27 | 8.53 | 4.3 | 1.6 |
| 64 | C4A3BTA | TGA | 37.0% | 71.60 | 13.97 | 12.4 | 3.1 |
| 65 | C4A3BTA | TGA | 49.3% | 81.39 | 12.29 | 11.3 | 2.0 |
| 66 | C4A3BTA | TGA | 57.7% | 89.74 | 11.14 | 9.6 | 1.7 |
| 67 | C4A3BTA | TGA | 63.7% | 96.85 | 10.33 | 9.2 | 1.5 |
| 68 | PDA1 | TGA | 60.7% | 70.47 | 14.19 | 11.7 | 4.7 |
| 69 | PDA1 | TGA | 73.9% | 88.98 | 11.24 | 9.4 | 1.4 |
| 70 | PDA1 | TGA | 80.4% | 102.35 | 9.77 | 8.3 | 1.2 |
| 71 | C2PW | TGA | 61.3% | 71.95 | 13.90 | 10.0 | 1.7 |
| 72 | C2PW | TGA | 68.9% | 81.80 | 12.22 | 8.6 | 1.4 |
| 73 | C2PW | TGA | 74.0% | 90.08 | 11.10 | 7.6 | 1.3 |
| 74 | EDA3 | BCPA | 85.2% | 79.14 | 12.64 | 10.3 | 1.6 |

TABLE 5-continued

Properties of substitution polymerization (condensation/step growth) gels

| Polymer # | Amine | Crosslinker | Weight % Crosslinker | MW/N | Theoretical Capacity (mmol/g) | SGF Cl (mmol/g) | Swelling |
|---|---|---|---|---|---|---|---|
| 75 | EDA3 | BCPA | 86.6% | 80.63 | 12.40 | 9.9 | 1.9 |
| 76 | EDA3 | BCPA | 87.7% | 81.90 | 12.21 | 9.3 | 1.6 |
| 77 | C2PW | BCPA | 77.2% | 71.35 | 14.02 | 11.5 | 2.2 |
| 78 | C3PW | DCP | 30.9% | 68.10 | 14.70 | 16.0 | 2.2 |
| 79 | C3PW | DCP | 35.8% | 73.40 | 13.60 | 15.3 | 1.9 |
| 80 | C3PW | DCP | 40.1% | 78.60 | 12.70 | 14.8 | 1.9 |
| 81 | C3PW | DCP | 43.9% | 83.90 | 11.90 | 14.3 | 2.0 |
| 82 | C2PW | DC2OH | 37.3% | 58.34 | 17.14 | 11.5 | 4.2 |
| 83 | C2PW | DC2OH | 49.8% | 72.86 | 13.73 | 10.1 | 3.4 |
| 84 | C2PW | DC2OH | 54.4% | 80.12 | 12.48 | 9.4 | 3.1 |
| 85 | C2PW | DC2OH | 58.2% | 87.38 | 11.44 | 9.1 | 3.6 |
| 86 | C2PW | ECH | 49.8% | 72.86 | 13.73 | 9.1 | 1.7 |
| 87 | C2PW | ECH | 54.4% | 80.12 | 12.48 | 8.5 | 1.6 |
| 88 | C2PW | ECH | 58.2% | 87.38 | 11.44 | 7.8 | 1.8 |
| 89 | C2A3BTA | ECH | 40.0% | 79.9 | 12.5 | 11.4 | 1.9 |
| 90 | C2A3BTA | ECH | 46.4% | 89.6 | 11.2 | 10.9 | 1.8 |
| 91 | C2A3BTA | ECH | 51.7% | 99.3 | 10.1 | 10.0 | 1.8 |
| 92 | C2A3G2 | ECH | 33.8% | 73.9 | 13.5 | 10.4 | 2.4 |
| 93 | C2A3G2 | ECH | 40.8% | 82.6 | 12.1 | 8.1 | 2.0 |
| 94 | C2A3G2 | ECH | 46.4% | 91.3 | 11.0 | 7.3 | 2.3 |

B. General Polymerization Procedure for Beads Formed by Substitution Polymerization of Small Molecule Amines An aqueous stock solution was made by dissolving amine monomer and surfactant in water. In some instances, HCl was added to the aqueous stock solution. A reactor equipped with an overhead stirrer was charged with aqueous stock solution and organic solvent. Crosslinker was introduced in one of two methods. In the first method, crosslinker was introduced as part of the aqueous solution before mixing with the organic solvent. In the second method, after beginning to heat the reactor charged with aqueous stock solution and organic solvent, crosslinker was introduced via syringe pump semi-continuously over the course of several hours. After the reaction was complete, the organic solvent was removed and the beads were purified by washing the beads with different solvents. The beads were then dried to constant weight in a lyophilizer. This procedure applies to linear and branched amines and crosslinkers with and without an HCl binding functional group such as an amine ("active" and "passive" crosslinkers, respectively). Examples of amines and crosslinkers that are suitable for the synthesis of polymers described in this example include, but are not limited to, the combinations of amines and crosslinkers shown in Table 6. Table 7 describes key physicochemical properties (i.e. SGF binding and swelling ratio) of the polymer examples shown in Table 6.

1. Specific Procedure for C4A3BTA+ECH Beads

An aqueous stock solution was made by dissolving 1,4-Bis[bis(3-aminopropyl)amino]butane ("C4A3BTA") (10.02 g), HCl (6.25 g conc. HCl), and Calimulse EM-99 (branched dodecylbenzene sulfonate, 0.56 g) in water (7.18 g). Round bottom flasks equipped with an overhead stirrer and condenser were charged with aqueous stock solution and toluene. The reaction mixture was stirred under inert atmosphere and heated to 80° C. Epichlorohydrin ("ECH") (21.37 g) was introduced as a 40 weight % solution in toluene, which was added via syringe pump semi-continuously over the course of one hour. The reaction mixture was stirred for 16 hours at 80° C., after which the reaction mixture was cooled to room temperature and removed from the reactor. The toluene was removed by decanting, and the resultant polymer beads were purified by washing with methanol (100 mL, two times), water (100 mL), 1M HCl (100 mL, two times), water (100 mL), 1M NaOH (100 mL, three times), and water until the pH of solution after washing was 7. This polymer is shown in Table 6 and Table 7 as polymer number 21.

TABLE 6

Synthesis of substitution polymerization (condensation/step growth) beads

| Polymer # | Amine | Crosslinker | Solvent | Surfactant | Amine (g) | Crosslinker (g) | Solvent (g) | Water (g) | Surfactant (g) | 37% HCl (g) | NaOH (g) |
|---|---|---|---|---|---|---|---|---|---|---|---|
| 1 | EDA3 | ECH | Toluene | EM-99 | 3.75 | 7.12 | 64.88 | 7.50 | 0.40 | 0.00 | 0.00 |
| 2 | EDA3 | ECH | Toluene | EM-99 | 3.75 | 8.30 | 64.88 | 7.50 | 0.40 | 0.00 | 0.00 |
| 3 | C2PW | ECH | Toluene | EM-99 | 3.75 | 5.93 | 64.88 | 7.50 | 0.40 | 0.00 | 0.00 |
| 4 | C2PW | ECH | Toluene | EM-99 | 3.75 | 7.12 | 64.88 | 7.50 | 0.40 | 0.00 | 0.00 |
| 5 | C2PW | ECH | Toluene | EM-99 | 3.75 | 8.30 | 64.88 | 7.50 | 0.40 | 0.00 | 0.00 |
| 6 | PDA1 | ECH | Toluene | EM-99 | 3.00 | 7.49 | 51.90 | 6.00 | 0.32 | 0.00 | 0.00 |
| 7 | PDA1 | ECH | Toluene | EM-99 | 3.00 | 8.43 | 51.90 | 6.00 | 0.32 | 0.00 | 0.00 |
| 8 | PDA1 | ECH | Toluene | EM-99 | 3.00 | 9.36 | 51.90 | 6.00 | 0.32 | 0.00 | 0.00 |
| 9 | PDA1 | DC2OH | Toluene | EM-99 | 3.00 | 10.44 | 74.74 | 18.36 | 0.53 | 0.00 | 6.46 |
| 10 | PDA2 | ECH | Toluene | EM-99 | 4.00 | 4.23 | 69.20 | 8.00 | 0.43 | 0.00 | 0.00 |
| 11 | PDA2 | ECH | Toluene | EM-99 | 4.00 | 7.05 | 69.20 | 8.00 | 0.43 | 0.00 | 0.00 |

TABLE 6-continued

Synthesis of substitution polymerization (condensation/step growth) beads

| Polymer # | Amine | Crosslinker | Solvent | Surfactant | Amine (g) | Crosslinker (g) | Solvent (g) | Water (g) | Surfactant (g) | 37% HCl (g) | NaOH (g) |
|---|---|---|---|---|---|---|---|---|---|---|---|
| 12 | PDA2 | ECH | Toluene | EM-99 | 4.00 | 8.46 | 69.20 | 8.00 | 0.43 | 0.00 | 0.00 |
| 13 | EDA1 | ECH | Toluene | EM-99 | 2.00 | 6.15 | 52.02 | 6.00 | 0.21 | 0.00 | 0.00 |
| 14 | EDA1 | ECH | Toluene | EM-99 | 2.00 | 7.70 | 52.02 | 6.00 | 0.21 | 0.00 | 0.00 |
| 15 | C4A3BTA | ECH | Toluene | EM-99 | 10.03 | 7.32 | 73.38 | 7.42 | 0.57 | 6.24 | 0.00 |
| 16 | C4A3BTA | ECH | Toluene | EM-99 | 10.05 | 8.48 | 75.12 | 7.23 | 0.57 | 6.26 | 0.00 |
| 17 | C4A3BTA | ECH | Toluene | EM-99 | 10.02 | 9.08 | 86.61 | 7.17 | 0.56 | 6.27 | 0.00 |
| 18 | C4A3BTA | ECH | Toluene | EM-99 | 10.00 | 11.40 | 93.43 | 6.58 | 0.56 | 6.22 | 0.00 |
| 19 | C4A3BTA | ECH | Toluene | EM-99 | 10.01 | 15.52 | 85.68 | 7.20 | 0.56 | 6.27 | 0.00 |
| 20 | C4A3BTA | ECH | Toluene | EM-99 | 10.02 | 18.44 | 90.06 | 7.15 | 0.56 | 6.26 | 0.00 |
| 21 | C4A3BTA | ECH | Toluene | EM-99 | 10.02 | 21.37 | 94.46 | 7.18 | 0.56 | 6.25 | 0.00 |
| 22 | C2A3BTA | ECH | Toluene | EM-99 | 1.25 | 1.32 | 67.14 | 7.74 | 0.23 | 0.86 | 0.00 |
| 23 | C2A3BTA | ECH | Toluene | EM-99 | 1.25 | 1.72 | 67.14 | 7.74 | 0.23 | 0.86 | 0.00 |
| 24 | C2A3BTA | ECH | Toluene | EM-99 | 1.25 | 1.93 | 67.14 | 7.74 | 0.23 | 0.86 | 0.00 |
| 25 | C2A3BTA | ECH | Toluene | EM-99 | 1.25 | 2.13 | 67.14 | 7.74 | 0.23 | 0.86 | 0.00 |
| 26 | C2A3BTA | ECH | Toluene | EM-99 | 1.25 | 2.53 | 67.14 | 7.74 | 0.23 | 0.86 | 0.00 |
| 27 | C2A3BTA | ECH | Toluene | EM-99 | 1.25 | 2.93 | 67.14 | 7.74 | 0.23 | 0.86 | 0.00 |

TABLE 7

Properties of substitution polymerization (condensation/step growth) beads

| Polymer # | Element | Amine | Crosslinker | Weight % Crosslinker | MW/N | Theoretical Capacity (mmol/g) | SGF Cl (mmol/g) | Swelling |
|---|---|---|---|---|---|---|---|---|
| 1 | A4 | EDA3 | ECH | 54.4% | 80.1 | 12.5 | 8.4 | 3.4 |
| 2 | A5 | EDA3 | ECH | 58.2% | 87.4 | 11.4 | 7.9 | 2.9 |
| 3 | A3 | C2PW | ECH | 49.8% | 72.9 | 13.7 | 11.0 | 2.3 |
| 4 | A4 | C2PW | ECH | 54.4% | 80.1 | 12.5 | 9.8 | 1.8 |
| 5 | A5 | C2PW | ECH | 58.2% | 87.4 | 11.4 | 8.1 | 2.0 |
| 6 | A4 | PDA1 | ECH | 61.7% | 94.1 | 10.6 | 10.9 | 1.6 |
| 7 | A5 | PDA1 | ECH | 64.4% | 101.4 | 9.9 | 10.2 | 1.5 |
| 8 | A6 | PDA1 | ECH | 66.8% | 108.7 | 9.2 | 9.9 | 1.4 |
| 9 | A2 | PDA1 | DC2OH | 61.7% | 94.1 | 10.6 | 8.7 | 3.5 |
| 10 | A1 | PDA2 | ECH | 39.9% | 72.8 | 13.7 | 11.9 | 3.2 |
| 11 | A3 | PDA2 | ECH | 52.5% | 92.1 | 10.9 | 10.9 | 2.7 |
| 12 | A4 | PDA2 | ECH | 57.0% | 101.8 | 9.8 | 10.1 | 2.9 |
| 13 | A3 | EDA1 | ECH | 65.9% | 88.1 | 11.3 | 10.1 | 3.5 |
| 14 | A4 | EDA1 | ECH | 70.7% | 102.7 | 9.7 | 9.0 | 2.0 |
| 15 | A1 | C4A3BTA | ECH | 31.5% | 76.9 | 13.0 | 12.6 | 2.0 |
| 16 | A1 | C4A3BTA | ECH | 34.8% | 80.7 | 12.4 | 13.4 | 1.9 |
| 17 | A1 | C4A3BTA | ECH | 36.3% | 82.7 | 12.1 | 11.7 | 1.6 |
| 18 | A1 | C4A3BTA | ECH | 41.8% | 90.4 | 11.1 | 12.2 | 1.9 |
| 19 | A1 | C4A3BTA | ECH | 49.3% | 104.0 | 9.6 | 11.0 | 0.9 |
| 20 | A1 | C4A3BTA | ECH | 53.7% | 113.7 | 8.8 | 8.9 | 1.1 |
| 21 | A1 | C4A3BTA | ECH | 57.3% | 123.3 | 8.1 | 8.2 | 1.2 |
| 22 | A3 | C2A3BTA | ECH | 40.0% | 79.9 | 12.5 | 12.8 | 3.5 |
| 23 | A4 | C2A3BTA | ECH | 46.4% | 89.6 | 11.2 | 12.4 | 2.9 |
| 24 | A1 | C2A3BTA | ECH | 49.2% | 94.5 | 10.6 | 12.3 | 3.7 |
| 25 | A2 | C2A3BTA | ECH | 51.7% | 99.3 | 10.1 | 11.5 | 3.1 |
| 26 | A3 | C2A3BTA | ECH | 56.0% | 109.0 | 9.2 | 11.4 | 1.8 |
| 27 | A4 | C2A3BTA | ECH | 59.5% | 118.7 | 8.4 | 10.6 | 1.8 |

C. General Polymerization Procedure for Gels Formed by Radical Polymerization (Addition/Chain Growth)

An aqueous solution of monoallylamine hydrochloride, multiallylamine crosslinker, and a radical initiator was placed into a reaction vessel. The reaction mixture was heated, after which the vessel was cooled to room temperature. The resulting polymer gel was swollen in water and ground to a fine powder. The resultant gel was purified by washing and then dried to a constant weight. Examples of amines that are suitable for the synthesis of polymers described in this example include, but are not limited to, the amines shown in Table 8. Table 9 describes key physicochemical properties (i.e. SGF binding and swelling ratio) of the polymer examples shown in Table 8.

1. Specific Procedure for AAH+TAA Gel

A round bottom flask in a parallel reactor equipped with a magnetic stir bar and nitrogen inlet was charged with water (2.14 g), allylamine hydrochloride (1-(Allylamino)-2-aminoethane, "AAH") (0.55 g), triallylamine ("TAA") (0.71 g), concentrated HCl (0.15 g), and V-50 (2,2'-Azobis(2-methylpropionamidine)dihydrochloride) (0.068 g). The reaction mixture was sparged with nitrogen for 15 minutes and heated to 80° C. under inert atmosphere. After 16 hours, the vessel was cooled to room temperature and removed from the reactor. The polymer gel was swollen in water and mechanically ground. The resultant fine powder was purified by washing with methanol (100 mL, two times), water (100 mL), 1M HCl (100 mL, two times), water (100 mL), 1M NaOH (100 mL, three times), and water until the pH of solution after washing was 7. The gel was dried in a lyophilizer for 48 h. This polymer is shown in Table 8 and Table 9 as polymer number 10.

2. Specific Procedure for AAH+DAEDA1 Gel

A round bottom flask in a parallel reactor equipped with a magnetic stir bar and nitrogen inlet was charged with water (2.53 g), allylamine hydrochloride (1-(Allylamino)-2-aminoethane, "AAH") (0.54 g), 1,2-Bis(allylamino)ethane ("DAEDA1") (0.86 g), and V-50 (2,2'-Azobis(2-methylpropionamidine)dihydrochloride) (0.067 g). The reaction mixture was sparged with nitrogen for 15 minutes and then heated to 80° C. under inert atmosphere. After 16 hours, the vessel was cooled to room temperature and removed from the reactor. The polymer gel was swollen in water and mechanically ground. The resultant fine powder was purified by washing with methanol (100 mL, two times), water (100 mL), 1M HCl (100 mL, two times), water (100 mL), 1M NaOH (100 mL, three times), and water until the pH of solution after washing was 7. The gel was dried in a lyophilizer for 48 hours. This polymer is shown in Table 8 and Table 9 as polymer number 2.

organic suspending solvent. A solution of radical initiator was prepared. The two mixtures were independently sparged with nitrogen. The initiator solution was added to the reaction mixture, and subsequently heated for up to 16 hours. A second portion of initiator be added to the reaction mixture if necessary depending on the polymerization kinetics. The reaction mixture can also involve a dehydration step to yield a more concentrated reaction mixture and polymerize less active monomers and crosslinkers. After cooling the vessel to room temperature, the organic phase was removed and the beads were purified. The beads were dried. Examples of amines and crosslinkers that are suitable for the synthesis of polymers described in this example include, but are not limited to, the combinations of amines and crosslinkers shown in Table 10 part 1. These beads were then subjected to post-polymerization crosslinking procedures as described in E, below and in Table 10 part 2.

1. Specific Procedure for AAH+DAEDA1 Beads

An aqueous stock solution was prepared by dissolving allylamine hydrochloride (1-(Allylamino)-2-aminoethane, "AAH") (10.94 g) and 1,2-Bis(allylamino)ethane ("DAEDA1") (6.23 g) in water (38.89 g). A 3-neck round bottom flask with four side baffles equipped with an overhead stirrer, Dean Stark apparatus and condenser, and nitro-

TABLE 8

Synthesis of radical polymerization (addition/chain growth) gels

| Polymer # | Amine | Crosslinker | Amine (g) | Crosslinker (g) | Water (g) | V-50 (g) | 37% HCl (g) |
|---|---|---|---|---|---|---|---|
| 1 | AAH | DAEDA1 | 0.66 | 0.74 | 2.53 | 0.071 | 0.00 |
| 2 | AAH | DAEDA1 | 0.54 | 0.86 | 2.53 | 0.067 | 0.00 |
| 3 | AAH | DAPDA | 0.57 | 0.69 | 2.28 | 0.062 | 0.00 |
| 4 | AAH | DAPDA | 0.46 | 0.80 | 2.28 | 0.057 | 0.00 |
| 5 | AAH | DAPDA | 0.37 | 0.89 | 2.29 | 0.053 | 0.00 |
| 6 | AAH | DAPDA | 0.32 | 0.94 | 2.29 | 0.051 | 0.00 |
| 7 | AAH | DAPDA | 0.19 | 1.07 | 2.29 | 0.046 | 0.00 |
| 8 | AAH | TAA | 0.78 | 0.48 | 2.17 | 0.076 | 0.10 |
| 9 | AAH | TAA | 0.66 | 0.61 | 2.15 | 0.072 | 0.13 |
| 10 | AAH | TAA | 0.55 | 0.71 | 2.14 | 0.068 | 0.15 |

V-50 = 2,2'-Azobis(2-methylpropionamidine)dihydrochloride

TABLE 9

Properties of radical polymerization (addition/chain growth) gels

| Polymer # | Amine | Crosslinker | Weight % Crosslinker | MW/N | Theoretical Capacity (mmol/g) | SGF Cl (mmol/g) | Swelling |
|---|---|---|---|---|---|---|---|
| 1 | AAH | TAA | 44.5% | 61.7 | 16.2 | 10.6 | 3.6 |
| 2 | AAH | DAEDA1 | 63.1% | 64.6 | 15.5 | 15.5 | 3.2 |
| 3 | AAH | DAPDA | 57.1% | 67.0 | 14.9 | 14.6 | 2.7 |
| 4 | AAH | DAPDA | 65.3% | 68.7 | 14.6 | 14.2 | 4.0 |
| 5 | AAH | DAPDA | 73.0% | 70.4 | 14.2 | 14.0 | 4.8 |
| 6 | AAH | DAPDA | 76.8% | 71.3 | 14.0 | 13.7 | 4.5 |
| 7 | AAH | DAPDA | 86.3% | 73.6 | 13.6 | 13.3 | 4.6 |
| 8 | AAH | TAA | 44.5% | 61.7 | 16.2 | 11.3 | 3.4 |
| 9 | AAH | TAA | 54.2% | 62.8 | 15.9 | 9.8 | 2.3 |
| 10 | AAH | TAA | 62.6% | 63.8 | 15.7 | 8.9 | 1.9 |

D. General Polymerization Procedure for Beads Formed by Radical Polymerization (Addition/Chain Growth)

An aqueous stock solution was prepared by dissolving a monoallylamine and a multiallylamine crosslinker in water. A reactor equipped with a stirrer was charged with aqueous stock solution and surfactant dissolved in a hydrophobic gen inlet, was charged with aqueous stock solution and surfactant (Calimulse EM-99, branched dodecylbenzene sulfonate, 3.14 g) dissolved in a 74:26 chlorobenzene/heptane solution (311.11 g). In a separate vessel, a solution of V-50 (1.98 g) in water (12.75 g) was prepared. The two mixtures were independently sparged with nitrogen. Under inert atmosphere, the initiator solution was added to the reaction mixture, and subsequently heated to 67° C. for 16 hours. A second portion of initiator solution (14.73 g) and the reaction mixture were degassed and combined before increasing the temperature to 115° C. for a final dehydration step. After cooling the vessel to room temperature, the organic phase was removed by decanting, and the beads were purified by washing with methanol (100 mL, two times), water (100 mL), 2 M NaOH (100 mL), and water (100 mL, two times). The beads were dried in a lyophilizer for 48 hours. This polymer is shown in Table 10_1 and was the source bead for postpolymerization crosslinking that resulted in polymers 29-31 in Table 10 Part 2.

E. General Procedure of Post-Polymerization Crosslinking of Polyamine Beads or Gels Crosslinked polyamine beads or gels can be obtained from either crosslinking of linear polyamines, radical polymerization and crosslinking or small molecule amine crosslinking via a substitution reaction.

As a general example of polyamine bead synthesis, a stock solution of linear polyamine hydrochloride (and optionally sodium hydroxide) and water soluble crosslinker in water was prepared. Under inert atmosphere, a flask with an overhead stirrer was charged with each the aqueous and organic stock solutions. After initiating stirring, the reaction was heated up to 16 hours. Optionally a dehydrating procedure/step can be added to concentrate the reaction mixture. The hydrophobic organic solvent was removed by decanting, and the beads were purified by washing in solvents chosen to remove impurities. The resulting polyamine bead was deprotonated by washing with NaOH. The beads were washed with water such that the resulting effluent water approached neutral pH and dried.

The resulting dried polyamine bead was placed into a reactor and a solvent was added to the gel. The crosslinker was added to the resulting slurry. The mixture was heated for a required amount of time to reach completion. The reaction mixture was cooled and the beads were purified by washing and dried until no further water was removed and the weight remained constant. Examples of post-polymerization crosslinking described in this example include, but are not limited to, the crosslinkers shown in Table 10, Part 2. Table 11 describes key physicochemical properties (i.e. SGF binding and swelling ratio) of the polymer examples shown in Table 10_Part 2.

1. Post-Crosslinking of PAAH Beads with DCP

An aqueous stock solution was made by dissolving polyallylamine hydrochloride (average Mw ~15,000 (GPC vs. PEG std.)) (25 g)) and sodium hydroxide (6.0 g) in water (75.5 g). The solution was stirred for at least 10 minutes. A stock solution containing toluene (316 g) and surfactant (SPAN 80 (sorbitane monooleate)) (3.2 g) was also prepared. A 3-neck round bottom flask with four side baffles equipped with an overhead stirrer, Dean Stark apparatus and condenser were charged with the toluene solution. Dichloropropanol (1,3-Dichloro-2-propanol, "DC2POH") (3.45 g) was added to the aqueous stock solution at room temperature and stirred for 1 minute. This solution was added to the 3-neck round bottom flask set up. The reaction mixture was stirred under inert atmosphere. The reaction was heated to 50° C. for 14 hours. After this time, the reaction mixture was heated to 80° C., after which the reaction mixture was heated to 115° C. for a final dehydration step. Once all the water has been removed from the reaction (75 g), the reaction was allowed to cool to room temperature. The toluene was removed by decanting, and the resultant polymer beads were purified by washing with methanol (100 mL, two times), water (100 mL), 1M HCl (100 mL, two times), water (100 mL), 1M NaOH (100 mL, two times), and water until the pH of solution after washing was 7. The beads were dried in a lyophilizer for 48 hours.

0.40 g of the above resulting PAAH beads were mixed with 2.8 mL of methanol and 1,3-Dichloropropane ("DCP") (0.51 g) in a vial. The beads were mixed with a spatula to obtain equally distributed wetting before the vial was sealed and heated to 75° C. overnight. The cooled beads were purified by washing with methanol (45 mL, two times), water (45 mL), 1M HCl (45 mL, two times), water (45 mL), 1M NaOH (45 mL, three times), and water until the pH of solution after washing was 7. The gel was dried in a lyophilizer for 48 hours. This polymer is shown in Table 10_Part 2 and Table 11 as polymer number 4.

1. Post-Crosslinking of PAAH Beads with DCP

An aqueous stock solution was prepared by dissolving allylamine hydrochloride (10.71 g) and 1,3-Bis(allylamino)propane ("DAPDA") (6.50 g) in water (27.88 g). A 3-neck round bottom flask with four side baffles equipped with an overhead stirrer, Dean Stark apparatus and condenser, and nitrogen inlet was charged with aqueous stock solution and surfactant (Calimulse EM-99, branched dodecylbenzene sulfonate, 3.14 g) dissolved in a 74:26 chlorobenzene/heptane solution (311.11 g). In a separate vessel, a solution of V-50 (1.94 g) in water (11.00 g) was prepared. The two mixtures were independently sparged with nitrogen. Under inert atmosphere, the initiator solution was added to the reaction mixture, and subsequently heated to 67° C. for 16 hours. A second portion of initiator solution (12.94 g) and the reaction mixture were degassed and combined before increasing the temperature to 115° C. for a final dehydration step. After cooling the vessel to room temperature, the organic phase was removed by decanting, and the beads were purified by washing with methanol (100 mL, two times), water (100 mL), 2 M NaOH (100 mL), and water (100 mL, two times). The beads were dried in a lyophilizer for 48 hours.

1,3-Dichloropropane ("DCP") (0.18 g) was added to a vial charged with MeOH (2.80 g) and 0.40 g of the above resulting PAAH beads. The beads were mixed with a spatula to obtain equally distributed wetting before the vial was sealed and heated to 75° C. overnight. The cooled beads were purified by washing with methanol (45 mL, two times), water (45 mL), 1M HCl (45 mL, two times), water (45 mL), 1M NaOH (45 mL, two times), and water until the pH of solution after washing was 7. The gel was dried in a lyophilizer for 48 hours. This polymer is shown in Table 10_Part 2 and Table 11 as polymer number 10.

TABLE 10

Part 1: Synthesis of radical polymerization (addition/chain growth) beads

| Post-Crosslinked Monomer # | Amine | Crosslinker | Solvent | Surfactant | Amine (g) | Crosslinker 1 (g) | Solvent 1 (g) | Water (g) | Surfactant (g) | V-50 (g) |
|---|---|---|---|---|---|---|---|---|---|---|
| 1 | PAH | DC2OH | Toluene | Span80 | 25.00 | 3.45 | 315.96 | 75.43 | 3.19 | 0.00 |
| 2 | PAH | DC2OH | Toluene | Span80 | 25.00 | 3.45 | 315.96 | 75.43 | 3.19 | 0.00 |

TABLE 10-continued

| | | | | | | | | | | |
|---|---|---|---|---|---|---|---|---|---|---|
| 3 | PAH | DC2OH | Toluene | Span80 | 25.00 | 3.45 | 315.96 | 75.43 | 3.19 | 0.00 |
| 4 | PAH | DC2OH | Toluene | Span80 | 25.00 | 3.45 | 315.96 | 75.43 | 3.19 | 0.00 |
| 5 | PAH | BCPA | 3:1 PhCl:Heptane | Span80 | 2.64 | 1.16 | 70.00 | 10.00 | 0.71 | 0.00 |
| 6 | AAH | DAPDA | 3:1 PhCl:Heptane | EM-99 | 10.71 | 6.50 | 311.11 | 38.89 | 3.14 | 1.94 |
| 7 | AAH | DAPDA | 3:1 PhCl:Heptane | EM-99 | 10.71 | 6.50 | 311.11 | 38.89 | 3.14 | 1.94 |
| 8 | AAH | DAPDA | 3:1 PhCl:Heptane | EM-99 | 10.71 | 6.50 | 311.11 | 38.89 | 3.14 | 1.94 |
| 9 | AAH | DAPDA | 3:1 PhCl:Heptane | EM-99 | 10.71 | 6.50 | 311.11 | 38.89 | 3.14 | 1.94 |
| 10 | AAH | DAPDA | 3:1 PhCl:Heptane | EM-99 | 10.71 | 6.50 | 311.11 | 38.89 | 3.14 | 1.94 |
| 11 | AAH | DAPDA | 3:1 PhCl:Heptane | EM-99 | 10.71 | 6.50 | 311.11 | 38.89 | 3.14 | 1.94 |
| 12 | AAH | DAPDA | 3:1 PhCl:Heptane | EM-99 | 10.71 | 6.50 | 311.11 | 38.89 | 3.14 | 1.94 |
| 13 | AAH | DAPDA | 3:1 PhCl:Heptane | EM-99 | 12.30 | 9.95 | 300.00 | 50.00 | 3.03 | 2.38 |
| 14 | AAH | DAPDA | 3:1 PhCl:Heptane | EM-99 | 12.30 | 9.95 | 300.00 | 50.00 | 3.03 | 2.38 |
| 15 | AAH | DAPDA | 3:1 PhCl:Heptane | EM-99 | 12.30 | 9.95 | 300.00 | 50.00 | 3.03 | 2.38 |
| 16 | AAH | DAPDA | 3:1 PhCl:Heptane | EM-99 | 12.30 | 9.95 | 300.00 | 50.00 | 3.03 | 2.38 |
| 17 | AAH | DAPDA | 3:1 PhCl:Heptane | EM-99 | 12.30 | 9.95 | 300.00 | 50.00 | 3.03 | 2.38 |
| 18 | AAH | DAPDA | 3:1 PhCl:Heptane | EM-99 | 12.30 | 9.95 | 300.00 | 50.00 | 3.03 | 2.38 |
| 19 | AAH | DAPDA | 3:1 PhCl:Heptane | EM-99 | 12.30 | 9.95 | 300.00 | 50.00 | 3.03 | 2.38 |
| 20 | AAH | DAPDA | 3:1 PhCl:Heptane | EM-99 | 12.30 | 9.95 | 300.00 | 50.00 | 3.03 | 2.38 |
| 21 | AAH | DAPDA | 3:1 PhCl:Heptane | EM-99 | 10.96 | 11.40 | 300.00 | 50.00 | 3.03 | 2.27 |
| 22 | AAH | DAPDA | 3:1 PhCl:Heptane | EM-99 | 10.96 | 11.40 | 300.00 | 50.00 | 3.03 | 2.27 |
| 23 | AAH | DAPDA | 3:1 PhCl:Heptane | EM-99 | 10.96 | 11.40 | 300.00 | 50.00 | 3.03 | 2.27 |
| 24 | AAH | DAPDA | 3:1 PhCl:Heptane | EM-99 | 10.96 | 11.40 | 300.00 | 50.00 | 3.03 | 2.27 |
| 25 | AAH | DAPDA | 3:1 PhCl:Heptane | EM-99 | 10.96 | 11.40 | 300.00 | 50.00 | 3.03 | 2.27 |
| 26 | AAH | DAPDA | 3:1 PhCl:Heptane | EM-99 | 10.96 | 11.40 | 300.00 | 50.00 | 3.03 | 2.27 |
| 27 | AAH | DAPDA | 3:1 PhCl:Heptane | EM-99 | 10.96 | 11.40 | 300.00 | 50.00 | 3.03 | 2.27 |
| 28 | Sevelamer, free amine form, excipient removed | | | | | | | | | |
| 29 | AAH | DAEDA1 | 3:1 PhCl:Heptane | EM-99 | 10.94 | 6.23 | 311.11 | 38.89 | 3.14 | 1.98 |
| 30 | AAH | DAEDA1 | 3:1 PhCl:Heptane | EM-99 | 10.94 | 6.23 | 311.11 | 38.89 | 3.14 | 1.98 |
| 31 | AAH | DAEDA1 | 3:1 PhCl:Heptane | EM-99 | 10.94 | 6.23 | 311.11 | 38.89 | 3.14 | 1.98 |
| 32 | C2PW | ECH | Toluene | EM-99 | 3.75 | 3.56 | 64.88 | 7.50 | 0.40 | 0.00 |
| 33 | C2PW | ECH | Toluene | EM-99 | 3.75 | 4.75 | 64.88 | 7.50 | 0.40 | 0.00 |
| 34 | C2PW | ECH | Toluene | EM-99 | 3.75 | 4.75 | 64.88 | 7.50 | 0.40 | 0.00 |
| 35 | C2PW | ECH | Toluene | EM-99 | 3.75 | 4.75 | 64.88 | 7.50 | 0.40 | 0.00 |
| 36 | C2PW | ECH | Toluene | EM-99 | 3.75 | 4.75 | 64.88 | 7.50 | 0.40 | 0.00 |
| 37 | C2PW | ECH | Toluene | EM-99 | 3.75 | 5.93 | 64.88 | 7.50 | 0.40 | 0.00 |
| 38 | C2PW | ECH | Toluene | EM-99 | 3.75 | 5.93 | 64.88 | 7.50 | 0.40 | 0.00 |
| 39 | C2PW | ECH | Toluene | EM-99 | 3.75 | 7.12 | 64.88 | 7.50 | 0.40 | 0.00 |
| 40 | C2PW | ECH | Toluene | EM-99 | 3.75 | 7.12 | 64.88 | 7.50 | 0.40 | 0.00 |
| 41 | C2PW | ECH | Toluene | EM-99 | 8.33 | 7.91 | 72.08 | 16.67 | 0.30 | 0.00 |
| 42 | PDA1 | ECH | Toluene | EM-99 | 3.00 | 4.68 | 51.90 | 6.00 | 0.32 | 0.00 |
| 43 | PDA1 | ECH | Toluene | EM-99 | 3.00 | 4.68 | 51.90 | 6.00 | 0.32 | 0.00 |
| 44 | PDA1 | ECH | Toluene | EM-99 | 3.00 | 5.62 | 51.90 | 6.00 | 0.32 | 0.00 |
| 45 | PDA1 | ECH | Toluene | EM-99 | 3.00 | 5.62 | 51.90 | 6.00 | 0.32 | 0.00 |
| 46 | PDA1 | ECH | Toluene | EM-99 | 3.00 | 6.55 | 51.90 | 6.00 | 0.32 | 0.00 |
| 47 | PDA1 | ECH | Toluene | EM-99 | 3.00 | 6.55 | 51.90 | 6.00 | 0.32 | 0.00 |
| 48 | PDA1 | ECH | Toluene | EM-99 | 3.00 | 7.49 | 51.90 | 6.00 | 0.32 | 0.00 |
| 49 | PDA1 | ECH | Toluene | EM-99 | 3.00 | 7.49 | 51.90 | 6.00 | 0.32 | 0.00 |

V-50: 2,2'-Azobis(2-methylpropionamidine)dihydrochloride
Part 2: Synthesis of radical polymerization (addition/chain growth) beads

| Post-Crosslinked Monomer # | Secondary Crosslinking Recipe | | | | |
|---|---|---|---|---|---|
| | Crosslinker | Solvent | Bead (g) | Crosslinker (g) | Solvent (g) |
| 1 | DCP | MeOH | 0.40 | 0.01 | 2.80 |
| 2 | DCP | MeOH | 0.40 | 0.18 | 2.80 |
| 3 | DCP | MeOH | 0.40 | 0.34 | 2.80 |
| 4 | DCP | MeOH | 0.40 | 0.51 | 2.80 |
| 5 | DCP | H2O | 0.40 | 0.46 | 0.40 |
| 6 | DCP | H2O | 0.40 | 0.01 | 2.80 |
| 7 | DCP | H2O | 0.40 | 0.18 | 2.80 |
| 8 | DCP | H2O | 0.40 | 0.34 | 2.80 |
| 9 | DCP | H2O | 0.40 | 0.51 | 2.80 |
| 10 | DCP | MeOH | 0.40 | 0.18 | 2.80 |
| 11 | DCP | MeOH | 0.40 | 0.34 | 2.80 |
| 12 | DCP | MeOH | 0.40 | 0.51 | 2.80 |
| 13 | DCP | H2O | 0.40 | 0.47 | 0.40 |
| 14 | DCP | H2O | 0.40 | 0.47 | 0.80 |
| 15 | DCP | H2O | 0.40 | 0.47 | 1.20 |
| 16 | DCP | H2O | 0.40 | 0.47 | 1.60 |
| 17 | DCP | MeOH | 0.40 | 0.16 | 2.80 |
| 18 | DCP | MeOH | 0.40 | 0.32 | 2.80 |
| 19 | DCP | MeOH | 0.40 | 0.47 | 2.80 |
| 20 | DCP | DMF | 0.40 | 0.47 | 1.20 |
| 21 | DCP | H2O | 0.40 | 0.46 | 0.10 |
| 22 | DCP | H2O | 0.40 | 0.46 | 0.20 |
| 23 | DCP | H2O | 0.40 | 0.46 | 0.30 |
| 24 | DCP | H2O | 0.40 | 0.46 | 0.40 |

TABLE 10-continued

| | | | | | |
|---|---|---|---|---|---|
| 25 | DCP | H2O | 0.40 | 0.46 | 0.50 |
| 26 | DCP | H2O | 0.40 | 0.46 | 0.60 |
| 27 | DCP | 50% NaOH | 0.80 | 0.46 | 0.40 |
| 28 | DCP | 50% NaOH | 0.80 | 0.51 | 0.40 |
| 29 | DCP | H2O | 0.40 | 0.50 | 0.20 |
| 30 | DCP | H2O | 0.40 | 0.50 | 0.40 |
| 31 | DCP | H2O | 0.40 | 0.50 | 0.60 |
| 32 | DCP | H2O | 0.40 | 1.17 | 0.40 |
| 33 | DCP | H2O | 0.40 | 0.34 | 0.40 |
| 34 | DCP | H2O | 0.40 | 0.68 | 0.40 |
| 35 | DCP | H2O | 0.40 | 0.34 | 0.20 |
| 36 | DCP | H2O | 0.40 | 0.68 | 0.20 |
| 37 | DCP | H2O | 0.40 | 0.31 | 0.40 |
| 38 | DCP | H2O | 0.40 | 0.62 | 0.40 |
| 39 | DCP | H2O | 0.40 | 0.28 | 0.40 |
| 40 | DCP | H2O | 0.40 | 0.57 | 0.40 |
| 41 | DCP | Neat | 0.90 | 4.38 | 0.00 |
| 42 | DCP | H2O | 0.40 | 0.47 | 0.40 |
| 43 | DCP | H2O | 0.40 | 0.78 | 0.40 |
| 44 | DCP | H2O | 0.40 | 0.28 | 0.40 |
| 45 | DCP | H2O | 0.30 | 0.42 | 0.30 |
| 46 | DCP | H2O | 0.40 | 0.13 | 0.40 |
| 47 | DCP | H2O | 0.40 | 0.39 | 0.40 |
| 48 | DCP | H2O | 0.40 | 0.24 | 0.40 |
| 49 | DCP | H2O | 0.40 | 0.48 | 0.40 |

TABLE 11

Properties of radical polymerization (addition/chain growth) beads

| Post-Crosslinked Polymer # | Total Weight % Crosslinker | MW/N | Theoretical Capacity (mmol/g) | SGF (Cl) (mmol/g) | Swelling |
|---|---|---|---|---|---|
| 1 | 14.9% | 67.1 | 14.9 | 12.2 | 2.2 |
| 2 | 23.1% | 74.3 | 13.5 | 11.7 | 2.0 |
| 3 | 33.3% | 85.6 | 11.7 | 11.1 | 1.7 |
| 4 | 40.9% | 96.6 | 10.4 | 10.8 | 1.9 |
| 5 | 45.9% | 88.0 | 11.4 | 15.7 | 2.7 |
| 6 | 51.0% | 83.2 | 12.0 | 11.3 | 1.4 |
| 7 | 51.0% | 83.2 | 12.0 | 14.7 | 2.2 |
| 8 | 51.0% | 83.2 | 12.0 | 14.7 | 3.1 |
| 9 | 51.0% | 83.2 | 12.0 | 14.5 | 3.5 |
| 10 | 42.5% | 70.9 | 14.1 | 13.7 | 3.2 |
| 11 | 48.4% | 79.0 | 12.7 | 13.0 | 3.2 |
| 12 | 51.0% | 83.2 | 12.0 | 10.8 | 3.2 |
| 13 | 54.0% | 82.8 | 12.1 | 11.8 | 1.0 |
| 14 | 54.0% | 82.8 | 12.1 | 11.8 | 1.5 |
| 15 | 54.0% | 82.8 | 12.1 | 12.1 | 2.2 |
| 16 | 54.0% | 82.8 | 12.1 | 11.8 | 3.0 |
| 17 | 46.6% | 71.3 | 14.0 | 12.6 | 3.1 |
| 18 | 51.8% | 78.9 | 12.7 | 11.9 | 2.8 |
| 19 | 54.0% | 82.8 | 12.1 | 11.8 | 2.8 |
| 20 | 54.0% | 82.8 | 12.1 | 11.9 | 1.1 |
| 21 | 56.7% | 82.5 | 12.1 | 11.3 | 0.9 |
| 22 | 56.7% | 82.5 | 12.1 | 11.9 | 0.8 |
| 23 | 56.7% | 82.5 | 12.1 | 11.8 | 1.2 |
| 24 | 56.7% | 82.5 | 12.1 | 11.3 | 1.1 |
| 25 | 56.7% | 82.5 | 12.1 | 11.9 | 1.3 |
| 26 | 56.7% | 82.5 | 12.1 | 11.3 | 1.4 |
| 27 | 56.7% | 82.5 | 12.1 | 10.6 | 1.6 |
| 28 | 36.2% | 89.5 | 11.2 | 12.1 | 3.6 |
| 29 | 49.8% | 81.2 | 12.3 | 12.3 | 1.9 |
| 30 | 49.8% | 81.2 | 12.3 | 11.6 | 1.6 |
| 31 | 49.8% | 81.2 | 12.3 | 11.7 | 1.9 |
| 32 | 50.7% | 74.1 | 13.5 | 11.0 | 2.0 |
| 33 | 48.4% | 70.9 | 14.1 | 10.4 | 1.7 |
| 34 | 52.0% | 76.1 | 13.1 | 10.4 | 1.6 |
| 35 | 48.4% | 70.9 | 14.1 | 10.3 | 1.4 |
| 36 | 52.0% | 76.1 | 13.1 | 10.4 | 1.7 |
| 37 | 53.2% | 78.1 | 12.8 | 9.9 | 1.9 |
| 38 | 56.2% | 83.4 | 12.0 | 9.9 | 1.5 |
| 39 | 57.2% | 85.4 | 11.7 | 9.2 | 1.5 |
| 40 | 59.7% | 90.6 | 11.0 | 9.1 | 1.5 |
| 41 | 77.6% | 163.5 | 6.1 | 11.2 | 1.7 |
| 42 | 59.1% | 88.1 | 11.3 | 11.8 | 1.5 |
| 43 | 63.5% | 98.7 | 10.1 | 12.0 | 1.9 |
| 44 | 60.0% | 90.1 | 11.1 | 11.7 | 1.4 |
| 45 | 64.2% | 100.7 | 9.9 | 11.8 | 1.4 |
| 46 | 60.9% | 92.1 | 10.9 | 11.4 | 1.4 |
| 47 | 64.9% | 102.7 | 9.7 | 11.3 | 1.2 |
| 48 | 65.6% | 104.7 | 9.6 | 9.2 | 1.3 |
| 49 | 68.7% | 115.2 | 8.7 | 10.8 | 1.2 |

II. Performance Examples

The following examples provide the results of evaluating selected synthesized polymers of the current disclosure, as well as commercially available reference polymers, in performance-evaluating screens and assays measuring chloride binding selectivity over phosphate (SIB assay), chloride binding selectivity in presence of inorganic and organic interferents (SOB assay), total quaternary amines (QAA assay), SOB binding kinetics, and chloride retention (CRA assay). These assays are defined above.

A. Performance Example

The following Table 12 shows examples of the relative performance of three selected polymers: reference bixalomer prepared as described above, another C4A3BTA/ECH polymer with an increased ECH mole equivalent content, and free amine sevelamer. The assays used to generate the data in this example are described elsewhere.

Bixalomer reference crosslinked amine polymer prepared from C4A3BTA as monomer and ECH as crosslinker at a crosslinker molar equivalence of 2.35 was shown to have a swelling ratio of 2.3 g of water/g of dry polymer and a binding capacity of 12.8 mmol/g in SGF. This polymer bound 1.7 mmol/g chloride and 5.2 mmol/g phosphate in SIB and bound 0.8 mmol/g chloride, 1.4 mmol/g phosphate, 0.5 mmol/g citrate and 0.6 mmol/g taurocholate in SOB.

By comparison, crosslinked amine polymer prepared from C4A3BTA as a monomer and ECH as a crosslinker at a crosslinker molar equivalence of 5.3 was shown to have a swelling ratio of 0.9 g of water/g of dry polymer and a binding capacity of 11 mmol/g in SGF. This polymer bound 1.6 mmol/g chloride and 3.2 mmol/g phosphate in SIB and bound 3 mmol/g chloride, 0.5 mmol/g phosphate, 0 mmol/g citrate and 0 mmol/g taurocholate in SOB.

Free amine sevelamer polymer (prepared as described elsewhere) was shown to have a swelling ratio of 6.5 g of water/g of dry polymer and a binding capacity of 12.1 mmol/g in SGF. This polymer bound 1.1 mmol/g chloride and 6.1 mmol/g phosphate in SIB and bound 0.2 mmol/g chloride, 0.8 mmol/g phosphate, 0.4 mmol/g citrate and 1.8 mmol/g taurocholate in SOB.

Table 13 includes example polymers of the current disclosure whose swelling ratio is less than or equal to 2. Table 14 includes example polymers of the current disclosure whose swelling ratio is greater than 2, but less than or equal to 5.

TABLE 12

Comparative Performance of Selected Polymers

| Monomer | Crosslinker | Xlinker Mol. Eq. | Swelling (g/g) | SGF Cl BC (mmol/g) | SIB Cl BC (mmol/g) | SIB PO4 BC (mmol/g) | SOB Cl (mmol/g) | SOB PO4 (mmol/g) | SOB Citrate (mmol/g) | SOB TC (mmol/g) |
|---|---|---|---|---|---|---|---|---|---|---|
| C4A3BTA | ECH | 2.35 | 2.3 | 12.8 | 1.7 | 5.2 | 0.8 | 1.4 | 0.5 | 0.6 |
| C4A3BTA | ECH | 5.3 | 0.9 | 11.0 | 1.6 | 3.2 | 3.0 | 0.5 | 0.0 | 0.0 |
| Sevelamer free amine form - excipient removed | | | 6.5 | 12.1 | 1.1 | 6.1 | 0.2 | 0.8 | 0.4 | 1.8 |

TABLE 13

Example polymers of the current disclosure whose swelling ratio is less than or equal to 2

| Monomer | Crosslinker | Crosslinker Mol. Eq. | Swelling | SIB Cl (mmol/g) | SIB PO4 (mmol/g) | SOB Cl (mmol/g) | SOB PO4 (mmol/g) | SOB Citrate (mmol/g) | SOB TC (mmol/g) |
|---|---|---|---|---|---|---|---|---|---|
| AAH | TAA | 0.4 | 1.9 | 2.3 | 4.0 | 0.4 | 0.4 | 0.3 | 1.4 |
| AAH/20% DAEDA1 Bead | DCP | 0.7 | 1.6 | 2.5 | 3.2 | 4.4 | 0.1 | 0.0 | 0.1 |
| AAH/20% DAEDA1 Bead | DCP | 0.7 | 1.9 | 2.1 | 4.0 | 3.5 | 0.2 | 0.0 | 0.1 |
| AAH/20% DAEDA1 Bead | DCP | 0.7 | 1.9 | 2.6 | 3.6 | 4.5 | 0.3 | 0.0 | 0.0 |
| AAH/20% DAPDA Bead | DCP | 0.7 | 1.4 | 2.4 | 4.3 | 3.7 | 0.2 | 0.0 | 0.1 |
| AAH/25% DAPDA Bead | DCP | 0.7 | 1.0 | 3.1 | 3.5 | 4.1 | 0.2 | 0.0 | 0.0 |
| AAH/25% DAPDA Bead | DCP | 0.7 | 1.1 | 2.2 | 3.8 | 4.3 | 0.1 | 0.0 | 0.0 |
| AAH/25% DAPDA Bead | DCP | 0.7 | 1.5 | 2.7 | 4.4 | 3.4 | 0.5 | 0.1 | 0.2 |
| AAH/30% DAPDA Bead | DCP | 0.7 | 0.8 | 3.9 | 2.1 | 4.8 | 0.2 | 0.0 | 0.0 |
| AAH/30% DAPDA Bead | DCP | 0.7 | 0.9 | 3.9 | 1.7 | 3.7 | 0.1 | 0.0 | 0.0 |
| AAH/30% DAPDA Bead | DCP | 0.7 | 1.1 | 2.9 | 3.2 | 4.1 | 0.1 | 0.0 | 0.0 |
| AAH/30% DAPDA Bead | DCP | 0.7 | 1.2 | 3.6 | 2.3 | 4.1 | 0.2 | 0.0 | 0.0 |
| AAH/30% DAPDA Bead | DCP | 0.7 | 1.3 | 2.6 | 3.7 | 3.8 | 0.1 | 0.0 | 0.1 |
| AAH/30% DAPDA Bead | DCP | 0.7 | 1.4 | 2.4 | 4.0 | 3.6 | 0.3 | 0.0 | 0.1 |
| AAH/30% DAPDA Bead | DCP | 0.7 | 1.6 | 2.3 | 3.0 | 2.7 | 0.4 | 0.1 | 0.2 |
| C2A3BTA | ECH | 7.3 | 1.8 | 1.6 | 3.0 | nm | nm | nm | nm |
| C2A3BTA | ECH | 4.3 | 1.8 | 1.5 | 2.9 | nm | nm | nm | nm |
| C2A3BTA | ECH | 5.3 | 1.8 | 1.6 | 2.4 | nm | nm | nm | nm |
| C2A3BTA | ECH | 6.3 | 1.8 | 1.6 | 3.4 | nm | nm | nm | nm |
| C2A3BTA | ECH | 3.3 | 1.9 | 1.5 | 3.5 | nm | nm | nm | nm |
| C2A3G2 | ECH | 5.8 | 2.0 | 1.8 | 2.6 | nm | nm | nm | nm |
| C2PW | BCPA | 8.0 | 1.3 | 2.2 | 3.2 | 2.2 | 0.3 | 0.0 | 0.1 |
| C2PW | BCPA | 10.0 | 1.3 | 2.0 | 2.9 | 2.0 | 0.2 | 0.0 | 0.1 |
| C2PW | BCPA | 6.0 | 1.5 | 2.2 | 3.6 | 2.8 | 0.3 | 0.0 | 0.1 |
| C2PW | BCPA | 4.0 | 2.0 | 2.2 | 4.3 | 2.8 | 0.3 | 0.1 | 0.2 |
| C2PW | DCP | 4.0 | 1.6 | 2.0 | 2.8 | 1.5 | 0.0 | 0.0 | 0.1 |
| C2PW | DCP | 4.5 | 1.6 | 1.9 | 2.5 | 0.9 | 0.0 | 0.0 | 0.1 |
| C2PW | DCP | 3.5 | 2.0 | 2.1 | 3.4 | 1.7 | 0.2 | 0.0 | 0.1 |
| C2PW | ECH | 3.0 | 1.6 | 1.5 | 2.6 | 1.6 | 0.2 | 0.0 | 0.2 |
| C2PW | ECH | 2.5 | 1.7 | 1.4 | 3.1 | 1.6 | 0.4 | 0.1 | 0.3 |
| C2PW | ECH | 3.0 | 1.8 | 1.6 | 3.4 | 2.1 | 0.2 | 0.0 | 0.4 |
| C2PW | ECH | 3.5 | 1.8 | 1.7 | 2.1 | 1.4 | 0.1 | 0.0 | 0.2 |
| C2PW | ECH | 3.5 | 2.0 | 1.5 | 3.0 | 1.5 | 0.1 | 0.0 | 0.3 |
| C2PW | TGA | 2.3 | 1.3 | 1.3 | 1.7 | nm | nm | nm | nm |
| C2PW | TGA | 1.8 | 1.4 | 1.2 | 2.5 | 1.4 | 0.2 | 0.0 | 0.1 |
| C2PW | TGA | 1.3 | 1.7 | 1.2 | 3.6 | 0.7 | 0.7 | 0.2 | 0.6 |
| C2PW/ECH 1.5 eq Bead | DCP | 10.0 | 1.7 | 1.5 | 3.9 | 3.0 | 0.3 | 0.0 | 0.2 |
| C2PW/ECH 1.5 eq Bead | DCP | 1.5 | 2.0 | 1.5 | 4.2 | 2.1 | 0.4 | 0.1 | 0.4 |
| C2PW/ECH 2 eq Bead | DCP | 0.5 | 1.4 | 1.6 | 3.5 | 2.9 | 0.2 | 0.0 | 0.1 |
| C2PW/ECH 2 eq Bead | DCP | 1.0 | 1.6 | 1.6 | 3.6 | 2.6 | 0.2 | 0.0 | 0.3 |
| C2PW/ECH 2 eq Bead | DCP | 0.5 | 1.7 | 1.5 | 3.7 | 2.5 | 0.3 | 0.0 | 0.1 |
| C2PW/ECH 2 eq Bead | DCP | 1.0 | 1.7 | 1.6 | 3.5 | 2.9 | 0.2 | 0.0 | 0.1 |
| C2PW/ECH 2.5 eq Bead | DCP | 1.0 | 1.5 | 1.6 | 3.1 | 2.7 | 0.2 | 0.0 | 0.2 |
| C2PW/ECH 2.5 eq Bead | DCP | 0.5 | 1.9 | 1.6 | 3.2 | 2.4 | 0.1 | 0.0 | 0.3 |
| C2PW/ECH 3 eq Bead | DCP | 0.5 | 1.5 | 1.7 | 2.7 | 2.2 | 0.1 | 0.0 | 0.1 |

TABLE 13-continued

Example polymers of the current disclosure whose swelling ratio is less than or equal to 2

| Monomer | Cross-linker | Cross-linker Mol. Eq. | Swelling | SIB Cl (mmol/g) | SIB PO4 (mmol/g) | SOB Cl (mmol/g) | SOB PO4 (mmol/g) | SOB Citrate (mmol/g) | SOB TC (mmol/g) |
|---|---|---|---|---|---|---|---|---|---|
| C2PW/ECH 3 eq Bead | DCP | 1.0 | 1.5 | 1.7 | 2.7 | 2.5 | 0.2 | 0.0 | 0.1 |
| C3PW | DCP | 2.5 | 1.9 | 1.9 | 5.2 | 3.8 | 0.7 | 0.1 | 0.3 |
| C3PW | DCP | 3.0 | 1.9 | 2.0 | 4.9 | 3.7 | 0.4 | 0.1 | 0.2 |
| C3PW | DCP | 3.5 | 2.0 | 2.1 | 4.4 | 3.4 | 0.3 | 0.0 | 0.2 |
| C4A3BTA | BCPA | 12.0 | 1.4 | 2.0 | 3.6 | 3.3 | 0.3 | 0.0 | 0.1 |
| C4A3BTA | BCPA | 13.5 | 1.5 | 1.9 | 3.1 | 2.8 | 0.2 | 0.0 | 0.1 |
| C4A3BTA | BCPA | 10.5 | 1.8 | 2.0 | 3.5 | 3.3 | 0.3 | 0.0 | 0.1 |
| C4A3BTA | BCPA | 9.0 | 1.8 | nm | nm | 2.8 | 0.3 | 0.0 | 0.4 |
| C4A3BTA | BCPA | 7.0 | 2.0 | 2.1 | 4.3 | 2.9 | 0.5 | 0.1 | 0.4 |
| C4A3BTA | DCP | 5.3 | 1.2 | 2.0 | 3.0 | 1.6 | 0.1 | 0.0 | 0.1 |
| C4A3BTA | DCP | 2.8 | 1.4 | 2.3 | 5.3 | nm | nm | nm | nm |
| C4A3BTA | DCP | 3.8 | 1.6 | 2.3 | 4.1 | nm | nm | nm | nm |
| C4A3BTA | DCP | 7.3 | 1.6 | 1.5 | 2.7 | 0.6 | 0.1 | 0.0 | 0.3 |
| C4A3BTA | DCP | 3.3 | 1.7 | 2.3 | 4.7 | 3.5 | 0.4 | 0.0 | 0.2 |
| C4A3BTA | DCP | 2.3 | 1.7 | 2.0 | 5.6 | 2.0 | 1.6 | 0.4 | 0.4 |
| C4A3BTA | DCP | 6.3 | 1.8 | 1.9 | 3.4 | 1.5 | 0.1 | 0.0 | 0.2 |
| C4A3BTA | DCP | 4.3 | 1.8 | 2.4 | 3.3 | 2.8 | 0.6 | 0.0 | 0.1 |
| C4A3BTA | ECH | 5.3 | 0.9 | 1.6 | 3.2 | 3.0 | 0.5 | 0.0 | 0.0 |
| C4A3BTA | ECH | 6.3 | 1.1 | 1.5 | 3.8 | 1.7 | 0.5 | 0.0 | 0.0 |
| C4A3BTA | ECH | 7.3 | 1.2 | 0.6 | 2.9 | 1.6 | 0.6 | 0.0 | 0.0 |
| C4A3BTA | ECH | 5.3 | 1.3 | 1.8 | 2.7 | 1.8 | 0.1 | 0.0 | 0.1 |
| C4A3BTA | ECH | 3.3 | 1.4 | 1.7 | 3.9 | 2.8 | 0.2 | 0.0 | 0.2 |
| C4A3BTA | ECH | 4.3 | 1.5 | 1.8 | 3.0 | 2.3 | 0.1 | 0.0 | 0.1 |
| C4A3BTA | ECH | 6.3 | 1.6 | 1.9 | 1.9 | 1.4 | 0.0 | 0.0 | 0.0 |
| C4A3BTA | ECH | 3.1 | 1.6 | 1.5 | 4.6 | 2.8 | 0.8 | 0.0 | 0.3 |
| C4A3BTA | ECH | 7.3 | 1.9 | 1.9 | 1.5 | 1.3 | 0.0 | 0.0 | 0.1 |
| C4A3BTA | ECH | 3.9 | 1.9 | 1.6 | 4.6 | nm | nm | nm | nm |
| C4A3BTA | ECH | 2.3 | 1.9 | 1.6 | 5.1 | 1.0 | 1.4 | 0.4 | 0.5 |
| C4A3BTA | ECH | 2.9 | 1.9 | 1.7 | 4.8 | 2.0 | 1.4 | 0.2 | 0.4 |
| C4A3BTA | ECH | 2.5 | 2.0 | 1.7 | 5.0 | 1.4 | 1.2 | 0.3 | 0.6 |
| C4A3BTA | TGA | 3.0 | 1.5 | 1.5 | 2.5 | nm | nm | nm | nm |
| C4A3BTA | TGA | 2.3 | 1.7 | 1.4 | 2.8 | nm | nm | nm | nm |
| C4A3BTA | TGA | 1.7 | 2.0 | 1.7 | 4.1 | 0.7 | 0.5 | 0.3 | 1.1 |
| EDA1 | ECH | 2.5 | 2.0 | 1.2 | 2.6 | nm | nm | nm | nm |
| EDA3 | BCPA | 10.5 | 1.6 | 1.6 | 2.5 | 2.3 | 0.4 | 0.1 | 0.1 |
| EDA3 | BCPA | 8.5 | 1.6 | 1.9 | 2.7 | 2.6 | 0.3 | 0.0 | 0.1 |
| EDA3 | BCPA | 9.5 | 1.9 | 1.7 | 2.7 | 2.4 | 0.2 | 0.0 | 0.1 |
| EDA3 | BDE | 2.3 | 1.5 | 1.1 | 1.6 | nm | nm | nm | nm |
| EDA3 | BDE | 3.8 | 1.6 | 0.9 | 0.7 | nm | nm | nm | nm |
| EDA3 | BDE | 2.8 | 1.9 | 1.0 | 1.2 | nm | nm | nm | nm |
| EDA3 | BDE | 3.3 | 1.9 | 1.0 | 1.0 | nm | nm | nm | nm |
| PAH/10% DC2OH Bead | DCP | 0.5 | 1.7 | 2.1 | 3.9 | 2.8 | 0.1 | 0.0 | 0.1 |
| PAH/10% DC2OH Bead | DCP | 0.8 | 1.9 | 2.1 | 3.7 | 2.7 | 0.1 | 0.0 | 0.1 |
| PAH/10% DC2OH Bead | DCP | 0.3 | 2.0 | 2.0 | 4.4 | 2.8 | 0.4 | 0.0 | 0.1 |
| PDA1 | BCPA | 5.0 | 1.8 | 2.0 | 3.6 | 2.4 | 0.3 | 0.0 | 0.2 |
| PDA1 | DCP | 3.0 | 1.4 | 1.9 | 3.3 | 2.0 | 0.1 | 0.0 | 0.1 |
| PDA1 | DCP | 4.0 | 1.6 | 1.5 | 2.5 | 0.5 | 0.0 | 0.0 | 0.1 |
| PDA1 | DCP | 2.0 | 1.8 | 2.2 | 4.9 | 3.7 | 0.5 | 0.0 | 0.1 |
| PDA1 | ECH | 1.8 | 1.4 | 1.2 | 3.2 | 2.1 | 0.4 | 0.0 | 0.2 |
| PDA1 | ECH | 2.3 | 1.4 | 1.4 | 2.4 | 1.6 | 0.1 | 0.0 | 0.1 |
| PDA1 | ECH | 2.5 | 1.4 | 2.0 | 3.5 | 2.5 | 0.2 | 0.0 | 0.1 |
| PDA1 | ECH | 2.3 | 1.5 | 1.8 | 3.7 | 1.7 | 0.6 | 0.1 | 0.4 |
| PDA1 | ECH | 2.0 | 1.6 | 1.3 | 2.4 | 1.9 | 0.2 | 0.0 | 0.1 |
| PDA1 | ECH | 2.0 | 1.6 | 1.8 | 4.1 | 1.1 | 1.1 | 0.3 | 0.5 |
| PDA1 | ECH | 1.5 | 1.8 | 1.2 | 4.0 | 0.5 | 0.8 | 0.3 | 0.5 |
| PDA1 | ECH | 2.5 | 1.8 | 1.4 | 1.8 | 1.3 | 0.1 | 0.0 | 0.1 |
| PDA1 | TGA | 1.6 | 1.2 | 1.4 | 1.7 | nm | nm | nm | nm |
| PDA1 | TGA | 1.1 | 1.4 | 1.3 | 2.9 | 1.5 | 0.6 | 0.1 | 0.3 |
| PDA1/ECH 1.25 eq Bead | DCP | 0.8 | 1.5 | 1.6 | 4.0 | 2.6 | 0.4 | 0.1 | 0.4 |
| PDA1/ECH 1.25 eq Bead | DCP | 1.3 | 1.9 | 1.8 | 4.2 | 2.5 | 0.5 | 0.1 | 0.4 |
| PDA1/ECH 1.5 eq Bead | DCP | 0.5 | 1.4 | 1.7 | 3.9 | 2.6 | 0.4 | 0.0 | 0.3 |
| PDA1/ECH 1.5 eq Bead | DCP | 1.0 | 1.4 | 1.7 | 3.8 | 2.5 | 0.2 | 0.1 | 0.2 |
| PDA1/ECH 1.75 eq Bead | DCP | 0.8 | 1.2 | 1.9 | 3.6 | 2.6 | 0.2 | 0.0 | 0.2 |
| PDA1/ECH 1.75 eq Bead | DCP | 0.3 | 1.4 | 1.8 | 3.7 | 2.4 | 0.3 | 0.0 | 0.2 |
| PDA1/ECH 2 eq Bead | DCP | 1.0 | 1.2 | 1.9 | 5.6 | 1.8 | 0.2 | 0.0 | 0.1 |
| PDA1/ECH 2 eq Bead | DCP | 0.5 | 1.3 | 1.8 | 3.2 | 1.7 | 0.2 | 0.0 | 0.1 |

Cl = Chloride;
P: = Phosphate;
TC = Taurocholate;
nm = not measured

TABLE 14

Example polymers of the current disclosure whose swelling ratio is is greater than 2,
but less than or equal to 5

| Monomer | Cross-linker | Cross-linker Mol. Eq. | Swelling | SIB Cl (mmol/g) | SIB PO4 (mmol/g) | SOB Cl (mmol/g) | SOB PO4 (mmol/g) | SOB Citrate (mmol/g) | SOB TC (mmol/g) |
|---|---|---|---|---|---|---|---|---|---|
| AAH | DAEDA1 | 0.4 | 3.2 | 1.7 | 6.5 | 1.4 | 1.3 | 0.4 | 0.5 |
| AAH | DAPDA | 0.3 | 2.7 | 2.0 | 6.6 | 1.9 | 1.9 | 0.4 | 0.4 |
| AAH | DAPDA | 0.4 | 4.0 | 2.0 | 6.4 | 1.9 | 1.8 | 0.4 | 0.4 |
| AAH | DAPDA | 0.6 | 4.5 | 2.0 | 6.3 | 1.5 | 1.3 | 0.4 | 0.6 |
| AAH | DAPDA | 0.7 | 4.6 | 2.1 | 6.0 | 2.2 | 1.2 | 0.3 | 0.5 |
| AAH | DAPDA | 0.5 | 4.8 | 2.0 | 6.3 | 1.9 | 1.4 | 0.4 | 0.5 |
| AAH | TAA | 0.3 | 2.3 | 2.1 | 4.4 | 0.4 | 0.5 | 0.4 | 1.6 |
| AAH | TAA | 0.3 | 3.4 | 2.1 | 4.9 | 0.3 | 0.4 | 0.3 | 1.8 |
| AAH | TAA | 0.3 | 3.6 | 2.2 | 4.7 | 0.3 | 0.3 | 0.3 | 1.9 |
| AAH/20% DAPDA Bead | DCP | 0.7 | 2.2 | 2.3 | 4.6 | 2.5 | 0.9 | 0.2 | 0.3 |
| AAH/20% DAPDA Bead | DCP | 0.7 | 3.1 | 2.1 | 4.3 | 1.5 | 0.9 | 0.3 | 0.6 |
| AAH/20% DAPDA Bead | DCP | 0.3 | 3.2 | 1.9 | 5.3 | 1.0 | 1.1 | 0.4 | 1.0 |
| AAH/20% DAPDA Bead | DCP | 0.5 | 3.2 | 2.1 | 4.9 | 1.2 | 0.9 | 0.3 | 0.6 |
| AAH/20% DAPDA Bead | DCP | 0.7 | 3.2 | 2.2 | 4.7 | 1.4 | 0.8 | 0.3 | 0.4 |
| AAH/20% DAPDA Bead | DCP | 0.7 | 3.5 | 2.1 | 4.3 | 1.5 | 0.8 | 0.3 | 0.6 |
| AAH/25% DAPDA Bead | DCP | 0.7 | 2.2 | 2.3 | 4.3 | 2.1 | 0.9 | 0.3 | 0.4 |
| AAH/25% DAPDA Bead | DCP | 0.7 | 2.8 | 2.1 | 4.8 | 1.5 | 0.7 | 0.3 | 0.5 |
| AAH/25% DAPDA Bead | DCP | 0.5 | 2.8 | 2.1 | 5.0 | 1.4 | 0.8 | 0.3 | 0.6 |
| AAH/25% DAPDA Bead | DCP | 0.7 | 3.0 | 2.3 | 4.2 | 1.5 | 0.9 | 0.3 | 0.5 |
| AAH/25% DAPDA Bead | DCP | 0.3 | 3.1 | 2.0 | 5.4 | 1.0 | 1.0 | 0.3 | 0.9 |
| C2A3BTA | ECH | 4.3 | 2.9 | 1.8 | 3.8 | nm | nm | nm | nm |
| C2A3BTA | ECH | 5.3 | 3.1 | 1.6 | 3.5 | nm | nm | nm | nm |
| C2A3BTA | ECH | 3.3 | 3.5 | 1.7 | 4.1 | nm | nm | nm | nm |
| C2A3BTA | ECH | 4.8 | 3.7 | 1.6 | 4.0 | nm | nm | nm | nm |
| C2A3G2 | ECH | 7.3 | 2.3 | 1.7 | 1.9 | nm | nm | nm | nm |
| C2A3G2 | ECH | 4.3 | 2.4 | 1.7 | 3.7 | nm | nm | nm | nm |
| C2PW | BCPA | 5.0 | 2.2 | 1.7 | 4.0 | 2.8 | 0.4 | 0.1 | 0.3 |
| C2PW | DC2OH | 3.0 | 3.1 | 1.5 | 3.3 | nm | nm | nm | nm |
| C2PW | DC2OH | 2.5 | 3.4 | 1.4 | 3.5 | nm | nm | nm | nm |
| C2PW | DC2OH | 3.5 | 3.6 | 1.5 | 3.3 | nm | nm | nm | nm |
| C2PW | DC2OH | 1.5 | 4.2 | 1.6 | 4.4 | nm | nm | nm | nm |
| C2PW | DCP | 5.0 | 2.1 | 1.8 | 2.2 | 0.7 | 0.0 | 0.0 | 0.2 |
| C2PW | DCP | 2.5 | 2.2 | 2.1 | 4.8 | 2.9 | 0.7 | 0.1 | 0.5 |
| C2PW | DCP | 3.0 | 2.4 | 2.1 | 4.1 | 2.9 | 0.5 | 0.1 | 0.2 |
| C2PW | ECH | 2.5 | 2.3 | 1.4 | 4.0 | 1.1 | 1.0 | 0.2 | 0.7 |
| C3PW | DCP | 2.0 | 2.2 | 1.8 | 5.5 | 1.9 | 1.9 | 0.4 | 0.6 |
| C4A3BTA | BCPA | 5.0 | 2.3 | 2.2 | 4.7 | 2.6 | 0.8 | 0.2 | 0.5 |
| C4A3BTA | BCPA | 3.0 | 3.4 | 2.1 | 5.7 | 2.7 | 0.8 | 0.2 | 0.5 |
| C4A3BTA | TGA | 1.0 | 3.1 | 1.8 | 4.7 | nm | nm | nm | nm |
| EDA1 | DCP | 2.0 | 2.5 | 1.6 | 3.6 | 1.1 | 0.5 | 0.1 | 0.7 |
| EDA1 | DCP | 1.8 | 2.5 | 1.9 | 4.4 | 1.7 | 0.9 | 0.2 | 0.5 |
| EDA1 | DCP | 1.5 | 3.4 | 1.9 | 5.2 | 0.6 | 0.8 | 0.4 | 1.2 |
| EDA1 | ECH | 2.0 | 3.5 | 1.3 | 3.4 | nm | nm | nm | nm |
| EDA2 | DCP | 2.8 | 2.3 | 1.6 | 3.2 | 1.9 | 0.3 | 0.0 | 0.3 |
| EDA2 | DCP | 2.3 | 2.5 | 1.8 | 3.6 | 2.4 | 0.3 | 0.0 | 0.3 |
| EDA2 | DCP | 1.8 | 2.8 | 1.8 | 4.6 | 0.9 | 0.8 | 0.4 | 0.8 |
| EDA3 | BCPA | 7.5 | 2.9 | 0.8 | 4.2 | 1.8 | 0.6 | 0.1 | 0.4 |
| EDA3 | BCPA | 4.5 | 2.9 | nm | nm | 2.0 | 0.3 | 0.0 | 0.2 |
| EDA3 | BCPA | 6.0 | 3.3 | 1.1 | 4.8 | 1.2 | 1.1 | 0.2 | 0.7 |
| EDA3 | BCPA | 3.0 | 3.3 | nm | nm | 2.0 | 0.4 | 0.0 | 0.3 |
| EDA3 | DCP | 2.0 | 2.1 | 1.7 | 4.3 | 1.0 | 0.7 | 0.3 | 0.7 |
| EDA3 | DCP | 3.5 | 2.5 | 2.2 | 3.2 | 1.7 | 0.3 | 0.1 | 0.4 |
| EDA3 | DCP | 3.0 | 2.5 | 2.2 | 3.3 | 2.0 | 0.3 | 0.1 | 0.4 |
| EDA3 | DCP | 2.5 | 2.9 | 2.2 | 4.1 | 1.8 | 0.5 | 0.1 | 0.6 |
| EDA3 | ECH | 3.5 | 2.9 | 1.1 | 2.6 | nm | nm | nm | nm |
| EDA3 | ECH | 3.0 | 3.4 | 1.2 | 2.8 | nm | nm | nm | nm |
| PAH/10% DC2OH Bead | DCP | 0.1 | 2.2 | 1.9 | 4.9 | 1.9 | 1.0 | 0.1 | 0.3 |
| PAH/20% BCPA Bead | DCP | 0.7 | 2.7 | 3.1 | 6.4 | 4.8 | 0.7 | 0.1 | 0.2 |
| PDA1 | BCPA | 4.0 | 2.4 | 2.0 | 4.0 | 2.5 | 0.5 | 0.1 | 0.3 |
| PDA1 | BCPA | 3.0 | 2.6 | 2.1 | 4.5 | 1.9 | 0.7 | 0.3 | 0.7 |
| PDA1 | DC2OH | 2.0 | 3.5 | 1.2 | 2.9 | nm | nm | nm | nm |
| PDA1 | DCP | 5.0 | 2.4 | 1.6 | 2.4 | 0.7 | 0.1 | 0.0 | 0.1 |
| PDA1 | DCP | 6.0 | 2.9 | 1.3 | 2.1 | 0.4 | 0.1 | 0.0 | 0.4 |
| PDA1 | DCP | 1.8 | 4.1 | 2.2 | 6.3 | 0.8 | 1.4 | 0.5 | 1.7 |
| PDA1 | TGA | 0.6 | 4.7 | 1.5 | 4.1 | nm | nm | nm | nm |
| PDA2 | ECH | 2.5 | 2.7 | 1.5 | 3.2 | nm | nm | nm | nm |
| PDA2 | ECH | 3.0 | 2.9 | 1.4 | 2.3 | nm | nm | nm | nm |

TABLE 14-continued

Example polymers of the current disclosure whose swelling ratio is is greater than 2, but less than or equal to 5

| Monomer | Cross-linker | Cross-linker Mol. Eq. | Swelling | SIB Cl (mmol/g) | SIB PO4 (mmol/g) | SOB Cl (mmol/g) | SOB PO4 (mmol/g) | SOB Citrate (mmol/g) | SOB TC (mmol/g) |
|---|---|---|---|---|---|---|---|---|---|
| PDA2 | ECH | 1.5 | 3.2 | 1.6 | 3.3 | nm | nm | nm | nm |
| Sevelamer | DCP | 0.7 | 3.6 | 1.7 | 4.8 | 1.4 | 1.3 | 0.4 | 0.9 |

Cl = Chloride;
P: = Phosphate;
TC = Taurocholate;
nm = not measured

III. Screening Examples

The following examples illustrate means in which synthesized polymers may be characterized by some of the screens defined above.

A. Quaternized Amine Assay

A QAA assay was performed with selected polymers. The data for the QAA assay for the control materials Dowex 1×8, a commercially available, crosslinked polystyrene bead containing fully quaternized amines that was obtained as the chloride salt and was subsequently converted to the nitrate salt for this study, are shown in Table 15. The data for Amberlite IRA67, a commercially available crosslinked acrylic bead containing tertiary amines that was obtained and used in this example as in the free amine form, are shown in the first two rows of Table 15. As demonstrated therein, the fully quaternized Dowex 1×8, as expected, bound equal quantities of chloride, specifically 1.8 mmol Cl/g, under the acidic and basic pH conditions tested herein. Moreover, Amberlite IRA67, containing only tertiary amines, bound 5.9 mmol Cl/g under the acidic assay conditions employed, but bound 1.7% of this amount under the basic conditions tested herein, at which the constituent amines are mostly deprotonated. Table 15 also shows the amount of chloride binding by materials comprising C4A3BTA crosslinked with ECH at various mole equivalents of crosslinking agent. These materials, under the acidic conditions tested herein, demonstrate chloride binding >9 mmol Cl/g, frequently >10 mmol Cl/g, and under conditions of low crosslinking 13.4 mmol Cl/g. These same materials, under the basic pH conditions tested herein, demonstrate chloride binding <0.8 mmol Cl/g, frequently <0.5 mmol Cl/g, and under conditions of low crosslinking 0.3 mmol Cl/g. Under the assay conditions employed, C4A3BTA crosslinked with 3.3 mol equivalents of ECH demonstrated 1.9% amine quaternization, C4A3BTA crosslinked with 4.3 mol equivalents of ECH demonstrated 2.2% amine quaternization, C4A3BTA crosslinked with 5.3 mol equivalents of ECH demonstrated 6.2% amine quaternization, C4A3BTA crosslinked with 6.3 mol equivalents of ECH demonstrates 4.5% amine quaternization, and C4A3BTA crosslinked with 7.3 mol equivalents demonstrates 8.7% amine quaternization.

B. SOB Binding Kinetics

Selected polymers were evaluated in a SOB kinetic experiment, with anion binding being evaluated at 2, 24, and 48 hours of incubation. The data are described in Table 16. The bixalomer reference polymer prepared from C4A3BTA as monomer and ECH as crosslinker at a crosslinker to monomer ratio of 2.35 was shown to bind 0.8 mmol/g of chloride and 1.5 mmol/g of phosphate at 2 hours. After 48 hours of incubation in the same buffer, chloride and phosphate binding decreased to 0.4 and 1.0 mmol/g, respectively, and taurocholate binding increased from 0.6 mmol/g at 2 hours to 1.0 mmol/g at 48 hours. There was no change in citrate binding; this sample bound 0.5 mmol/g of citrate at 2 and 48 hours.

As shown in Table 16, a polymer prepared from C4A3BTA as a monomer and ECH at a higher crosslinker to monomer ratio of 4.3 bound 3.0 mmol/g of chloride and 0.2 mmol/g of phosphate at 2 hours. After 48 hours of incubation in the same buffer, chloride binding decreased to 1.9 mmol/g and phosphate binding increased to 0.9 mmol/g. Taurocholate binding increased from 0.2 mmol/g at 2 hours to 0.4 mmol/g at 48 hours. Citrate binding was 0.0 mmol/g of citrate at 2 and 48 hours.

As shown in Table 16, a polymer prepared from C4A3BTA as a monomer and ECH at an even higher crosslinker to monomer ratio of 7.3 was shown to bind 1.6 mmol/g of chloride and 0.6 mmol/g of phosphate at 2 hours. After 48 hours of incubation in the same buffer, chloride binding decreased to 1.2 mmol/g and phosphate binding increased to 1.0 mmol/g. Taurocholate binding was 0.0 mmol/g at 2 and 48 hours. Citrate binding increased from 0.0 mmol/g at 2 hours to 0.3 mmol/g at 48 hours.

C. Chloride Retention Assay

Selected polymers were evaluated for their ability to bind and retain chloride using the chloride retention assay (CRA). As shown in Table 17, Bixalomer reference polymer prepared from C4A3BT as monomer and ECH as a crosslinker at a crosslinker to monomer ratio of 2.35 was shown to initially bind 0.86 mmol/g of chloride in SOB buffer. The polymer sample was then allowed to incubate in a retention buffer (50 mM 2-(N-morpholino)ethanesulfonic acid (MES), 100 mM sodium acetate, 5 mM sodium phosphate, 15 mM sulphate, adjusted to pH 6.2) for approximately 40 hours at 37° C. followed by 16-20 hours incubation at 37° C. in an extraction solution (0.2 M sodium hydroxide). After extraction in 0.2 M sodium hydroxide, the sample was shown to have retained only 0.1 mmol/g of chloride ions that had bound in SOB, meaning the remaining chloride was released during the retention buffer incubation and water wash steps.

As shown in Table 17 In the same chloride retention assay, another polymer prepared from C4A3BTA as monomer and ECH as crosslinker at a crosslinker to monomer ratio of 5.3 was shown to initially bind 3.1 mmol/g of chloride in SOB buffer. The 0.2 M sodium hydroxide extraction showed that the sample retained 1.0 mmol/g of chloride with the remaining 2.1 mmol/g chloride having been released during the retention buffer incubation and water wash steps.

TABLE 15

QAA Results for Selected Commercial Reference and Example Polymers

| Sample ID | Monomer | Crosslinker | Crosslinker Eq. | SGF-Cl (mmol/g) | BCS-Cl (mmol/g) | % Quaternary-amines |
|---|---|---|---|---|---|---|
| Dowex 1 X 8 | Styrene | DVB | 8 | 1.8 | 1.8 | 100.0 |
| Amberlite IRA67 | Acrylic | NA | NA | 5.9 | 0.1 | 1.7 |
| 010001-A2 | C4A3BTA | ECH | 3.3 | 13.4 | 0.3 | 1.9 |
| 010001-A3 | C4A3BTA | ECH | 4.3 | 11.8 | 0.3 | 2.2 |
| 010001-A4 | C4A3BTA | ECH | 5.3 | 10.7 | 0.7 | 6.2 |
| 010001-A5 | C4A3BTA | ECH | 6.3 | 10.0 | 0.4 | 4.5 |
| 010001-A6 | C4A3BTA | ECH | 7.3 | 9.2 | 0.8 | 8.7 |

TABLE 16

SOB binding kinetics

| Amine | Cross-linker | Cross-linker/monomer ratio | SGF (mmol/g) | SIB Cl (mmol/g) | SIB P (mmol/g) | Swelling (gm/gm) | SOB Incubation time (hrs) | SOB Cl (mmol/g) | SOB P (mmol/g) | SOB Citrate (mmol/g) | SOB TC (mmol/g) |
|---|---|---|---|---|---|---|---|---|---|---|---|
| C4A3BTA | ECH | 2.35 | 12.8 | 1.7 | 5.2 | 2.3 | 2.0 | 0.8 | 1.5 | 0.5 | 0.6 |
| | | | | | | | 24.0 | 0.6 | 1.2 | 0.5 | 0.9 |
| | | | | | | | 48.0 | 0.4 | 1.0 | 0.5 | 1.0 |
| C4A3BTA | ECH | 4.3 | 11.4 | 1.2 | 4.0 | 1.5 | 2.0 | 3.0 | 0.2 | 0.0 | 0.2 |
| | | | | | | | 24.0 | 2.4 | 0.6 | 0.0 | 0.4 |
| | | | | | | | 48.0 | 1.9 | 0.9 | 0.0 | 0.4 |
| C4A3BTA | ECH | 7.3 | 8.2 | 0.6 | 2.9 | 1.2 | 2.0 | 1.6 | 0.6 | 0.0 | 0.0 |
| | | | | | | | 24.0 | 1.4 | 1.0 | 0.2 | 0.0 |
| | | | | | | | 48.0 | 1.2 | 1.0 | 0.3 | 0.0 |

TABLE 17

Chloride Retention Assay (CRA)

| Amine | Cross-linker | Cross-linker/monomer ratio | SGF (mmol/g) | SIB Cl (mmol/g) | SIB P (mmol/g) | Swelling (gm/gm) | Assay steps | mmol/g |
|---|---|---|---|---|---|---|---|---|
| C4A3BTA | ECH | 2.35 | 12.8 | 1.7 | 5.2 | 2.3 | Chloride bound in SOB buffer (mmol/g) | 0.86 |
| | | | | | | | Chloride released in retention buffer (mmol/g) | 0.37 |
| | | | | | | | Chloride bound after 0.2M extraction (mmol/g) | 0.1 |
| C4A3BTA | ECH | 5.3 | 11.0 | 1.6 | 3.2 | 0.9 | Chloride bound in SOB buffer (mmol/g) | 3.1 |
| | | | | | | | Chloride released in retention buffer (mmol/g) | 1.95 |
| | | | | | | | Chloride bound after 0.2M extraction (mmol/g) | 1.02 |

What is claimed is:

1. A method of treating metabolic acidosis in an animal, the method comprising oral administration to the animal of a pharmaceutical composition comprising a proton-binding, crosslinked amine polymer comprising the residue of an amine corresponding to Formula 2:

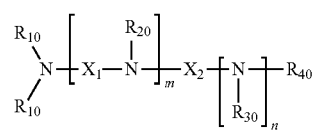

Formula 2 wherein m and n are independently non-negative integers;

$R_{10}$, $R_{20}$, $R_{30}$, and $R_{40}$ are independently hydrogen, hydrocarbyl, or substituted hydrocarbyl;

$X_1$ is

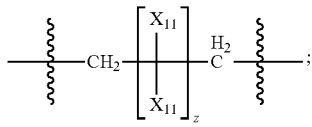

$X_2$ is hydrocarbyl or substituted hydrocarbyl;

each $X_{11}$ is independently hydrogen, hydrocarbyl, substituted hydrocarbyl, hydroxy, or amino;

z is a non-negative number;

the crosslinked amine polymer has an equilibrium swelling ratio in deionized water of 2 or less; and the crosslinked amine polymer binds a molar ratio of chloride ions to interfering ions of at least 0.35:1, respectively, in an interfering ion buffer at 37° C. wherein the interfering ions are phosphate ions and the interfering ion buffer is a buffered solution at pH 5.5 of 36 mM chloride and 20 mM phosphate.

2. The method of claim 1 wherein the crosslinked amine polymer has an equilibrium swelling ratio in deionized water of 1.5 or less.

3. The method of claim 1 wherein the crosslinked amine polymer comprises the residue of an amine corresponding to Formula 1a and the crosslinked amine polymer is prepared by radical polymerization of an amine corresponding to Formula 1a:

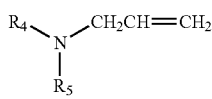

Formula 1a wherein $R_4$ and $R_5$ are independently hydrogen, hydrocarbyl, or substituted hydrocarbyl.

4. The method of claim 3 wherein $R_4$ and $R_5$ are independently hydrogen, alkyl, alkenyl, allyl, vinyl, aryl, aminoalkyl, alkanol, haloalkyl, hydroxyalkyl, ethereal, heteroaryl or heterocyclic.

5. The method of claim 3 wherein $R_4$ and $R_5$ are independently hydrogen, aliphatic or heteroaliphatic.

6. The method of claim 1 wherein the crosslinked amine polymer is prepared by substitution polymerization of the amine corresponding to Formula 2 with a polyfunctional crosslinker.

7. The method of claim 1 wherein $R_{10}$, $R_{20}$, $R_{30}$, and $R_{40}$ are independently hydrogen, aliphatic, aryl, heteroaliphatic, or heteroaryl, m and z are independently 0-3 and n is 0 or 1, and/or wherein $X_2$ is aliphatic or heteroaliphatic.

8. The method of claim 1 wherein m is 1-3 and $X_{11}$ is hydrogen, aliphatic or heteroaliphatic.

9. The method of claim 1 wherein the crosslinked amine polymer comprises the residue of an amine corresponding to Formula 2a:

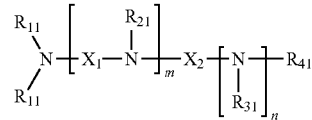

Formula 2a wherein m and n are independently non-negative integers;

each $R_{11}$ is independently hydrogen, hydrocarbyl, heteroaliphatic, or heteroaryl;

$R_{21}$ and $R_{31}$, are independently hydrogen or heteroaliphatic;

$R_{41}$ is hydrogen, substituted hydrocarbyl, or hydrocarbyl;

$X_1$ is

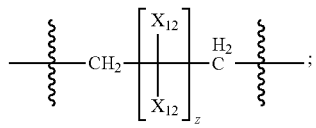

$X_2$ is alkyl or substituted hydrocarbyl;

each $X_{12}$ is independently hydrogen, hydroxy, amino, aminoalkyl, boronic acid or halo; and z is a non-negative number.

10. The method of claim 9 wherein m and z are independently 0-3 and n is 0 or 1.

11. The method of claim 9 wherein $R_{11}$ is independently hydrogen, aliphatic, aminoalkyl, haloalkyl, or heteroaryl, $R_{21}$ and $R_{31}$ are independently hydrogen or heteroaliphatic and $R_{41}$ is hydrogen, aliphatic, aryl, heteroaliphatic, or heteroaryl.

12. The method of claim 9 wherein each $R_{11}$ is hydrogen, aliphatic, aminoalkyl, or haloalkyl, $R_{21}$ and $R_{31}$ are hydrogen or aminoalkyl, and $R_{41}$ is hydrogen, aliphatic, or heteroaliphatic.

13. The method of claim 1 wherein the crosslinked amine polymer comprises the residue of an amine corresponding to Formula 2b:

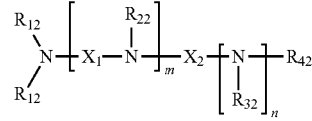

Formula 2b wherein m and n are independently non-negative integers;

each $R_{12}$ is independently hydrogen, substituted hydrocarbyl, or hydrocarbyl;

$R_{22}$ and $R_{32}$ are independently hydrogen substituted hydrocarbyl, or hydrocarbyl;

$R_{42}$ is hydrogen, hydrocarbyl or substituted hydrocarbyl;

$X_1$ is

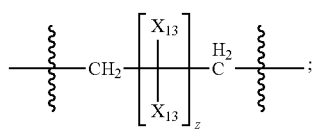

$X_2$ is alkyl, aminoalkyl, or alkanol;

each $X_{13}$ is independently hydrogen, hydroxy, alicyclic, amino, aminoalkyl, halogen, alkyl, heteroaryl, boronic acid or aryl;

z is a non-negative number; and the amine corresponding to Formula 2b comprises at least one allyl group.

14. The method of claim 13 wherein m and z are independently 0-3 and n is 0 or 1.

15. The method of claim 13 wherein $R_{12}$ or $R_{42}$ independently comprise at least one allyl or vinyl moiety.

16. The method of claim 13 wherein (i) m is a positive integer and $R_{12}$, $R_{22}$ and $R_{42}$, in combination comprise at least two allyl or vinyl moieties or (ii) n is a positive integer and $R_{12}$, $R_{32}$ and $R_{42}$, in combination, comprise at least two allyl or vinyl moieties.

17. The method according to claim 1 wherein the crosslinked amine polymer has a chloride ion to phosphate ion binding molar ratio of at least 0.5:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

18. The method of claim 1 wherein the crosslinked amine polymer has a chloride ion to phosphate ion binding molar ratio of at least 1:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

19. The method of claim 1 wherein the crosslinked amine polymer has a chloride ion to phosphate ion binding molar ratio of at least 2:1, respectively, in an aqueous simulated small intestine inorganic buffer ("SIB") containing 36 mM NaCl, 20 mM $NaH_2PO_4$, and 50 mM 2-(N-morpholino)ethanesulfonic acid (MES) buffered to pH 5.5 and at 37° C.

20. The method of claim 1 wherein the crosslinked amine polymer has a proton binding capacity of at least 10 mmol/g and a chloride ion binding capacity of at least 10 mmol/g in an aqueous simulated gastric fluid buffer ("SGF") containing 35 mM NaCl and 63 mM HCl at pH 1.2 and 37° C.

21. The method of claim 1 wherein the crosslinked amine polymer has an equilibrium proton binding capacity of at least 12 mmol/g and a chloride ion binding capacity of at least 12 mmol/g, in an aqueous simulated gastric fluid buffer ("SGF") containing 35 mM NaCl and 63 mM HCl at pH 1.2 and 37° C.

22. The method of claim 1 wherein the chloride binding in the SIB assay after one hour exposure of the polymer to the test buffer at 37° C. is greater than 2.0 mmol per gram of polymer.

23. The method of claim 1 wherein less than 1 g sodium or potassium is administered per day.

24. The method of claim 1 wherein the daily dose administered is less than 20 g.

25. The method of claim 1 wherein the daily dose is administered once a day.

26. The method of claim 1 wherein the metabolic acidosis is chronic metabolic acidosis.

27. The method of claim 1 wherein the daily dose results in a sustained serum bicarbonate increase of mEq/L.

28. The method of claim 1 wherein in said method the dose is titrated based on the serum bicarbonate values of the patient in need of treatment or other indicators of acidosis.

29. The method of claim 1 wherein the metabolic acidosis is characterized by a serum bicarbonate value of less than 22 mEq/l.

30. The method of claim 1 wherein the crosslinked amine polymer has an equilibrium proton binding capacity of at least 14 mmol/g and a chloride ion binding capacity of at least 14 mmol/g, in an aqueous simulated gastric fluid buffer ("SGF") containing 35 mM NaCl and 63 mM HCl at pH 1.2 and 37° C.

31. The method of claim 1 wherein the chloride binding in the SIB assay after one hour exposure of the polymer to the test buffer at 37° C. is greater than 2.5 mmol/g of polymer.

32. The method of claim 1 wherein the chloride binding in the SIB assay after one hour exposure of the polymer to the test buffer at 37° C. is greater than 3.0 mmol/g of polymer.

33. The method of claim 1 wherein the chloride binding in the SIB assay after one hour exposure of the polymer to the test buffer at 37° C. is greater than 3.5 mmol/g of polymer.

34. The method of claim 1 wherein the chloride binding in the SIB assay after one hour exposure of the polymer to the test buffer at 37° C. is greater than 4.0 mmol/g of polymer.

35. The method of claim 1 wherein less than 0.5 g of sodium or potassium is administered per day.

36. The method of claim 1 wherein less than 0.1 g of sodium or potassium is administered per day.

37. The method of claim 1 wherein no sodium or potassium is administered.

38. The method of claim 1 wherein the daily dose administered is less than 15 g.

39. The method of claim 1 wherein the daily dose administered is less than 10 g.

40. The method of claim 1 wherein the daily dose administered is less than 5 g.

41. The method of claim 1 wherein the daily dose administered is less than 4 g.

42. The method of claim 1 wherein the daily dose administered is less than 3 g.

43. The method of claim 1 wherein the daily dose is administered twice a day.

44. The method of claim 1 wherein the daily dose is administered three times a day.

45. The method of claim 1 wherein the daily dose results in a sustained serum bicarbonate increase of ≥5 mEq/L.

46. The method of claim 1 wherein the daily dose results in a sustained serum bicarbonate increase of ≥0 mEq/L.

* * * * *

UNITED STATES PATENT AND TRADEMARK OFFICE
CERTIFICATE OF CORRECTION

PATENT NO. : 10,391,118 B2
APPLICATION NO. : 16/002306
DATED : August 27, 2019
INVENTOR(S) : Klaerner et al.

Page 1 of 1

It is certified that error appears in the above-identified patent and that said Letters Patent is hereby corrected as shown below:

In the Claims

In Claim 27, at Line 4 of Column 98, the phrase "increase of mEq/L" should read --increase of ≥3 mEq/L--.

In Claim 46, at Line 55 of Column 98, the phrase "increase of ≥0 mEq/L" should read --increase of ≥10 mEq/L--.

Signed and Sealed this
Thirty-first Day of December, 2019

Andrei Iancu
*Director of the United States Patent and Trademark Office*